United States Patent
Farnaby et al.

(10) Patent No.: US 9,931,340 B2
(45) Date of Patent: Apr. 3, 2018

(54) PYRIDAZINONE COMPOUNDS AND THEIR USE AS DAAO INHIBITORS

(71) Applicant: TAKEDA PHARMACUETICAL COMPANY LTD., Osaka (JP)

(72) Inventors: William Farnaby, Cambridge (GB); Charlotte Fieldhouse, Cambridge (GB); Katherine Hazel, Cambridge (GB); Catrina Kerr, Dundee (GB); Natasha Kinsella, Kampala (UG); David Livermore, Cambridge (GB); Kevin Merchant, Cambridge (GB); David Miller, Cambridge (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 9 days.

(21) Appl. No.: 15/014,336

(22) Filed: Feb. 3, 2016

(65) Prior Publication Data

US 2017/0173007 A1  Jun. 22, 2017

Related U.S. Application Data

(62) Division of application No. 14/240,045, filed as application No. PCT/GB2012/000672 on Aug. 21, 2012, now Pat. No. 9,290,456.

(30) Foreign Application Priority Data

Aug. 22, 2011 (GB) .................................. 1114399.7
Oct. 27, 2011 (GB) .................................. 1118658.2
Feb. 29, 2012 (GB) .................................. 1203533.3

(51) Int. Cl.
*A61K 31/50* (2006.01)
*A61K 31/501* (2006.01)
*C07D 237/16* (2006.01)
*C07D 401/06* (2006.01)

(52) U.S. Cl.
CPC ............ *A61K 31/50* (2013.01); *A61K 31/501* (2013.01); *C07D 237/16* (2013.01); *C07D 401/06* (2013.01)

(58) Field of Classification Search
CPC ............................ C07D 237/16; C07D 401/06
See application file for complete search history.

(56) References Cited

U.S. PATENT DOCUMENTS

| 4,193,916 A | 3/1980 | Back et al. |
| 4,743,685 A | 5/1988 | Breuer et al. |
| 5,244,890 A | 9/1993 | Yamanaka et al. |
| 5,401,734 A | 3/1995 | Yamanaka et al. |
| 5,532,354 A | 7/1996 | Yamanaka et al. |
| 5,962,480 A | 10/1999 | Morguchi et al. |
| 9,180,122 B2 | 11/2015 | Farnaby et al. |
| 9,212,147 B2 | 12/2015 | Hondo et al. |

| 2010/0022526 A1 | 1/2010 | Lamberth et al. |
| 2013/0052281 A1 | 2/2013 | Farnaby et al. |
| 2014/0243353 A1 | 8/2014 | Farnaby et al. |
| 2014/0248378 A1 | 9/2014 | Cockcroft et al. |
| 2014/0336165 A1 | 11/2014 | Hondo et al. |
| 2015/0329495 A1 | 11/2015 | Farnaby et al. |

FOREIGN PATENT DOCUMENTS

| BE | 859 477 | 10/1977 |
| DE | 27 45 024 A1 | 10/1977 |
| EP | 0 180 298 | 5/1986 |
| EP | 0 593 110 | 4/1994 |
| EP | 2 314 586 A1 | 4/2011 |
| GP | 2 025 416 | 1/1980 |
| JP | 61-57563 | 3/1986 |
| JP | 62-84082 | 4/1987 |
| JP | 64-29367 | 1/1989 |
| JP | 1-202875 | 8/1989 |
| JP | 1-261392 | 10/1989 |
| JP | 2002-028187 | 1/1990 |
| JP | 5-255344 | 10/1993 |
| JP | 2009-02534 | 1/1997 |
| JP | 2001-519416 | 10/2001 |
| JP | 2007-517056 | 6/2007 |
| WO | WO 95/11235 | 4/1995 |
| WO | WO 99/10331 | 3/1999 |
| WO | WO 2002/053543 | 7/2002 |
| WO | WO 03/047558 A2 | 6/2003 |
| WO | WO 2003/062233 | 7/2003 |

(Continued)

OTHER PUBLICATIONS

International Search Report for International Patent Application No. PCT/GB2012/00672, dated Oct. 1, 2012.
Adage et al., "In vitro and in vivo pharmacological profile of AS057278, a selective D-amino acid oxidase inhibitor with potential anti-psychotic properties." European Neuropsychopharmacology, 2008, 18, 200-214.
Sparey, et al., "The discovery of fused pyrrole carboxylic acids as novel, potent D-amino acid oxidase (DAO) inhibitors,:" Bioorganic & Medicinal Chemistry Letters, 2006, 18, 3386-3391.
Ferraris, et al., "Synthesis and Biological Evaluation of D-Amino Acid Oxidase Inhibitors," J. Med. Chem., 2008, 51, 3357-3359.

(Continued)

*Primary Examiner* — Brian E McDowell
(74) *Attorney, Agent, or Firm* — Finnegan, Henderson, Farabow, Garrett & Dunner LLP.

(57) ABSTRACT

The present invention provides compounds of formula (I) and pharmaceutically acceptable salts thereof, wherein $R^1$ and $R^2$ are as defined in the specification, processes for their preparation, pharmaceutical compositions containing them and their use in therapy:

(I)

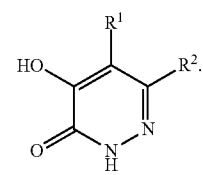

10 Claims, No Drawings

(56) References Cited

FOREIGN PATENT DOCUMENTS

| WO | WO 2004/094408 |      | 11/2004 |
|----|----------------|------|---------|
| WO | WO 2005/061458 |      | 7/2005  |
| WO | WO 2005/066135 |      | 7/2005  |
| WO | WO 2006/135828 |      | 12/2006 |
| WO | WO 2007/119434 | A1   | 10/2007 |
| WO | WO 2008/089453 |      | 7/2008  |
| WO | WO 2008/115381 |      | 9/2008  |
| WO | WO 2008/116301 |      | 10/2008 |
| WO | WO 2008/156607 |      | 12/2008 |
| WO | WO 2009/020814 |      | 2/2009  |
| WO | WO 2010/017418 |      | 2/2010  |
| WO | WO 2010/058314 | A1   | 5/2010  |
| WO | WO 2010/090737 | A1   | 8/2010  |
| WO | WO 2011/046920 |      | 4/2011  |
| WO | WO 2011/109254 |      | 9/2011  |
| WO | WO 2011/109261 |      | 9/2011  |
| WO | WO 2011/109267 |      | 9/2011  |
| WO | WO 2013/003383 | A1   | 1/2013  |
| WO | WO 2013/004995 |      | 1/2013  |
| WO | WO 2013/004996 |      | 1/2013  |
| WO | WO 2013/027000 |      | 2/2013  |
| WO | WO 2013/073577 |      | 5/2013  |
| WO | WO 2014/096757 |      | 6/2014  |

OTHER PUBLICATIONS

Duplantier et al., "Discovery, SAR, and Pharmacokinetics of a Novel 3-Hydroxyquinolin-2(1H)-one Series of Potent D-Amino Acid Oxidase (DAAO) Inhibitors," J. Med. Chem., 2009, 52, 3576-3585.
Hondo, et al., "4-Hydroxypyridazin-3(2H)-one derivatives as novel D-Amino add oxidase inhibitors," J. Med. Chem May 9, 2013; 56(9); 3582-92 (web publication date Apr. 9, 2013).
Division of Medicinal Scientific Abstracts for the 244$^{th}$ National Meeting and Exposition, Aug. 19-23, 2012, Philadelphia, PA: publication date Jul. 6, 2012 (see Entry MEDI 98).
Nakamura et al., "Studies on Prototropic Tautomerism in Nitrogen Heterocyclic Compounds, I. The hilannich Reaction of 2(1H)-Pyridone and 3-Hydroxy-2(1H)-pyridone)," Chem. Pharm. Bull., vol. 16, No. 8, 1968, 1466-1471 (1968).
Nakamura et al., "Studies on Prototropic Tautomerism in Nitrogen Heterocyclic Compounds, II, A Ring-Chain Tautomerism in 3-Hydroxy-6-(2-oxocycloalkyl)-methyl-2(1H)-pyridone and 3-Hydroxy-6-(3-oxoalkyl)-2(1H)-pyridone Derivatives," Chem. Pharm. Bull. vol. 17, No. 3, 1969, 425-433.
Dyumaev, K.M. et al., Aminomethylation of 2,3-dihydroxy- and 3-hydroxy-2-methoxypyridine, Zh., Khlm. 1972, Abstr. No. 1Zh309; CAS Database Accession No. 1972-564402 CAPLUS.
English Abstract of Aroyan, A. A. et al., Pyrimidine derivatives XXXVI, Synthesis and IR and mass spectra of 2-(p-alkoxybenzyl)-4,5-dihydroxypyrimidines, Amyanski Khimicheski Zhumal, vol. 27, No. 11, 1974, 963-968: CAS Database Accession No. 1975: 140063 CAPLUS.
U.S. Appl. No. 13/591,859, filed Aug. 22, 2012.
Office Action (Restriction Requirement) dated Jan. 24, 2013, in U.S. Appl. No. 13/591,859.
Office Action dated Sep. 19, 2013, in U.S. Appl. No. 13/591,859.
U.S. Appl. No. 14/131,343, filed Jan. 7, 2014.
U.S. Appl. No. 14/131,337, filed Jan. 7, 2014.
International Search Report, PCT/GB2012/000573, dated Sep. 10, 2012.
International Search Report, PCT/GB2012/000574, dated Oct. 11, 2012.
Bluth, R., "Pharmacological Characterization of Novel Pyridazines," Pharmazie, vol. 36, No. 11, pp. 775-777 (1961).
Feng, Yucheng et al., "Photoclytic and Micorbial Degradation of 3,5,6-trichioro-2-pyridinol," Environmental Toxicology and Chemistry, vol. 17, No. 5, pp. 814-819 (1996).
International Search Report for International Patent Application No. PCT/JP2012/079521, dated Jan. 22, 2013.
English language abstract of JP 02-028187, filed Jun. 6, 1989.
English language abstract of JP 09-025234, filed Jul. 12, 1995.
U.S. Appl. No. 14/358,162, filed May 14, 2014.
Office Action dated Mar. 19, 2015, in U.S. Appl. No. 14/131,343.
Hackam, et al., "Translation of Research Evidence from Animals to Humans," J. American Medical Association, 296(14), 2006, pp. 1731-1732.
Sunagawa et al., "Synthesis and Antibacterial Activity of Novel Carbapenems with a Catechol or Hydroxypyridone moiety." Journal of Antibiotics (1994) 47(11), 1354-1358.
Notice of Allowance dated Jul. 9, 2015, in U.S. Appl. No. 14/131,343.
Notice of Allowance dated Jul. 17, 2015, in U.S. Appl. No. 14/358,162.
Corrected Notice of Allowance dated Aug. 19, 2015, in U.S. Appl. No. 14/358,162.
Office Action dated Mar. 18, 2015, in U.S. Appl. No. 14/358,162.
Office Action dated May 8, 2015, in U.S. Appl. No. 13/591,859.
U.S. Appl. No. 14/652,484, filed Jun. 16, 2015.
International Search Report for International Patent Application No. PCT/GB2013/000552, Mar. 20, 2014.
U.S. Appl. No. 14/885,037, filed Oct. 16, 2015.
Office Action (Restriction Requirement) dated Dec. 1, 2015, in U.S. Appl. No. 14/131,337.
English Abstract of BE 859 477.
Jordan, V. C., "Tamoxifen: A most unlikely pioneering medicine," Nature Reviews: Drug Discovery, 2, 2003, 205-213.
Almond et al., "Behavioral and biochemical characterization of a mutant mouse strain lacking d-amino acid oxidase activity and its implications for schizophrenia," Molecular and Cellular Neurosciences, vol. 32, No. 4, pp. 324-334 (2006).
Hashimoto et al., "Mice lacking d-amino acid oxidase activity display marked attenuation of stereotypy and ataxia induced by MK-081," Brain Research, vol. 1033, No. 2, pp. 210-215 (2005).
Vree et al., "Novel oxidative pathways of sulphapyridine and sulphadiazine by the turtle *Pseudemys scripta elegans*," The Veterinary Quarterly, vol. 13, No. 4, pp. 218-224 (Oct. 1991).
CAS Database Accession No. 1978 512324 (1984).
CAS Database Accession No. 1972 564402 (1984).
CAS Database Accession No. RN 37749-03-4 (1984).
English language abstract of JP 61-57563, Mar. 24, 1986.
English language abstract of JP 64-29367, Jan. 31, 1989.
English language abstract of JP 1-202875, Aug. 15, 1989.
English language abstract of JP 1-261392, Oct. 18, 1989.
English language abstract of JP 5-255344, Oct. 5, 1993.
English language abstract of JP 2001-519416, Oct. 23, 2001.
English language abstract of JP 2007-517056, Jun. 28, 2007.
English language abstract of JP 62-84082, Apr. 17, 1987.

PYRIDAZINONE COMPOUNDS AND THEIR USE AS DAAO INHIBITORS

This application is a division of U.S. patent application No. 14/240,045, filed Feb. 21, 2014, which is a national stage filing under 35 U.S.C. § 371 of International Application No. PCT/GB2012/000672, filed on 21 Aug. 2012, which claims priority of Great Britain Patent Application No. 1114399.7, filed on 22 Aug. 2011, Great Britain Patent Application No. 1118658.2, filed 27 Oct. 2011, and Great Britain Patent Application No. 1203533.3, filed Feb. 29, 2012. The contents of these applications are incorporated herein by reference.

The present invention relates to pyridazinone derivatives, processes for their preparation, pharmaceutical compositions containing them and their use in therapy, particularly in the treatment or prevention of conditions having an association with the D-amino acid oxidase enzyme (DAAO).

The hyper-dopaminergic theory has driven schizophrenia drug discovery for decades and has produced notable drugs such as clozapine and olanzapine. Although these medicaments can be highly efficacious against the positive symptoms of schizophrenia and have significantly benefited many patients they are not the complete answer, with fewer or no effects against the negative and cognitive aspects of the disease and with undesired side effect profiles in some cases. Amongst alternative hypotheses the hyper-glutamatergic theory has much merit with the first real evidence coming from the use of PCP (phencyclidine), MK801 or ketamine, direct N-methyl-D-aspartate (NMDA)-receptor antagonists that are able to produce schizophrenia-like symptomatology in healthy human volunteers or exacerbate the clinical signs in schizophrenia patients. However, direct modulation of the NMDA receptor using agonists has not proved successful with excitotoxicity (excessive stimulation by the neurotransmitter) leading to undesirable side effects. An alternative approach is to target the co-agonists required for NMDA receptor activation. These are glycine and serine (D-SER). Attempts to enhance NMDA receptor activity through the use of glycine transporter inhibitors have produced clinical compounds (but no marketed drugs to-date). D-SER is a co-agonist with even greater potency than glycine and so modulation of D-SER may represent an alternative strategy. One way to increase levels of D-SER is to reduce the activity of DAAO, the enzyme which removes it from the synaptic cleft.

DAAO enzyme inhibitors are known in the art. For example, Adage et at, *European Neuropsychopharmacology* 2008, 18, 200-214 have described AS-057278, a small molecule DAAO enzyme inhibitor. Likewise, Sparey et al., *Bioorganic & Medicinal Chemistry Letters*, 2008, 18, 3386-3391 have demonstrated that molecules containing small heterocyclic rings furnished with a carboxylic acid group can inhibit the DAAO enzyme. DAAO inhibitors which avoid the carboxylic acid group have been described by Ferraris et al., *J. Med. Chem.* 2008, 51, 3357-3359 and by Duplantier et al., *J. Med. Chem.* 2009, 52, 3576-3585. A further series of carboxylic acid-containing DAAO enzyme inhibitors from Sepracore are described in WO 2008/089453.

We have now discovered a new class of compounds that are DAAO enzyme inhibitors which have desirable activity profiles. The compounds of this invention have beneficial potency, selectivity and/or pharmacokinetic properties.

In accordance with the present invention, there is therefore provided a compound of formula (I)

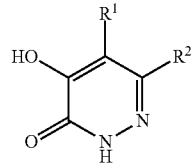

wherein
  $R^1$ represents a hydrogen or fluorine atom or a trifluoromethyl group;
  $R^2$ represents a group —X—Y—$R^3$;
  X and Y each independently represent a bond, an oxygen atom or a group —C(O), —S(O)$_n$, —C(O)N$R^4$, —S(O)N$R^4$, —N$R^4$,

or —C$R^4R^5$—, provided that X and Y cannot both simultaneously represent a bond and provided that if X and Y are both other than a bond, then at least one of X and Y represents —C$R^4R^5$—;
  n is 0, or 2;
  each $R^4$ independently represents a hydrogen atom or a $C_1$-$C_6$ alkyl or $C_1$-$C_6$ haloalkyl group;
  each $R^5$ independently represents a hydrogen atom, a $C_1$-$C_6$ alkyl or $C_1$-$C_6$ haloalkyl group or =CH—;
  $R^3$ represents a 3- to 10-membered saturated or unsaturated carbocyclic or heterocyclic ring system, the ring system itself being optionally substituted by at least one substituent selected from halogen, hydroxyl, cyano, oxo, $C_1$-$C_6$ alkyl, $C_2$-$C_6$ alkenyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylthio, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, amino (—NH$_2$), —CON($R^6$)$_2$, $C_1$-$C_6$ alkylamino, di-($C_1$-$C_6$ alkyl)amino, $C_3$-$C_6$ cycloalkyl, $C_3$-$C_6$ cycloalkyloxy, $C_3$-$C_6$ cycloalkylmethyl, —[O]$_p$—(CH$_2$)$_q$O—$R^7$ and a 4- to 6-membered saturated or unsaturated heterocyclic ring (optionally substituted with at least one substituent selected from $C_1$-$C_4$ alkyl and $C_1$-$C_4$ alkoxy);
  each $R^6$ independently represents a hydrogen atom or a $C_1$-$C_6$ alkyl group;
  p is 0 or 1;
  q is 1, 2, 3 or 4; and
  $R^7$ represents a $C_1$-$C_6$ alkyl group;
or a pharmaceutically acceptable salt thereof.

In the context of the present specification, unless otherwise stated, an alkyl, alkenyl or alkynyl substituent group or an alkyl, alkenyl or alkynyl moiety in a substituent group may be linear or branched. Examples of $C_1$-$C_6$ alkyl groups/moieties include methyl, ethyl, propyl, 2-methyl-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methy-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. Examples of $C_2$-$C_6$ alkenyl groups/moieties include ethenyl, propenyl, 1-butenyl, 2-butenyl, 1-pentenyl, 1-hexenyl, 1,3-butadienyl, 1, 3-pentadienyl, 1,4-pentadienyl and 1-hexadienyl. Examples of $C_2$-$C_6$ alkynyl groups/moieties include ethynyl, propynyl, 1-butynyl, 2-butynyl, 1-pentynyl and 1-hexynyl.

Similarly, an alkylene group/moiety may be linear or branched. Examples of $C_1$-$C_6$ alkylene groups/moieties include methylene, ethylene, n-propylene, n-butylene, n-pentylene, n-hexylene, 1-methylethylene, 2-methylethylene, 1,2-dimethylethylene, 1-ethylethylene, 2-ethylethylene, 1-, 2- or 3-methylpropylene and 1-, 2- or 3-ethylpropylene.

A $C_1$-$C_6$ haloalkyl or $C_1$-$C_6$ haloalkoxy substituent group/moiety will comprise at least one halogen atom, e.g. one, two, three, four or five halogen atoms, examples of which include fluoromethyl, difluoromethyl, trifluoromethyl, fluoromethoxy, difluoromethoxy, trifluoromethoxy or pentafluoroethyl.

A $C_1$-$C_6$ hydroxyalkyl substituent group/moiety will comprise at least one hydroxyl group, e.g. one, two, three or four hydroxyl groups, examples of which include —$CH_2OH$, —$CH_2CH_2OH$, —$CH_2CH_2CH_2OH$, —$CH(OH)CH_2OH$, —$CH(CH_3)OH$ and —$CH(CH_2OH)_2$.

The alkyl groups in a di-$C_1$-$C_6$ alkylamino group/moiety may be the same as, or different from, one another.

In the definition of $R^3$, the saturated or unsaturated 3- to 10-membered carbocyclic or heterocyclic ring system may have alicyclic or aromatic properties as too will the 4- to 6-membered saturated or unsaturated heterocyclic ring substituent. An unsaturated ring system will be partially or full unsaturated.

For the avoidance of doubt, when $R^3$ represents an optionally substituted 3- to 10-membered saturated or unsaturated carbocyclic or heterocyclic ring system, then it should be understood that the invention does not encompass any unstable ring structures or any O—O, O—S or S—S bonds and that a substituent, if present, may be attached to any suitable ring atom. The $R^3$ moiety may be attached at any heteroatom or carbon atom which results in the creation of a stable structure. Similar comments apply with respect to the optional 4- to 6-membered saturated or unsaturated heterocyclic ring substituent on the $R^3$ ring system.

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

In an embodiment of the invention, $R^1$ represents a hydrogen atom.

X and Y each independently represent a bond, an oxygen atom or a group —C(O), —S(O)$_n$, —C(O)NR$^4$, —S(O)$_2$NR$^4$, —NR$^4$,

or —CR$^4$R$^5$—, provided that X and Y cannot both simultaneously represent a bond and provided that if X and Y are both other than a bond, then at least one of X and Y represents —CR$^4$R$^5$—.

Each R$^4$ independently represents a hydrogen atom or a $C_1$-$C_6$, or $C_1$-$C_4$, or $C_1$-$C_2$ alkyl, preferably methyl, group or a $C_1$-$C_6$, or $C_1$-$C_4$, or $C_1$-$C_2$ haloalkyl, preferably trifluoromethyl, group.

Each R$^5$ independently represents a hydrogen atom, a $C_1$-$C_6$, or $C_1$-$C_4$, or $C_1$-$C_2$ alkyl, preferably methyl, group, a $C_1$-$C_6$, or $C_1$-$C_4$, or $C_1$-$C_2$ haloalkyl, preferably trifluoromethyl, group or a group =CH— such that —CR$^4$R$^5$— represents an alkenylene moiety, —CR$^4$=CH— or —CH=CR$^4$—.

In one embodiment of the invention, X represents a bond, an oxygen atom or a group —C(O), —S(O)$_n$, —C(O)NR$^4$, —S(O)NR$^4$, —NR$^4$,

or —CR$^4$R$^5$— (e.g. CH$_2$ or CH(CH$_3$)), and Y represents a bond or —CR$^4$R$^5$— (e.g. CH$_2$ or CH(CH$_3$)), subject to the above provisos.

In another embodiment of the invention, X represents a bond, an oxygen atom or a group —C(O), —S(O)$_n$, —C(O)NR$^4$, —S(O)$_2$NR$^4$,

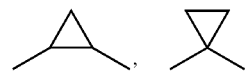

or —CR$^4$R$^5$— (e.g. CH$_2$ or CH(CH$_3$)), and Y represents a bond or —CR$^4$R$^5$— (e.g. CH$_2$ or CH(CH$_3$)), subject to the above provisos.

In still another embodiment of the invention, X represents —CR$^4$R$^5$— (e.g. CH$_2$ or CH(CH$_3$)) and Y represents a bond, an oxygen atom or a group —C(O), —S(O)$_n$, —C(O)NR$^4$, —S(O)$_2$NR$^4$, —NR$^4$,

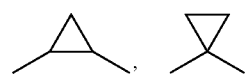

or —CR$^4$R$^5$— (e g, CH$_2$ or CH(CH$_3$)), subject to the above provisos.

In a further embodiment, X represents a group —S(O)$_n$ (e.g. —S—), —CHR$^4$ (e.g. CH$_2$ or CH(CH$_3$)) or

and Y represents a bond or a group —CHR$^4$ (e.g. CH$_2$), subject to the above provisos.

In a still further embodiment, X represents a group —S(O)$_n$ (e.g. —S—), —NR$^4$ (e.g. N(CH$_3$)), —CHR$^4$ (e.g. CH$_2$ or CH(CH$_3$)) or

especially —CHR$^4$, and Y represents a bond or a group —CHR$^4$ (e.g. CH$_2$), subject to the above provisos.

Specific examples of comb nations of X and Y include any one or more of the following:

| X | Y |
|---|---|
| S | CH$_2$ |
| CH$_2$ | S |
| CH$_2$ | CH$_2$ |
| S | CH(CH$_3$) |
| SO$_2$ | CH$_2$ |
| CH$_2$ | SO$_2$ |
| O | CH$_2$ |
| O | CH(CH$_3$) |
| C(O) | CH$_2$ |
| C(O)NH | CH$_2$ |
| S(O)$_2$NH | CH$_2$ |
| CH$_2$ | CH(CH$_3$) |
| CH(CH$_3$) | CH$_2$ |
| CH$_2$ | C(CH$_3$)$_2$ |
| C(CH$_3$)$_2$ | CH$_2$ |
| —CH═CH— | bond |
| bond | —CH═CH— |
| CH$_2$ | bond |
| bond | CH$_2$ |
| cyclopropyl | bond |
| bond | cyclopropyl |
| CH(CH$_3$) | bond |
| bond | CH(CH$_3$) |
| N(CH$_3$) | CH$_2$ |

In one embodiment of the invention, preferred combinations of X and Y include any one or more of the following:

| X | Y |
|---|---|
| S | CH$_2$ |
| CH$_2$ | CH$_2$ |
| CH$_2$ | bond |
| bond | CH$_2$ |
| Cyclopropyl (e.g. ) | bond |
| bond | Cyclopropyl (e.g. ) |
| CH(CH$_3$) | bond |
| bond | CH(CH$_3$) |
| N(CH$_3$) | CH$_2$ |

In still another embodiment of the invention, it is preferred that X and Y both represent CH$_2$.

Each $R^6$ independently represents a hydrogen atom or $C_1$-$C_6$, or $C_1$-$C_4$, or $C_1$-$C_2$ alkyl group. Examples of alkyl groups are described above and include methyl, ethyl, iso-propyl, n-propyl and n-butyl.

$R^7$ represents a $C_1$-$C_6$, or $C_1$-$C_4$, or $C_1$-$C_2$ alkyl group, examples of which have been previously described.

According to one aspect of the invention, $R^3$ may represent a 3- to 10-membered (e.g. 3-, 4-, 5- or 6- to 7-, 8-, 9- or 10-membered) saturated or unsaturated carbocyclic or heterocyclic ring system which is optionally substituted by at least one substituent (e.g. one, two, three or four substituents independently) selected from halogen (e.g. fluorine, chlorine or bromine), hydroxyl, cyano, oxo, $C_1$-$C_6$, or $C_1$-$C_4$, or $C_1$-$C_2$ alkyl, $C_2$-$C_6$ or $C_2$-$C_4$ alkenyl, $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylthio, $C_1$-$C_6$, or $C_1$-$C_4$, or $C_1$-$C_2$ alkylsulphinyl, $C_1$-$C_6$, or $C_1$-$C_4$, or $C_1$-$C_2$ alkylsulphonyl, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxycarbonyl, amino, —CON($R^6$)$_2$, $C_1$-$C_6$, or $C_1$-$C_4$, or $C_1$-$C_2$ alkylamino, di-($C_1$-$C_6$, or $C_1$-$C_4$, or $C_1$-$C_2$ alkyl)amino, $C_3$-$C_6$ or $C_3$-$C_5$ cycloalkyl, $C_3$-$C_6$ or $C_3$-$C_5$ cycloalkyloxy, $C_3$-$C_6$ or $C_3$-$C_5$ cycloalkylmethyl, —[O]$_p$—(CH$_2$)$_q$-Q-$R^7$ and a 4- to 6-membered saturated or unsaturated heterocyclic ring (optionally substituted with at least one substituent, e.g. one, two or three substituents independently, selected from $C_1$-$C_4$ alkyl such as methyl or ethyl and $C_1$-$C_4$ alkoxy such as methoxy or ethoxy).

The heterocyclic ring system will comprise at least one ring heteroatom (e.g. one, two, three or four ring heteroatoms independently) selected from nitrogen, sulphur and oxygen. Examples of saturated or unsaturated 3- to 10-membered carbocyclic or heterocyclic ring systems that may be used, which may be monocyclic or polycyclic (e.g. bicyclic) in which the two or more rings are fused, include one or more (in any combination) of cyclopropyl, cyclobutyl, cyclopentyl, cyclohexyl, bicyclo[2.2.1]heptyl, cyclopentenyl, cyclohexenyl, phenyl, pyrrolidinyl, piperidinyl, piperazinyl, morpholinyl, thiomorpholinyl, oxadiazolyl (e.g. 1,2,4-oxadiazolyl), tetrahydrofuranyl, diazabicyclo[2.2.1]hept-2-yl, naphthyl, benzofuranyl, benzothienyl, benzodioxolyl, quinolinyl, oxazolyl, thiadiazolyl (e.g. 1,2,3-thiadiazolyl), 2,3-dihydrobenzofuranyl, tetrahydropyranyl, pyrazolyl, imidazo[1,2-a]pyridinyl, pyrazinyl, thiazolidinyl, indanyl, thienyl, isoxazolyl, pyridazinyl, pyrrolyl, furanyl, thiazolyl, indolyl, imidazolyl, pyrimidinyl, benzimidazolyl, triazolyl, tetrazolyl and pyridinyl.

Preferred ring systems include phenyl, pyridinyl, oxazolyl, pyrazinyl, cyclopropyl, cyclopentyl, cyclohexyl, tetrahydropyranyl, 2,3-dihydrobenzofuranyl, pyrimidinyl, imidazo[1,2-a]pyridinyl, pyrazolyl, thiazolyl and piperidinyl.

Advantageously, the ring system is phenyl, pyridinyl, cyclopropyl, cyclopentyl, cyclohexyl or tetrahydropyranyl.

In a preferred embodiment of the invention, the ring system is phenyl or pyridinyl, particularly phenyl.

The 4- to 6-membered saturated or unsaturated heterocyclic ring substituent will comprise at least one ring heteroatom (e.g. one, two, three or four ring heteroatoms independently) selected from nitrogen, sulphur and oxygen. Preferably the ring heteroatoms are selected from nitrogen and oxygen. Examples of such ring substituents include azetidinyl, pyrrolidinyl and oxadiazolyl such as 1,2,4-oxadiazolyl.

In one embodiment of the invention, $R^3$ represents a 3-, 4- or 5- to 6-, 7-, 8- or 9-membered, e.g. 3- to 6- or 5- to 9-membered, saturated or unsaturated carbocyclic or heterocyclic ring system optionally substituted by at least one substituent (e.g. one, two, three or four substituents independently) selected from halogen (e.g. fluorine, chlorine or bromine), hydroxyl, cyano, oxo, $C_1$-$C_4$ alkyl (e.g. methyl or ethyl), $C_2$-$C_4$ alkenyl (e.g. ethenyl), $C_1$-$C_2$ haloalkyl (e.g. difluoromethyl or trifluoromethyl), $C_1$-$C_2$ hydroxyalkyl (e.g. hydroxymethyl), $C_1$-$C_4$ alkoxy (e.g. methoxy or ethoxy), $C_1$-$C_2$ haloalkoxy (e.g. difluoromethoxy or trifluoromethoxy), $C_1$-$C_4$ alkylthio (e.g. methylthio or ethylthio), $C_1$-$C_4$ alkylsulphinyl (e.g. methylsulphinyl or ethylsulphinyl), $C_1$-$C_4$ alkylsulphonyl (e.g. methylsulphonyl or ethylsulphonyl), $C_1$-$C_4$ alkylcarbonyl (e.g. methylcarbonyl or ethylcarbonyl), $C_1$-$C_4$ alkylcarbonyloxy (e.g. methylcarbonyloxy), $C_1$-$C_4$ alkoxycarbonyl (e.g. methoxycarbonyl), amino, —CON($R^6$)$_2$, $C_1$-$C_4$ alkylamino (e.g. methylamino or ethylamino), di-($C_1$-$C_4$ alkyl)amino (e.g. dimethylamino), $C_3$-$C_6$ cycloalkyl, $C_3$-$C_6$ cycloalkyloxy, $C_3$-$C_6$ cycloalkylmethyl, —[O]$_p$—(CH$_2$)$_q$—O—R$^7$ and a 4- to 6-membered saturated or unsaturated heterocyclic ring optionally substituted by methyl or methoxy.

In another embodiment of the invention, R$^3$ represents a 5- or 6-membered unsaturated carbocyclic or heterocyclic ring system, the heterocyclic ring system comprising one or two ring heteroatoms independendently selected from nitrogen and oxygen, wherein the carbocyclic or heterocyclic ring system is optionally substituted by one, two, three or four substituents independently selected from fluorine, chlorine, bromine, hydroxyl, cyano, oxo, C$_1$-C$_4$ alkyl (e.g. methyl or ethyl), C$_2$-C$_4$ alkenyl (e.g. ethenyl), C$_1$-C$_2$ haloalkyl (e.g. difluoromethyl or trifluoromethyl), C$_1$-C$_2$ hydroxyalkyl (e.g. hydroxymethyl), C$_1$-C$_4$ alkoxy (e.g. methoxy or ethoxy), C$_1$-C$_2$ haloalkoxy (e.g. difluoromethoxy or trifluoromethoxy), C$_1$-C$_4$ alkylthio (e.g. methylthio or ethylthio), C$_1$-C$_4$ alkylsulphinyl (e.g. methylsulphinyl or ethylsulphinyl), C$_1$-C$_4$ alkylsulphonyl (e.g. methylsulphonyl or ethylsulphonyl), C$_1$-C$_4$ alkylcarbonyl (e.g. methylcarbonyl or ethylcarbonyl), C$_1$-C$_4$ alkylcarbonyloxy (e.g. methylcarbonyloxy), C$_1$-C$_4$ alkoxycarbonyl (e.g. methoxycarbonyl), amino, carboxamido (—CONH$_2$), C$_1$-C$_4$ alkylamino (e.g. methylamino or ethylamino), di-(C$_1$-C$_4$ alkyl)amino (e.g. dimethylamino), C$_3$-C$_6$ cycloalkyl, C$_3$-C$_6$ cycloalkyloxy, C$_3$-C$_6$ cycloalkylmethyl, —[O]$_p$—(CH$_2$)$_q$—O—R$^7$ and a 4- to 6-membered saturated or unsaturated heterocyclic ring, preferably containing at least one ring nitrogen atom, optionally substituted by methyl or methoxy.

In still another embodiment, R$^3$ represents a 3- to 6-membered, preferably 5- to 6-membered, saturated or unsaturated carbocyclic or heterocyclic ring system such as cyclopropyl, cyclopentyl, cyclohexyl, tetrahydropyranyl, phenyl or pyridinyl, which ring system is optionally substituted by at least one substituent (e.g. one, two, three or four, preferably one or two, substituents independently) selected from cyano, fluorine, chlorine, methyl, difluoromethyl, difluoromethoxy, trifluoromethyl, trifluoromethoxy and methoxy.

Specific examples of R$^3$ include one or more of the following substituents in any combination:

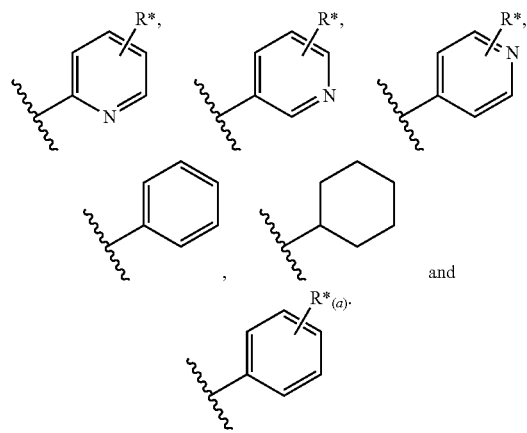

a = 1 or 2

The ring substituents R* are independently selected from cyano, halogen (e.g. fluorine or chlorine), methyl, methoxy, difluoromethyl, difluoromethoxy, trifluoromethyl or trifluoromethoxy.

In a preferred embodiment of the invention,
R$^1$ represents a hydrogen atom;
R$^2$ represents a group —X—Y—R$^3$;
X represents a group —S(O)$_n$ or —CHR$^4$ and Y represents a group —CHR$^4$;
n is 0, 1 or 2;
each R$^4$ independently represents a hydrogen atom or a methyl group; and
R$^3$ represents a 5- or 6-membered saturated or unsaturated carbocyclic or heterocyclic ring system, which ring system is optionally substituted by at least one substituent selected from fluorine, chlorine, trifluoromethyl and methoxy.

In another preferred embodiment of the invention,
R$^1$ represents a hydrogen atom;
R$^2$ represents a group —X—Y—R$^3$;
X represents a group —S(O)$_n$, —CHR$^4$ or

and Y represents a bond or a group —CHR$^4$;
n is 0, 1 or 2, preferably 0;
each R$^4$ independently represents a hydrogen atom or a methyl group, preferably a hydrogen atom; and
R$^3$ represents a 3- to 6-membered saturated or unsaturated carbocyclic or heterocyclic ring system (preferably phenyl), which ring system is optionally substituted by at least one substituent (preferably one or two substituents independently) selected from fluorine, chlorine, difluoromethyl, trifluoromethyl, trifluoromethoxy and methoxy.

In still another preferred embodiment of the invention,
R$^1$ represents a hydrogen atom;
R$^2$ represents a group —X—Y—R$^3$;
X represents a group —S(O)$_n$, —NR$^4$, —CHR$^4$ or

and Y represents a bond or a group —CHR$^4$;
n is 0, 1 or 2, preferably 0;
each R$^4$ independently represents a hydrogen atom or a methyl group, preferably a hydrogen atom; and
R$^3$ represents a 3- to 6-membered saturated or unsaturated carbocyclic or heterocyclic ring system (preferably phenyl), which ring system is optionally substituted by at least one substituent (preferably one or two substituents independently) selected from cyano, fluorine, chlorine, difluoromethyl, difluoromethoxy, trifluoromethyl, trifluoromethoxy, methyl and methoxy.

Examples of compounds of the invention include:
4-Hydroxy-6-(2-phenylethyl)pyridazin-3(2H)-one,
6-[2-(4-Fluorophenyl)ethyl]-4-hydroxypyridazin-3(2H)-one,
4-Hydroxy-6-{2-[5-(trifluoromethyl)pyridin-2-yl]ethyl}pyridazin-3(2H)-one,
6-[(4-Chlorobenzyl)sulfanyl]-4-hydroxypyridazin-3(2H)-one,
4-Hydroxy-6-{2-[6-(trifluoromethyl)pyridin-3-yl]ethyl}pyridazin-3(2H)-one,
6-[2-(3-Fluorophenyl)ethyl]-4-hydroxypyridazin-3(2H)-one,
6-[2-(2-Fluorophenyl)ethyl]-4-hydroxypyridazin-3(2H)-one, 6-[2-(3,5-Difluorophenyl)ethyl]-4-hydroxypyridazin-3 (2H)-one,
6-[2-(3,4-Difluorophenyl)ethyl]-4-hydroxypyridazin-3 (2H)-one,
4-Hydroxy-6-{2-[3-(trifluoromethoxy)phenyl]ethyl}pyridazin-3(2H)-one,
4-Hydroxy-6-{2-[3-(trifluoromethyl)phenyl]ethyl}pyridazin-3(2H)-one,
4-Hydroxy-6-{2-[5-(trifluoromethyl)pyridin-3-yl]ethyl}pyridazin-3(2H)-one,
6-(2-Cyclohexylethyl)-4-hydroxypyridazin-3(2H)-one,
6-(2-Cyclopropylethyl)-4-hydroxypyridazin-3(2H)-one,
6-(2-Cyclopentylethyl)-4-hydroxypyridazin-3(2H)-one,
4-Hydroxy-6-[2-(4-methoxycyclohexyl)ethyl]pyridazin-3 (2H)-one,
6-[2-(2,4-Difluorophenyl)ethyl]-4-hydroxypyridazin-3 (2H)-one,
6-{2-[3-(Difluoromethyl)phenyl]ethyl}-4-hydroxy-pyridazin-3(2H)-one,
6-Benzyl-4-hydroxypyridazin-3(2H)-one,
6-[2-(3-Chlorophenyl)ethyl]-4-hydroxypyridazin-3(2H)-one,
4-Hydroxy-6-(1-phenylcyclopropyl)pyridazin-3(2H)-one,
4-[2-(5-Hydroxy-6-oxo-1,6-dihydropyridazin-3-yl)ethyl] benzonitrile,
6-[2-(3-Fluoro-4-methylphenyl)ethyl]-4-hydroxy-pyridazin-3 (2H)-one,
6-[2-(4-Fluoro-3-methylphenyl)ethyl]-4-hydroxypyridazin-3(2H)-one,
6-[2-(3,4-Dimethoxyphenyl)ethyl]-4-hydroxypyridazin-3 (2H)-one,
4-Hydroxy-6-{2-[3-(trifluoromethoxy)phenyl]ethyl}pyridazin-3(2H)-one,
6-[2-(4-Chlorophenyl)ethyl]-4-hydroxypyridazin-3(2H)-one,
6-[2-(2-Chlorophenyl)ethyl]-4-hydroxypyridazin-3(2H)-one,
4-Hydroxy-6-{2-[2-(trifluoromethyl)phenyl]ethyl}pyridazin-3(2H)-one,
6-(4-(Difluoromethoxy)phenethyl)-4-hydroxypyridazin-3 (2H)-one,
6-(4-(Trifluoromethoxy)phenethyl)-4-hydroxypyridazin-3 (2H)-one,
6-(3-(Difluoromethoxy)phenethyl)-4-hydroxypyridazin-3 (2H)-one,
6-[1-(4-Fluorophenyl)cyclopropyl]-4-hydroxypyridazin-3 (2H)-one,
6-[1-(4-Fluorophenyl)ethyl]-4-hydroxypyridazin-3(2H)-one,
4-Hydroxy-6-{1-[3-(trifluoromethyl)phenyl]ethyl}pyridazin-3 (2H)-one,
4-Hydroxy-6-{2-[4-(trifluoromethyl)phenyl]ethyl}pyridazin-3(2H)-one,
6-((Cyclopropylmethyl)(methyl)amino)-4-hydroxy-pyridazin-3(2H)-one,
6-((Cyclohexylmethyl)(methyl)amino)-4-hydroxy-pyridazin-3(2H)-one,
6-(3-Chlorobenzyl)-4-hydroxypyridazin-3(2H)-one,
6-(4-Chlorobenzyl)-4-hydroxypyridazin-3(2H)-one,
6-(Cyclohexylmethyl)-4-hydroxypyridazin-3(2H)-one,
6-(4-Fluorobenzyl)-4-hydroxypyridazin-3(2H)-one,
6-(2-Chloro-6-fluorobenzyl)-4-hydroxypyridazin-3 (2H)-one,
6-(2-Chlorobenzyl)-4-hydroxypyridazin-3 (2H)-one,
6-(3-Fluorobenzyl)-4-hydroxypyridazin-(2H)-one,
6-(2-Fluorobenzyl)-4-hydroxypyridazin-3(2H)-one,
6-(4-Methylbenzyl)-4-hydroxypyridazin-3(2H)-one,
6-(3-Methylbenzyl)-4-hydroxypyridazin-3(2H)-one,
4-Hydroxy-6-(3-(trifluoromethyl)benzyl)pyridazin-3(2H)-one,
4-Hydroxy-6-{2-[5-(trifluoromethyl)pyridin-3-yl]ethy}pyridazin-3(2H)-one,
4-Hydroxy-6-[2-(oxan-4-yl)ethyl]pyridazin-3(2H)-one,
6-{[(4-Fluorophenyl)methyl](methyl)amino}-4-hydroxy-pyridazin-3(2H)-one,
6-[2-(2,6-Difluorophenyl)ethyl]-4-hydroxy-pyridazin-3 (2H)-one,
6-[(2(2-Chloro-6-fluorophenyl)ethyl]-4-hydroxy-pyridazin-3(2H)-one,
6-{[3,5-bis(Trifluoromethyl)phenyl]methyl}-4-hydroxy-pyridazin-3(2H)-one,
6-(1-Phenylethyl)-4-hydroxypyridazin-3(2H)-one,
6-(Cyclopropylmethyl)-4-hydroxy-2,3-dihydropyridazin-3-one,
4-Hydroxy-6-{1-[4-(trifluoromethyl)phenyl]cyclopropyl}-2,3-dihydropyridazin-3-one,
6-{2-[2-Chloro-4-(trifluoromethyl)phenyl]ethyl}-4-hydroxy-2,3-dihydropyridazin-3-one,
6-{2-[2-Fluoro-4-(trifluoromethyl)phenyl]ethyl}-4-hydroxy-2,3-dihydropyridazin-3-one,
6-{2-[3,5-bis(Trifluoromethyl)phenyl]ethyl}-4-hydroxy-2,3-dihydropyridazin-3-one,
6-{2-[2,4-bis(Trifluoromethyl)phenyl]ethyl}-4-hydroxy-2,3-dihydro-pyridazin-3-one,
6-{2-[3,4-bis(Trifluoromethyl)phenyl]ethyl}-4-hydroxy-2,3-dihydropyridazin-3-one,
4-Hydroxy-6-(3-methyl-4-(trifluoromethyl)phenethyl) pyridazin-3(2H)-one,
3,4-bis(Benzyloxy)-6-((3-chloro-4-(trifluoromethyl)phenyl) ethyl)-pyridazine,
4-Hydroxy-6-{2-[2-methyl-4-(trifluoromethyl)phenyl]ethyl}-2,3-dihydropyridazin-3-one,
6-{2-[3,5-Difluoro-4-(trifluoromethyl)phenyl]ethyl}-4-hydroxy-2,3-dihydropyridazin-3-one,
6-{2-[3-Fluoro-4-(trifluoromethyl)phenyl]ethyl}-4-hydroxy-2,3-dihydropyridazin-3-one, and pharmaceutically acceptable salts of any one thereof.

It should be noted that each of the chemical compounds listed above represents a particular and independent aspect of the invention.

The present invention further provides a process for the preparation of a compound of formula (I) or a pharmaceutically acceptable salt thereof as defined above which comprises (i) when X represents a sulphur atom or when X is a bond and Y represents a sulphur atom, reacting a compound of formula (II)

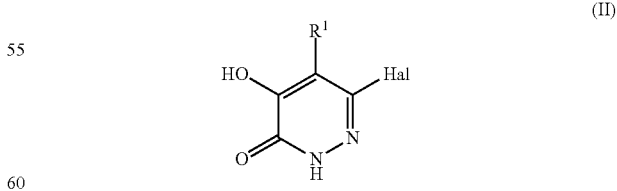

in which Hal represents a halogen atom such as chlorine and $R^1$ is as defined in formula (I), with a compound of formula (III), HS—[Y]$_t$—R$^3$, where t is 0 or 1 and Y and $R^3$ are as defined in formula (I); or (ii) when X represents SO or when X is a bond and Y represents SO, oxidising a compound of formula (IV)

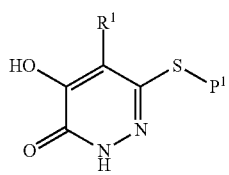

(IV)

in which $P^1$ represents a protecting group (e.g. methyl propionate) and $R^1$ is as defined in formula (I) with a suitable oxidising agent, followed by reaction with a compound of formula (V), $L^1$-$[Y]_w$—$R^3$, where w is 0 or 1, $L^1$ represents a leaving group (e.g. halogen) and Y and $R^3$ are as defined in formula (I); or (iii) when X represents $SO_2$ or when X is a bond and Y represents $SO_2$, oxidising a compound of formula (IV) as defined in (ii) above with a suitable oxidising agent, followed by reaction with a compound of formula (V) as defined in (ii) above; or (iv) when X represents an oxygen atom or when X is a bond and Y represents an oxygen atom, reacting a compound of formula (II) as defined in (i) above, with a compound of formula (VI), HO—$[Y]_z$—$R^3$, where z is 0 or 1 and Y and $R^3$ are as defined in formula (I); or (v) when X represents C(O) or when X is a bond and Y represents C(O), reacting a compound of formula (II) as defined in (i) above with carbon dioxide, followed by addition of an activating agent and reaction with a compound of formula (Va), M-$[Y]_w$—$R^3$, where M is Li or $MgR^{20}$, $R^{20}$ represents a halogen atom and w, Y and $R^3$ are as defined in formula (V) in (ii) above; or (vi) when X represents —C(O)$NR^4$ or when X is a bond and Y represents —C(O)$NR^4$, reacting a compound of formula (VII)

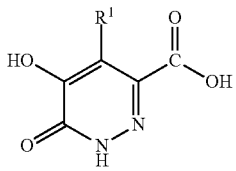

(VII)

in which $R^1$ is as defined in formula (I), with a compound of formula (VIII), $R^4$HN—$[Y]_g$—$R^3$, where g is 0 or 1 and Y, $R^3$ and $R^4$ are as defined in formula (I); or (vii) when X represents —$S(O)_2NR^4$ or when X is a bond and Y represents —$S(O)_2NR^4$, reacting a compound of formula (II) as defined in (i) above with sulphur dioxide, followed by addition of an oxidising-chlorinating agent and then reaction with a compound of formula (VIII) as defined in (vi) above; or (viii) when X represents —$NR^4$ or when X is a bond and Y represents —$NR^4$, reacting a compound of formula (II) as defined in (i) above, with a compound of formula (VIII) as defined in (vi) above; or (ix) when X represents —$CR^4R^5$— or when X is a bond and Y represents —$CR^4R^5$— and $R^4$ and $R^5$ each independently represent a $C_1$-$C_6$ alkyl group, reacting a compound of formula (II) as defined in (i) above with a compound of formula (IX), $L^2$-$CR^{4'}R^{5'}$—$[Y]_h$—$R^3$, where h is 0 or 1, $L^2$ represents a leaving group (e.g. halogen), $R^{4'}$ and $R^{5'}$ each independently represent a $C_1$-$C_6$ alkyl group and Y and $R^3$ are as defined in formula (I); or (x) when X represents —$CR^4R^5$— or when X is a bond and Y represents —$CR^4R^5$— and $R^4$ and $R^5$ each independently represent a hydrogen atom or a $C_1$-$C_6$ alkyl group but do not both simultaneously represent a $C_1$-$C_6$ alkyl group, reacting a compound of formula (II) as defined in (i) above with a compound of formula (IXa), $R^4$C(O)—$[Y]_h$—$R^3$, wherein h, Y, and $R^3$ are as defined in formula (IX) in (ix) above and $R^4$ is as defined in formula (I) above, followed by a hydrogenation reaction; or (xi) when X and Y each represent —$CHR^4$, hydrogenating a compound of formula (X)

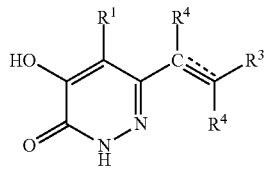

(X)

wherein $R^1$, $R^3$ and $R^4$ are as defined in formula (I), or (xii) when X represents —$CR^4R^5$— or when X is a bond and Y represents —$CR^4R^5$— and $R^5$ is =CH, reacting a compound of formula (XI)

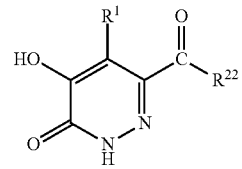

(XI)

wherein $R^{22}$ represents a hydrogen atom or a $C_1$-$C_6$ alkyl group and $R^1$ is as defined in formula (I), with a compound of formula (IXb), $R^{24}$—CH($R^{26}$)—$[Y]_h$—$R^3$, wherein $R^{24}$ represents a phosphonate moiety (e.g. —P(=O)(OR)$_2$ where R is an alkyl group such as ethyl), $R^{26}$ represents a hydrogen atom or a $C_1$-$C_6$ alkyl group and h, Y and $R^3$ are as defined in formula (IX) in (ix) above; or (xiii) when X represents a group

or when X is a bond and Y represents a group

reacting a compound of formula (XII)

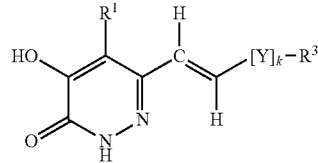

(XII)

where k is 0 or 1 and Y, $R^1$ and $R^3$ are as defined in formula (I), with diiodomethane and zinc-copper couple; or
(xiv) when X represents a group

or when X is a bond and Y represents a group

reacting a compound of formula (XIII)

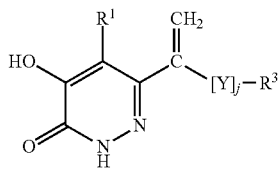

(XIII)

where l is 0 or 1 and Y, $R^1$ and $R^3$ are as defined in formula (I), with diiodomethane and zinc-copper couple;
and optionally thereafter carrying out one or more of the following procedures:
converting a compound of formula (I) into another compound of formula (I)
removing any protecting groups
forming a pharmaceutically acceptable salt.

Process (i) may conveniently be carried out in an organic solvent, such as toluene, in the presence of a palladium catalyst, e.g. tris(dibenzylideneacetone)dipalladium(0) ($Pd_2(DBA)_3$) and an organophosphorous compound such as 4,5-bis(diphenylphosphino)-9,9-dimethylxanthene (Xantphos).

Processes (ii) and (iii) may conveniently be carried out in an organic solvent, such as dichloromethane, using a suitable amount of an oxidising agent such as meta-chloroperoxybenzoic acid.

Process (iv) may conveniently be carried out in an organic solvent, such as toluene, in the presence of a copper (I) iodide catalyst at elevated temperature (e.g. 30° C. to 150° C.).

The first step of process (v) may conveniently be carried out in an organic solvent, such as diethyl ether, at low temperature (e.g. −78° C.) in the presence of a reagent such as butyllithium. A suitable activating agent to use in the second step would be a compound such as N,O-dimethylhydroxylamine hydrochloride which is commercially available, e.g. from the Sigma-Aldrich Corporation, to form a 'Weinreb amide' which is then reacted with the compound of formula (Va) to form the appropriate compound of formula (I).

Process (vi) may conveniently be carried out in an organic solvent using a suitable amide coupling reagent. Various amide coupling reagents are known in the art such as dicyclohexylcarbodiimide (DCC), diisopropylcarbodiimide (DIC), O-(benzotriazol-1-yl)-N,N,N',N'-tetramethyluronium hexafluorophosphate (HBTU) and O-(benzotriazol-1-yl)-N,N,N',N'-tetramethyluronium tetrafluoroborate (TBTU).

The first step of process (vii) may conveniently be carried out in an organic solvent, such as diethyl ether, at low temperature (e.g. −78° C.) in the presence of a reagent such as isopropylmagnesium chloride. A suitable oxidising-chlorinating agent to use in the second step would be sulphuryl chloride and the subsequent reaction with a compound of formula (VIII) may be carried out in accordance with known sulphonamide coupling procedures in the art.

The amination reaction in process (viii) may conveniently be carried out in an organic solvent, such as toluene, in the presence of (1) a palladium catalyst such as tris(dibenzylideneacetone)dipalladium(0) ($Pd_2(DBA)_3$), (2) a base such as sodium t-butoxide and (3) an organophosphorous compound such as 4,5-bis(diphenylphosphino)-9,9-dimethylxanthene (Xantphos).

Processes (ix) and (x) may conveniently be carried out in an organic solvent, such as diethyl ether, at low temperature (e.g. −78° C.) in the presence of a reagent such as butyllithium.

The hydrogenation reaction in process (x) and process (xi) may be carried out according to techniques known in the art, e.g. in the presence of an organic solvent, such as ethanol, using hydrogen gas and a palladium on carbon catalyst, under acid catalysed conditions as required.

Process (xii) is analogous to a Horner-Wadsworth-Emmons reaction as known, for example, from Wadsworth, W. Org. React 1977, 25, 73. Suitable reaction conditions for carrying out this type of reaction are known in the art.

Processes (xiii) and (xiv) are analogous to the Simmons-Smith cyclopropanation reaction of alkenes, for example, as described by Howard H. Simmons, Ronald D. Smith (1959) "A New Synthesis of Cyclopropanes" J. Am. Chem. Soc. 81 (16): 4256-4264.

Compounds of formula (IV) in which $P^1$ represents a protecting group such as —$CH_2CH_2C(O)OCH_3$ may be prepared by reacting a compound of formula (II) as defined above with methyl 3-sulfanylpropanoate.

Compounds of formula (VII) may be prepared by reacting a compound of formula (II) as defined above with carbon dioxide in an organic solvent such as diethyl ether at low temperature (e.g. −78° C.) in the presence of a reagent such as butyllithium.

Compounds of formula (X) in which the $CR^4$ groups are linked by a carbon-carbon double bond may be prepared by processes analogous to process (xii) above.

Compounds of formula (X) in which the $CR^4$ groups are linked by a carbon-carbon triple bond, each $R^4$ represents a hydrogen atom and $R^3$ represents an optionally substituted heterocyclic ring system may be prepared according to the following reaction scheme:

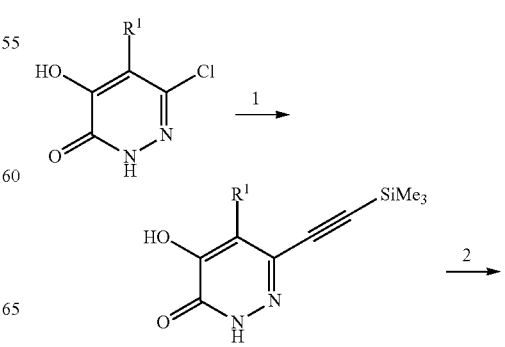

-continued

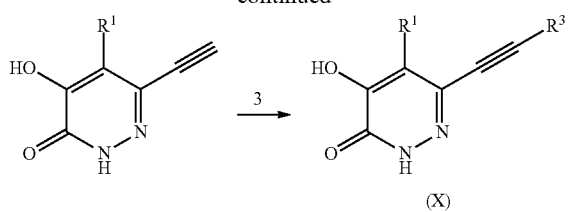

Step 1 is carried out by reacting the pyridazine compound (in which $R^1$ is as hereinbefore defined) With ethynyltrimethylsilane in an organic solvent such as tetrahydrofuran.

Step 2 is carried out using potassium carbonate in a polar solvent such as methanol.

Step 3 is carried out using a compound of formula $R^3$—Br where $R^3$ represents an optionally substituted heterocyclic ring system as hereinbefore defined, in the presence of copper(I) iodide and a suitable palladium catalyst.

Compounds of formula (X) in which the $CR^4$ groups are linked by a carbon-carbon triple bond, each $R^4$ represents a hydrogen atom and $R^3$ represents an optionally substituted carbocyclic ring system may be prepared according to the following reaction scheme:

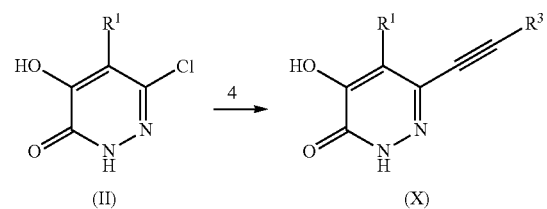

Step 4 is carried out by reacting the compound of formula (II) as hereinbefore defined with a compound of formula, HC≡C—$R^3$, where $R^3$ represents an optionally substituted carbocyclic ring system as hereinbefore defined, in the presence of copper(I) iodide and a suitable palladium catalyst.

Compounds of formula (XI) may be prepared by reacting a compound of formula (II) as defined above with dimethylformamide in an organic solvent, such as diethyl ether, at low temperature (e.g. −78° C.) in the presence of a reagent such as butyllithium, optionally followed by an alkylation reaction.

Compounds of formula (XII) may be prepared by processes analogous to those used for the preparation of compounds of formula (X).

Compounds of formula (XIII) may be prepared according to the following reaction scheme:

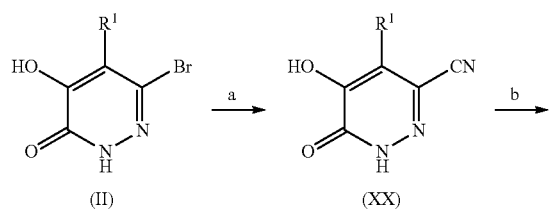

-continued

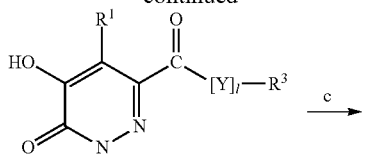

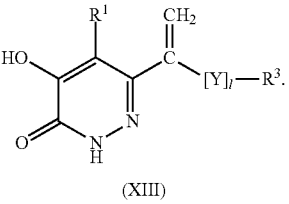

Step a is carried out using, for example, copper cyanide. The compound of formula (II) is as hereinbefore defined.

Step b is carried out using a Grignard reagent of formula $R^3$—[Y]$_t$—MgBr where l, Y and $R^3$ are as defined in formula (XIII).

Step c is carried out using Tebbe reagent solution (bis(cyclopentadienyl)-μ-chloro-(dimethylaluminum)-μ-methylenetitanium).

Compounds of formulae (II), (III), (V), (Va), (VI), (VIII), (IX), (IXa) and (IXb) are either commercially available, are well known in the literature or may be prepared using known techniques.

The present invention further provides certain novel intermediates, e.g. intermediates of formula (XXX),

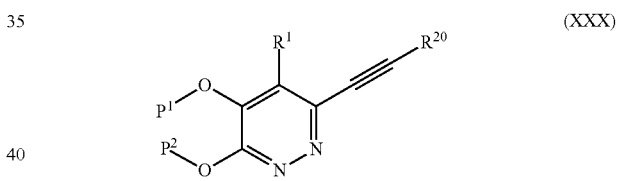

wherein $P^1$ and $P^2$ each independently represent a protecting group (e.g. benzyl), $R^{20}$ represents a hydrogen atom or a leaving group (e.g. trimethylsilane, $Si(CH_3)_3$) and $R^1$ is as defined in formula (I) above.

It will be appreciated by those skilled in the art that in the processes of the present invention certain functional groups such as phenol, hydroxyl or amino groups in the reagents may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate or p-toluenesulphonate salt.

In one aspect of the invention, compounds of formula (I) may bear one or more radiolabels. Such radiolabels may be introduced by using radiolabel-containing reagents in the synthesis of compounds of formula (I), or may be introduced by coupling the compounds of formula (I) to chelating moieties capable of binding to a radioactive metal atom. Such radiolabeled versions of the compounds may be used, for example, in diagnostic imaging studies.

Compounds of formula (I) and their salts may be in the form of hydrates or solvates which form an aspect of the present invention. Such solvates may be formed with common organic solvents, including but not limited to, alcoholic solvents e.g. methanol, ethanol or isopropanol.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) and their pharmaceutically acceptable salts have activity as pharmaceuticals, in particular as D-amino acid oxidase enzyme (DAAO) inhibitors, and thus may be used in the treatment of schizophrenia and other psychotic disorders (e.g., psychotic disorder, psychosis), dementia and other cognitive disorders, anxiety disorders (e.g., generalized anxiety disorder), mood disorders (e.g., depressive disorders, major depressive disorders, bipolar disorders including bipolar I and II, bipolar mania, bipolar depression), sleep disorders, disorders usually first diagnosed in infancy, childhood, or adolescence (e.g., attention-deficit disorder and disruptive behaviour disorders), pain (e.g. neuropathic pain) and neurodegenerative disorders (e.g. Parkinson's or Alzheimer's disease).

Thus, the present invention provides a compound of formula (I) or a pharmaceutically acceptable salt thereof as hereinbefore defined for use in therapy, in particular for the treatment of conditions whose development or symptoms are linked to DAAO enzyme activity.

The present invention also provides the use of a compound of formula (I) or a pharmaceutically acceptable salt thereof as hereinbefore defined for the preparation of a medicament for the treatment of conditions whose development or symptoms are linked to DAAO enzyme activity.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

In particular, the compounds of the invention (including pharmaceutically acceptable salts) may be used in the treatment of the positive symptoms of schizophrenia, schizophreniform disorder or schizoaffective disorder (e.g. voices or hallucinations), cognitive disorders (such as dementia and impaired learning) and also pain (such as neuropathic pain).

The invention also provides a method of treating at least one symptom or condition associated with schizophrenia, schizophreniform disorder, schizoaffective disorder and other psychotic disorders (e.g., psychotic disorder, psychosis), dementia and other cognitive disorders, anxiety disorders (e.g., generalized anxiety disorder), mood disorders (e.g., depressive disorders, major depressive disorders, bipolar disorders including bipolar I and II, bipolar mania, bipolar depression), sleep disorders, disorders usually first diagnosed in infancy, childhood, or adolescence (e.g., attention-deficit disorder, autistic spectrum disorders and disruptive behaviour disorders), pain (e.g. neuropathic pain) and neurodegenerative disorders (e.g. Parkinson's or Alzheimer's disease) which comprises administering to a patient in need thereof a therapeutically effective amount of a compound of formula (I) or a pharmaceutically acceptable salt thereof as hereinbefore defined.

Such symptoms and conditions include, but are not limited to, anxiety, agitation, hostility, panic, an eating disorder, an affective symptom, a mood symptom, a negative and positive psychotic symptom commonly associated with psychosis and neurodegenerative disorder.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore the present invention further provides a pharmaceutical composition comprising a compound of formula (I) or a pharmaceutically acceptable salt thereof as hereinbefore defined, in association with a pharmaceutically acceptable adjuvant, diluent or carrier.

The invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant such as that described in Ph. Helv. or a similar alcohol.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of the invention (that is, compounds of formula (I) and pharmaceutically acceptable salts thereof) may also be administered in conjunction with other compounds used for the treatment of the above conditions and/or with serine.

The invention therefore further relates to combination therapies wherein a compound of the invention or a pharmaceutical composition or formulation comprising a compound of the invention is administered with another therapeutic agent or agents and/or with serine, for the treatment of one or more of the conditions previously indicated. Such therapeutic agents may be selected from the following:

(i) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, thionisoxetine, tranylcypromaine, trazodone, trimipramine, venlafaxine, and equivalents and pharmaceutically active isomer(s) and/or metabolite(s) thereof;

(ii) atypical antipsychotics including, for example, quetiapine and pharmaceutically active isomer(s) and/or metabolite(s) thereof;

(iii) antipsychotics including, for example, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perpbenazine, phenothiazine, phenylbutlypiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone, and equivalents and pharmaceutically active isomer(s) and/or metabolite(s) thereof;

(iv) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or metabolite(s) thereof;

(v) anticonvulsants including, for example, carbamazepine, valproate, lamotrigine, and gabapentin, and equivalents and pharmaceutically active isomer(s) and/or metabolite(s) thereof;

(vi) Alzheimer's therapies including, for example, donepezil, memantine, tacrine, and equivalents and pharmaceutically active isomer(s) and/or metabolite(s) thereof;
(vii) Parkinson's therapies including, for example, deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;
(viii) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, and zomitriptan, and equivalents and pharmaceutically active isomer(s) and/or metabolite(s) thereof;
(ix) stroke therapies including, for example, abciximab, activase, NXY-059, citicoline, crobenetine, desmoteplase, repinotan, traxoprodil, and equivalents and pharmaceutically active isomer(s) and/or metabolite(s) thereof;
(x) urinary incontinence therapies including, for example, darafenacin, falvoxate, oxybutynin, propiverine, robalzotan, solifenacin, and tolterodine, and equivalents and pharmaceutically active isomer(s) and/or metabolite(s) thereof;
(xi) neuropathic pain therapies including, for example, gabapentin, lidoderm, and pregablin, and equivalents and pharmaceutically active isomer(s) and/or metabolite(s) thereof;
(xii) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;
(xiii) insomnia therapies including, for example, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, and Zolpidem, and equivalents and pharmaceutically active isomer(s) and/or metabolite(s) thereof;
(xiv) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/or metabolite(s) thereof;
(xv) 5HT1B ligands such as, for example, compounds disclosed in WO 99/05134 and WO 02/08212;
(xvi) mGluR2 agonists;
(xvii) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;
(xviii) chemokine receptor CCR1 inhibitors; and
(xix) delta opioid agonists such as, for example, compounds disclosed in WO 97/23466 and WO 02/094794.

Such combination products employ the compounds of this invention within the dosage range described herein and the other pharmaceutically active agent within approved dosage ranges and/or the dosage such as described in the publication reference.

In a further aspect the present invention provides a combination (for example for the treatment of schizophrenia, cognitive disorders or pain) of a compound of formula (I) or a pharmaceutically acceptable salt thereof as hereinbefore defined and one or more agents selected from carbamazepine, olanzapine, quetiapine, verapamil, lamotrigine, oxcarbazepine, risperidone, aripiprazole, ziprasidone and lithium.

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, and instructions for the simultaneous, sequential or separate administration of the preparations to a patient in need thereof.

The present invention will now be further explained by reference to the following illustrative examples.

The methods used for synthesis of the compounds of the invention are illustrated by the general schemes below and the preparative examples that follow. The starting materials and reagents used in preparing these compounds are available from commercial suppliers. These general schemes are merely illustrative of methods by which the compounds of this invention can be synthesised, and various modifications to these schemes can be made and will be suggested to one skilled in the art having referred to this disclosure.

Nuclear magnetic resonance (NMR) spectra were recorded at 400 MHz; the chemical shifts ($\delta$) are reported in parts per million. Spectra were recorded using a Bruker 400 Avance instrument fitted with a 5 mm BBFO probe or DUL probe. Instrument control was by Bruker TopSpin 2.1 software, unless stated otherwise.

Purity was assessed using UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of acetonitrile or methanol mixed with water containing either 0.05% formic acid or 0.025% ammonia.

Mass spectra were recorded with a Waters SQD single quadrupole mass spectrometer using atmospheric pressure ionisation, unless stated otherwise.

Compounds were purified using normal phase chromatography on silica or alumina, or by reverse phase chromatographic methods, using Biotage or Isolute KPNH Cartridge, SCX cartridge and SCX-2 solid phase extraction cartridges.

Preparative High Performance Liquid Chromatography (HPLC) was performed using an Agilent Technologies 1100 Series system typically using Waters 19 mm id×100 mm long C18 columns such as XBridge or SunFire 5 μm materials at 20 mL/min. Mobile phases typically consisted of acetonitrile or methanol mixed with water containing either 0.1% formic acid or 0.1% ammonia, unless stated otherwise.

In the following descriptions "room temperature" denotes a temperature in the range from 20° C. to 25° C.

The abbreviations used in the specific examples have the following meanings:
DMSO Dimethyl sulfoxide
DMSO-$d_6$ Deuterated dimethyl sulfoxide
MeOH-d Deuterated methanol
MeOH Methanol
MS Mass spectrum
NMR Nuclear magnetic resonance
$Pd_2(DBA)_3$ Tris(dibenzylideneacetone)dipalladium(O)
$MgSO_4$ Magnesium sulphate
XANTPHOS 4,5-Bis(diphenylphosphino)-9,9-dimethylxanthene
DBU 2,3,4,6,7,8,9,10-Octahydropyrimido[1,2-a]azepine
$CHCl_3$ Trichloromethane
$CDCl_3$ Deuterated trichloromethane
$CD_2Cl_2$ Deuterated dichloromethane
MTBE Methyl tert-butyl ether
THF Tetrahydrofuran
$CO_2$ Carbon dioxide

1. INTERMEDIATES

Scheme 1:

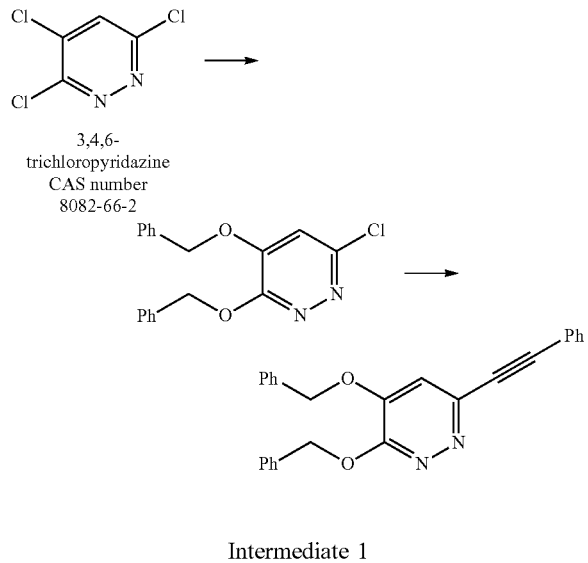

Intermediate 1

3,4-bis(Benzyloxy)-6-chloropyridazine

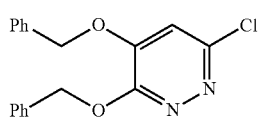 [SMILES: Clc1cc(OCc2ccccc2)c(OCc2ccccc2)nn1]

Phenylmethanol (6.72 g, 62.2 mmol) was added dropwise to a suspension of sodium hydride (60% suspension in mineral oil; 2.486 g, 62.2 mmol) in tetrahydrofuran (total volume: 100 ml) at room temperature. The resulting mixture was stirred for 1 hour and then cooled to 0° C. before 3,4,6-trichloropyridazine (5.7 g, 31.1 mmol) was added portionwise over 10 minutes. The reaction was then allowed to warm to room temperature and stirred for 16 hours before being poured into water and extracted with ethyl acetate (twice). The organic layer was washed with brine, dried (magnesium sulphate) and evaporated. The residue was purified by silica chromatography (eluting with 5-20% ethyl acetate in petrol containing 5% tetrahydrofuran) to yield 3,4-bis(benzyloxy)-6-chloropyridazine (4.0 g, 12.24 mmol, 39.4% yield) as the major product.

$^1$H NMR (400 MHz, DMSO-$d_6$): δ ppm 7.31-7.52 (m, 11 H) 5.51 (s, 2 H) and 5.31 (s, 2 H).

Intermediate 2

3,4-bis(Benzyloxy)-6-(phenylethynyl)pyridazine

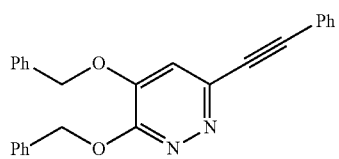 [SMILES: C(#Cc1cc(OCc2ccccc2)c(OCc2ccccc2)nn1)c1ccccc1]

A 20 ml microwave vial was charged with 3,4-bis(benzyloxy)-6-chloropyridazine (Intermediate 1; 440 mg, 1.35 mmol), DBU (1230 mg, 8.08 mmol) and ethynylbenzene (413 mgs, 4.04 mmol) in tetrahydrofuran (5 ml) to produce an orange solution. The mixture was purged with nitrogen and dichlorobis(triphenylphosphine)palladium(II) (47.3 mg, 0.067 mmol) and copper(I) iodide (25.6 mg, 0.135 mmol) were added before the whole was subjected to microwave radiation for 1 hour at 80° C. Upon cooling, the resulting mixture was diluted with ethyl acetate and washed with brine and the organic layer was purified by silica chromatography (eluting with 0-30% ethyl acetate-petrol) to yield 3,4-bis(benzyloxy)-6-(phenylethynyl)pyridazine (320 mg, 0.815 mmol, 61% yield).

$^1$H NMR (400 MHz, DMSO-$d_6$): δ 7.34-7.58 (m, 15 H), 7.06 (s, 1 H), 5.56 (s, 2 H) and 5.34 (s, 2 H).

MS ES$^+$: 393.

Intermediate 3

3,4-bis(Benzyloxy)-6-[(4-fluorophenyl)ethynyl]pyridazine

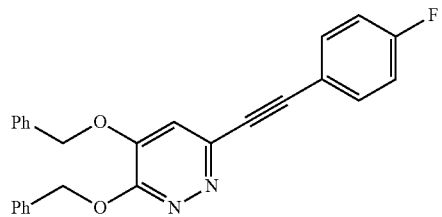 [SMILES: Fc1ccc(C#Cc2cc(OCc3ccccc3)c(OCc3ccccc3)nn2)cc1]

Prepared as described for 3,4-bis(benzyloxy)-6-(phenylethynyl)pyridazine (Intermediate 2) from 3,4-bis(benzyloxy)-6-chloropyridazine (Intermediate 1) and 1-ethynyl-4-fluorobenzene in 72% yield.

¹H NMR (400 MHz, DMSO-d₆): δ 7.67-7.76 (m, 2 H), 7.57 (s, 1 H), 7.29-7.53 (m, 12 H), 5.58 (a, 2 H) and 5.31 (s, 2 H).
MS ES⁺: 410.

Scheme 2:

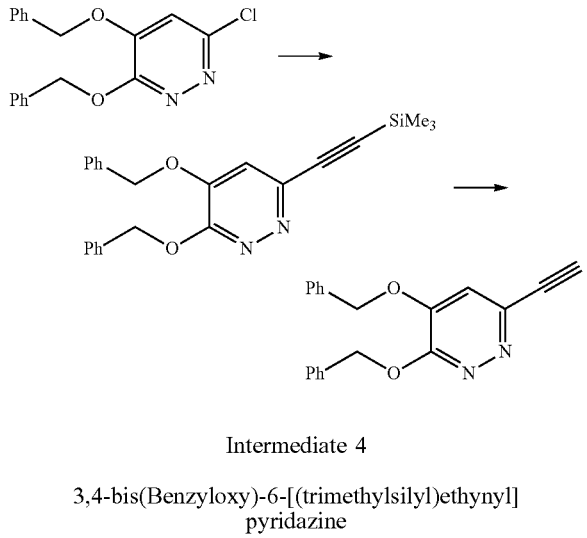

Intermediate 4

3,4-bis(Benzyloxy)-6-[(trimethylsilyl)ethynyl]pyridazine

A 20 ml microwave vial was charged with 3,4-bis(benzyloxy)-6-chloropyridazine (Intermediate 1, 3.06 mmol) and ethynyltrimethylsilane (902 mg, 9.18 mmol) in tetrahydrofuran (5 ml) to afford an orange solution. The reaction was purged with nitrogen before DBU (2.77 ml, 18.36 mmol), dichlorobis(triphenylphosphine)palladium(II) (107 mg, 0.153 mmol) and copper(I) iodide (58.3 mg, 0.306 mmol) were added and the whole was subjected to microwave radiation for 1 hour at 80° C. Upon cooling, the reaction mixture was diluted with ethyl acetate and washed with brine. The organic layer was purified by silica chromatography (eluting with 0-30% ethyl acetate in petrol) to yield 3,4-bis(benzyloxy)-6-((trimethylsilyl)ethynyl)pyridazine (838 mg, 2.16 mmol, 70% yield)
¹H NMR (400 MHz, DMSO-d₆): δ 7.08-7.28 (m, 11 H), 5.32 (s, 2 H), 5.06 (s, 2 H) and 0.08 (s, 9 H)
MS ES⁺: 389.

Intermediate 5

3,4-bis(Benzyloxy)-6-ethynylpyridazine

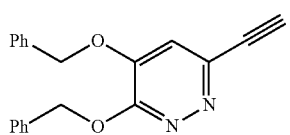 [SMILES: C#Cc1cc(OCc2ccccc2)c(OCc2ccccc2)nn1]

Potassium carbonate (295 mg, 2.136 mmol), 3,4-bis(benzyloxy)-6-((trimethylsilyl)ethynyl)pyridazine (Intermediate 4; 830 mg, 2.14 mmol) and methanol (10 ml) were added to tetrahydrofuran (5 ml) to produce an orange suspension. The mixture was stirred for 1 hour and then partitioned between brine and ethyl acetate. The organic layer was washed with brine and evaporated before the residue was purified by silica chromatography (eluting with 10-50% ethyl acetate in petrol) to yield 3,4-bis(benzyloxy)-6-ethynylpyridazine (530 mg, 1.68 mmol, 78% yield).
¹H NMR (400 MHz, DMSO-d₆): δ 7.31-7.53 (m, 11 H), 5.59 (s, 2 H), 5.30 (s, 2 H) and 4.53 (s, 1 H).
MS ES⁺: 317.

Scheme 3:

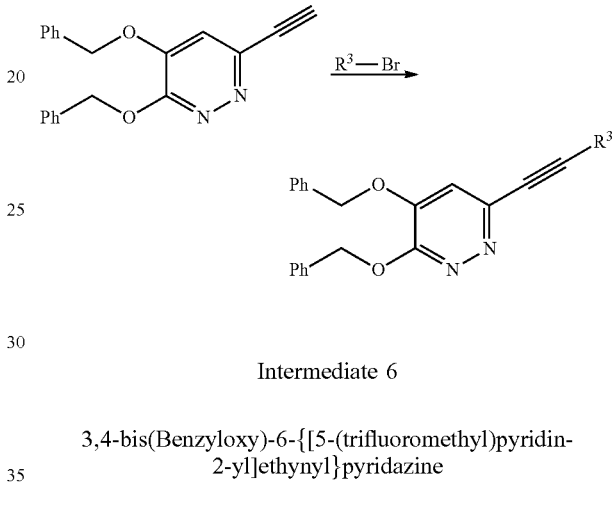

Intermediate 6

3,4-bis(Benzyloxy)-6-{[5-(trifluoromethyl)pyridin-2-yl]ethynyl}pyridazine 3,4-bis(Benzyloxy)-6-ethynylpyridazine (Intermediate 5; 530 mg, 1.68 mmol) and 2-bromo-5-(trifluoromethyl)pyridine (379 mg, 1.68 mmol) were dissolved in tetrahydrofuran (5 ml) to produce an orange solution. The reaction mixture was purged with nitrogen and then triethylamine (1.40 ml, 10.05 mmol), dichlorobis(triphenylphosphine)palladium(II) (58.8 mg, 0.08 mmol) and copper(I) iodide (31.9 mg, 0.17 mmol) were added before it was subjected to microwave irradiation for 1 hour at 80° C. Upon cooling, the mixture was diluted with ethyl acetate and washed with brine. The organic layer was concentrated in vacuo and the crude residue was then purified by silica chromatography (eluting with 0-50% ethyl acetate in petrol) to yield 3,4-bis(benzyloxy)-6-{[5-(trifluoromethyl)pyridin-2-yl]ethynyl}pyridazine (460 mg, 0.10 mmol, 60% yield).
¹H NMR (400 MHz, DMSO-d₆): δ 9.08 (s, 1 H), 8.34-8.38 (m, 1 H), 7.96-8.01 (m, 1 H), 7.70 (s 1 H), 7.33-7.53 (m, 10 H), 5.61 (s, 2 H) and 5.33 (s, 2 H).
MS ES⁺: 462.

Scheme 4:

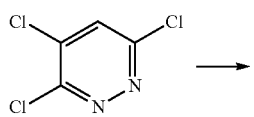

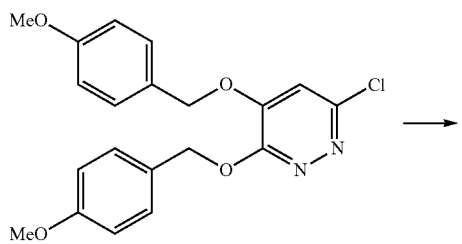

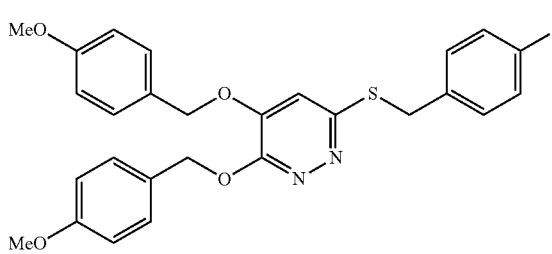

Intermediate 7

6-Chloro-3,4-bis[(4-methoxybenzyl)oxy]pyridazine

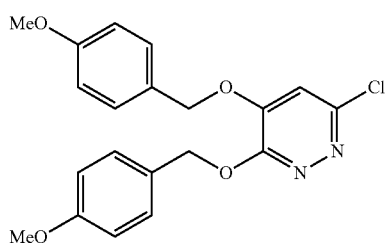 [SMILES: COc1ccc(COc2cc(Cl)nnc2OCc2ccc(OC)cc2)cc1]

To a solution of (4-methoxyphenyl)methanol (1.88 g, 13.63 mmol) in tetrahydrofuran (7.89 ml) was added a solution of potassium tert-butoxide in tetrahydrofuran (13.63 ml, 13.63 mmol). After stirring at room temperature for 1.5 hours, the mixture was cooled to 0° C. and trichloropyridazine (1.0 g, 5.45 mmol) was added portion-wise over a period of approximately 5-10 minutes. The resulting mixture was left to stir and warm to room temperature for 16 hours and then poured into water, extracted into ethyl acetate and the combined organics were dried (magnesium sulphate). The solution was then evaporated in vacuo and purified by silica chromatography (eluting with 0-40% ethyl acetate in petrol) to yield 6-chloro-3,4-bis[(4-methoxybenzyl)oxy]pyridazine (550 mg, 1.420 mmol, 26% yield).

$^1$H NMR (400 MHz, MeOH-d): δ 7.51 (s, 1 H), 7.38-7.45 (m, 4 H), 6.91-6.99 (m, 4 H), 5.39 (s, 2 H), 5.19 (s, 2 H) and 3.76 (s, 6 H).

Intermediate 8

6-[(4-Chlorobenzyl)sulfanyl]-3,4-bis[(4-methoxybenzyl)oxy]pyridazine

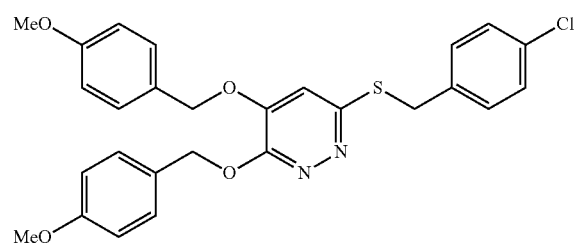 [SMILES: COc1ccc(COc2cc(SCc3ccc(Cl)cc3)nnc2OCc2ccc(OC)cc2)cc1]

A mixture of 6-chloro-3,4-bis[(4-methoxybenzyl)oxy]pyridazine (Intermediate 7; 550 mg, 1.42 mmol), (4-chlorophenyl)methanethiol (248 mg, 1.56 mmol), Pd$_2$(DBA)$_3$ (52.1 mg, 0.057 mmol), XANTPHOS (65.8 mg, 0.114 mmol) and Hunig's base (ethyl diisopropylamine; 404 mg, 3.13 mmol) was subjected to microwave irradiation at 120° C. for 1 hour. The resulting mixture was poured into water and extracted into ethyl acetate before the combined organics were washed with brine and then dried (magnesium sulphate). The resulting solution was evaporated in vacuo and purified by silica chromatography (eluting with 0-40% dichlormethane in petrol) to yield 6-[(4-chlorobenzyl)sulfanyl]-3,4-bis[(4-methoxybenzyl)oxy]pyridazine (201 mg, 1.42 mmol, 28% yield).

$^1$H NMR (400 MHz, MeOH-d): δ 7.25-7.48 (m, 8 H), 6.88-6.95 (m, 4 H), 5.42 (s, 2 H), 5.08 (s, 2 H), 4.41 (s, 2 H) and 3.83 (s, 6 H).

MS ES$^+$: 509.

Intermediate 9

3,4-bis(Benzyloxy)-6-{[6-(trifluoromethyl)pyridin-3-yl]ethynyl}pyridazine

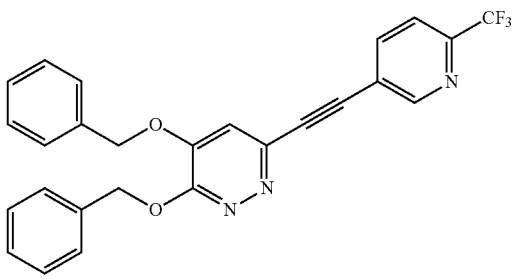 [SMILES: FC(F)(F)c1ccc(C#Cc2cc(OCc3ccccc3)c(OCc3ccccc3)nn2)cn1]

A microwave vial was charged with 5-iodo-2-(trifluoromethyl)pyridine (617 mg, 2.260 mmol), copper(I) iodide (39.1 mg, 0.205 mmol), bis(triphenylphosphine)palladium(II)

chloride (72.1 mg, 0.103 mmol), 1,8-diazabicycloundec-7-ene (DBU; 1858 μl, 12.33 mmol) and tetrahydrofuran (6849 μl). The reaction mixture was then purged and evacuated with nitrogen and to this was then added 3,4-bis(benzyloxy)-6-ethynylpyridazine (Intermediate 5: 650 mg, 2.1 mmol). The reaction was heated to 80° C. whilst being subjected to microwave radiation for 1 hour. Upon cooling the reaction mixture was partitioned between ethyl acetate and water, at which point a solid formed which was filtered and discarded. The organics were then washed with water and brine, dried (MgSO$_4$), filtered and concentrated to afford a brown oil. This was purified by silica chromatography (elating with 0-100% ethyl acetate in petrol) to yield 3,4-bis(benzyloxy)-6-{[6-(trifluoromethyl)pyridin-3-yl]ethynyl}pyridazine as a yellow amorphous solid (yield=10%)

MS ES$^+$: 462.

Intermediate 10

3,4-bis(Benzyloxy)-6-[(3-fluorophenyl)ethynyl]pyridazine

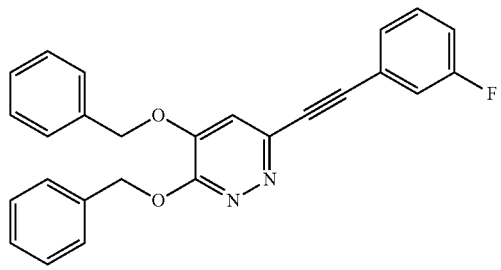 [SMILES: Fc1cccc(C#Cc2cc(OCc3ccccc3)c(OCc3ccccc3)nn2)c1]

Prepared as described for 3,4-bis(benzyloxy)-6-(phenylethynyl)pyridazine (Intermediate 2) from 3,4-bis(benzyloxy)-6-chloropyridazine (Intermediate 1) and 1-ethynyl-3-fluorobenzene.

$^1$H NMR (400 MHz, DMSO-d$_6$): δ7.32-7.64 (m, 15 H), 5.56 (s, 2 H) and 5.30 (s, 2 H).

MS ES$^+$: 411.

Intermediate 11

3,4-bis(Benzyloxy)-6-[(2-fluorophenyl)ethynyl]pyridazine

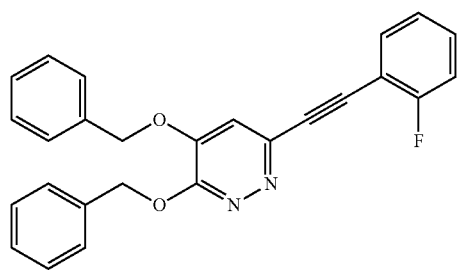 [SMILES: Fc1ccccc1C#Cc1cc(OCc2ccccc2)c(OCc2ccccc2)nn1]

Prepared as described for 3,4-bis(benzyloxy)-6-(phenylethynyl)pyridazine (Intermediate 2) from 3,4-bis(benzyloxy)-6-chloropyridazine (Intermediate 1) and 1-ethynyl-2-fluorobenzene.

$^1$H NMR (400 MHz, DMSO-d$_6$): δ 7.63-7.76 (m, 1 H), 7.58 (s, 2 H), 7.30-7.50 (m, 12 H), 5.59 (s, 2 H) and 5.32 (s, 2 H).

MS ES$^+$: 411.

Intermediate 12

3,4-bis(Benzyloxy)-6-[(3,5-difluorophenyl)ethynyl]pyridazine

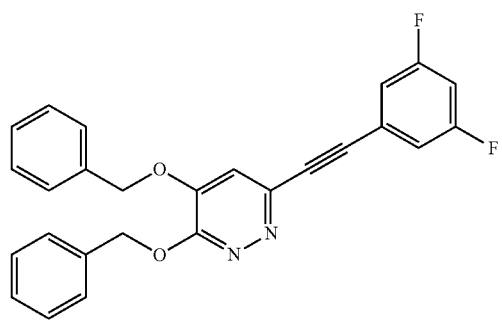 [SMILES: Fc1cc(F)cc(C#Cc2cc(OCc3ccccc3)c(OCc3ccccc3)nn2)c1]

Prepared as described for 3,4-bis(benzyloxy)-6-(phenylethynyl)pyridazine (Intermediate 2) from 3,4-bis(benzyloxy)-6-chloropyridazine (Intermediate 1) and 1-ethynyl-3,5-difluorobenzene.

$^1$H NMR (400 MHz, DMSO-d$_6$): δ 7.63 (s, 1 H), 7.32-7.52 (s, 13 H), 5.59 (s, 2 H) and 5.30 (s, 2 H).

MS ES$^+$:429.

Intermediate 13

3,4-bis(Benzyloxy)-6-[2-(3,4-difluoropbenyl)ethynyl]pyridazine

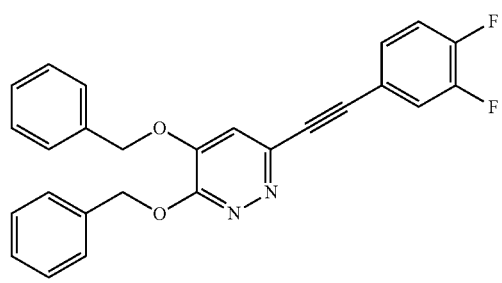 [SMILES: Fc1ccc(C#Cc2cc(OCc3ccccc3)c(OCc3ccccc3)nn2)cc1F]

Prepared as described for 3,4-bis(benzyloxy)-6-(phenylethynyl)pyridazine (Intermediate 2) from 3,4-bis(benzyloxy)-6-chloropyridazine (Intermediate 1) and 1-ethynyl-3,4-difluorobenzene.

$^1$H NMR (400 MHz, DMSO-d$_6$): δ 7.52-7.67 (s, 1 H), 7.36-7.59 (a, 13 H), 5.58 (s, 2 H) and 5.31 (s, 2 H).

MS ES$^+$: 429.

Intermediate 14

3,4-bis(Benzyloxy)-6-{2-[3-(trifluoromethoxy)phenyl]-ethynyl}pyridazine

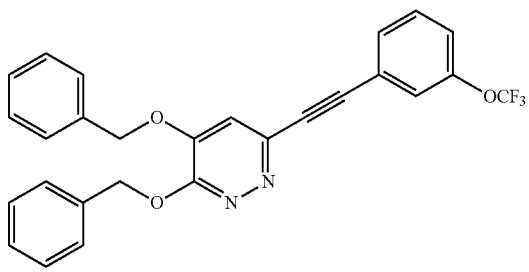 [SMILES: FC(F)(F)Oc1cccc(C#Cc2cc(OCc3ccccc3)c(OCc3ccccc3)nn2)c1]

Prepared as described for 3,4-bis(benzyloxy)-6-(phenyl-ethynyl)pyridazine (Intermediate 2) from 3,4-bis(benzyloxy)-6-chloropyridazine (Intermediate 1) and 1-ethynyl-3-trifluoromethoxybenzene (prepared as described in Published International Patent Application No. WO 2005/94822, see Preparation 28).

$^1$H NMR (400 MHz, DMSO-$d_6$): δ 7.60-7.75 (m, 3 H), 7.31-7.57 (s, 12 H), 5.58 (s, 2 H) and 5.28 (s, 2 H).

MS ES$^+$: 477.

Intermediate 15

3,4-bis(Benzyloxy)-6-{2-[3-(trifluoromethyl)phenyl]-ethynyl}pyridazine

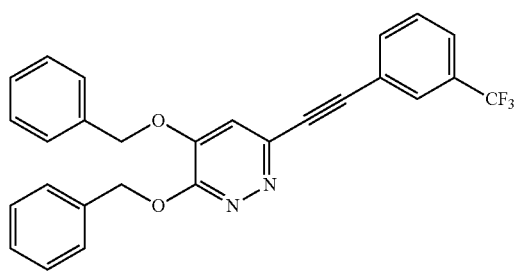 [SMILES: FC(F)(F)c1cccc(C#Cc2cc(OCc3ccccc3)c(OCc3ccccc3)nn2)c1]

Prepared as described for 3,4-bis(benzyloxy)-6-{[6-(trifluoromethyl)pyridin-3-yl]ethynyl}pyridazine (Intermediate 9) from 3,4-bis(benzyloxy)-6-ethynylpyridazine (Intermediate 5) and 1-iodo-3-(trifluoromethyl)benzene.

$^1$H NMR (400 MHz, DMSO-$d_6$): δ 8.01 (s, br, 1 H), 7.96 (d, J=7.83 Hz, 1 H), 7.87 (d, J=7.93 Hz, 1 H), 7.70-7.77 (m, 1 H), 7.64 (s, 1 H), 7.29-7.52 (m, 10 H), 5.59 (s, 2 H), 5.31 (s, 2 H).

MS ES$^+$: 461.

Intermediate 16

3,4-bis(Benzyloxy)-6-{2-[5-(trifluoromethyl)pyridin-3-yl]ethynyl}pyridazine

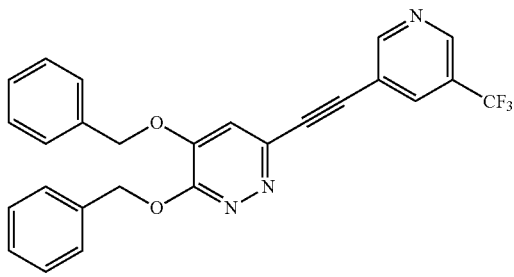 [SMILES: FC(F)(F)c1cncc(C#Cc2cc(OCc3ccccc3)c(OCc3ccccc3)nn2)c1]

Prepared as described for 3,4-bis(benzyloxy)-6-{[6-trifluoromethyl)pyridin-3-yl]ethynyl}pyridazine (Intermediate 9) from 3,4-bis(benzyloxy)-6-ethynylpyridazine (Intermediate 5) and 3-bromo-5-trifluoromethylpyridine.

MS ES$^+$: 462.

Intermediate 17

3,4-bis(Benzyloxy)-6-(cyclohexylethynyl)pyridazine

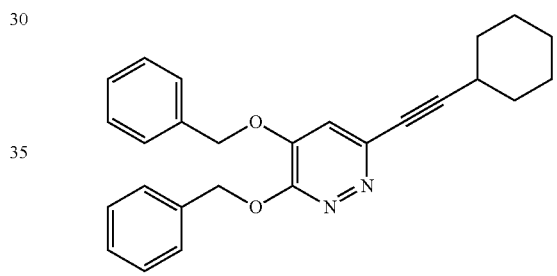

Prepared as described for 3,4-bis(benzyloxy)-6-(phenyl-ethynyl)pyridazine (Intermediate 2) from 3,4-bis(benzyloxy)-6-chloropyridazine (Intermediate 1) and ethynylcyclohexane.

$^1$H NMR (400 MHz, CD$_2$Cl$_2$) δ 7.54-7.56 (m, 2 H), 7.33-7.48 (m, 8 H), 6.92 (s, 1 H), 5.63 (s, 2 H), 5.17 (s, 2 H), 2.61-2.73 (m, 1H), 1.90-2.00 (m, 2 H), 1.75-1.84 (m, 2 H), 1.52-1.67 (m, 4 H), 1.35-1.46 (m, 2 H).

MS ES$^+$: 399.

Intermediate 18

3,4-bis(Benzyloxy)-6-(cyclopropylethynyl)pyridazine

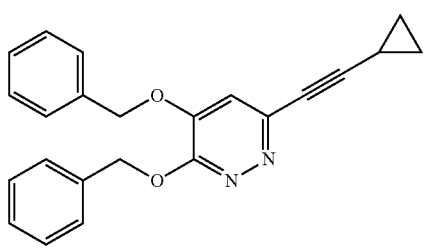 [SMILES: C(#CC1CC1)c1cc(OCc2ccccc2)c(OCc2ccccc2)nn1]

Prepared as described fat 3,4-bis(benzyloxy)-6-(phenylethynyl)pyridazine (Intermediate 2) from 3,4-bis(benzyloxy)-6-chloropyridazine (Intermediate 1) and ethynylcyclopropane.

$^1$H NMR (400 MHz, DMSO-d$_6$) δ 7.14-7.55 (m, 11 H), 5.53 (s, 2 H), 5.25 (s, 2 H), 1.57-1.67 (m, 1 H), 0.92-0.99 (m, 2 H), 0.77-0.84 (m, 2 H).

MS ES$^+$: 357.

Intermediate 19

3,4-bis(Benzyloxy)-6-(cyclopentylethynyl)pyridazine

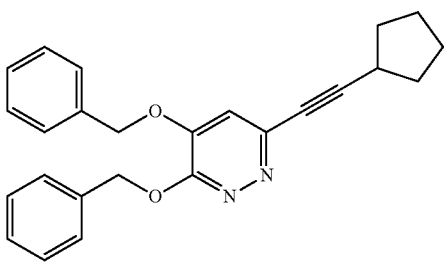 [SMILES: C(#CC1CCCC1)c1cc(OCc2ccccc2)c(OCc2ccccc2)nn1]

Prepared as described for 3,4-bis(benzyloxy)-6-(phenylethynyl)pyridazine (Intermediate 2) from 3,4-bis(benzyloxy)-6-chloropyridazine (Intermediate 1) and ethynylcyclopentane.

$^1$H NMR (400 MHz, CD$_2$Cl$_2$) δ 7.28-7.55 (m, 10 H), 6.82-6.90 (m, 1 H), 5.57 (s, 2 H), 5.14 (s, 2 H), 2.79-2.94 (m, 1 H), 1.97-2.13 (m, 2 H), 1.49-1.86 (m, 6 H)

MS ES$^+$: 385.

Intermediate 20

3,4-bis(Benzyloxy)-6-[(4-methoxycyclohex-1-en-1-yl)ethynyl]pyridazine

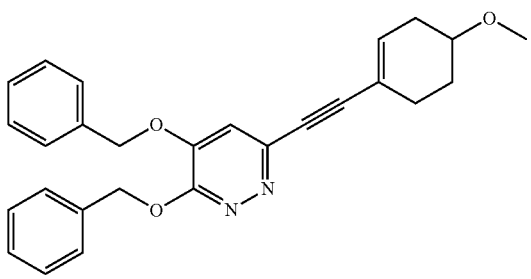 [SMILES: COC1CC=C(C#Cc2cc(OCc3ccccc3)c(OCc3ccccc3)nn2)CC1]

A microwave reaction vial was charged with 4-methoxycyclohex-1-enyl trifluoromethanesulfonate (1069 mg, 4.11 mmol), copper(I) iodide (16.83 mg, 0.09 mmol), tetrakis(triphenylphosphine)palladium(0) (54.6 mg, 0.05 mmol), triethylamine (1432 μl, 10.27 mmol) and dry N,N-dimethylformamide (6849 μl). The reaction was evacuated and purged with nitrogen and a solution of 3,4-bis(benzyloxy)-6-ethynylpyridazine (Intermediate 5; 650 mg, 2.06 mmol) in dry tetrahydrofuran (3 ml) was added before the whole was then stirred in the microwave at 70° C. for 1 hour. Upon cooling, the resulting mixture was partitioned between ethyl acetate and water and the organic extracts were washed with water and brine, dried (MgSO$_4$), filtered and concentrated to afford a brown oil. This was purified by chromatography on silica eluting with 0-75% ethyl acetate in petrol to give 3,4-bis(benzyloxy)-6-[(4-methoxycyclohex-1-en-1-yl)ethynyl]pyridazine (Intermediate 20) as a brown oil (860 mg, 85%).

$^1$H NMR (400 MHz, CD$_2$Cl$_2$) δ 7.28-7.57 (m, 10 H), 6.90 (s, 1 H), 6.22 (br s, 1 H), 5.60 (s, 2 H), 5.14 (a, 2 H), 3.45-3.55 (m, 1 H), 3.31-3.38 (m, 3 H), 2.10-2.56 (m, 4 H), 1.88-1.97 (m, 1 H), 1.64-1.78 (m, 1 H)

MS ES$^+$: 427.

Intermediate 21

3,4-bis(Benzyloxy)-6-[(2,4-difluorophenyl)ethynyl]pyridazine

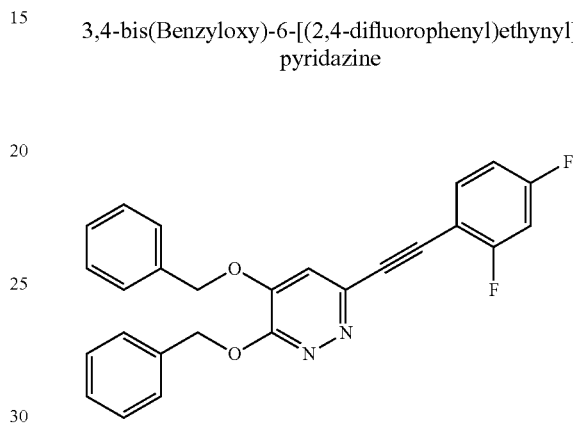

Prepared as described for 3,4-bis(benzyloxy)-6-(phenylethynyl)pyridazine (Intermediate 2) from 3,4-bis(benzyloxy)-6-chloropyridazine (Intermediate 1) and 1-ethynyl-2,4-difluorobenzene.

$^1$H NMR (400 MHz, CD$_2$Cl$_2$) δ 7.49-7.67 (m, 3 H), 7.31-7.51 (m, 8 H), 6.85-7.07 (m, 3 H), 5.70 (s, 2 H), 5.23 (s, 2 H).

MS ES$^+$: 429.

Intermediate 22

3,4-bis(Benzyloxy)-6-{[3-(difluoromethyl)phenyl]ethynyl}pyridazine

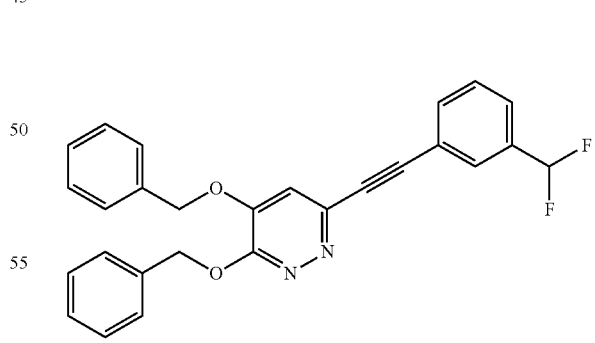

Prepared as described for 3,4-bis(benzyloxy)-6-{[6-(trifluoromethyl)pyridin-3-yl]ethynyl}pyridazine (Intermediate 9) from 3,4-bis(benzyloxy)-6-ethynylpyridazine (Intermediate 5) and 3-bromo-5-difluoromethylpyridine.

$^1$H NMR (400 MHz, CDCl$_3$) δ 7.65-7.85 (m, 2 H), 7.21-7.65 (m, 12 H), 6.99 (s, 1 H), 6.40-6.90 (m, 1 H, CHF$_2$), 5.70 (s, 2 H), 5.24 (s, 2 H).

MS ES$^+$: 443.

Intermediate 23

6-Benzyl-3,4-bis(benzyloxy)pyridazine

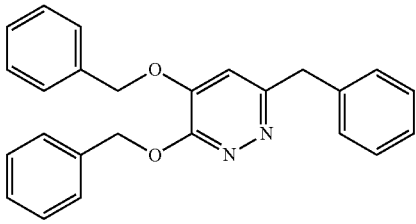 [SMILES: c1ccc(COc2cc(Cc3ccccc3)nnc2OCc2ccccc2)cc1]

To a solution of 3,4-bis(benzyloxy)-6-chloropyridazine (Intermediate 1: 0.22 g, 0.67 mmol) in tetrahydrofuran (6 ml) and water (0.6 ml) was added cesium carbonate (0.66 g, 2.01 mmol) and [1,1'-bis(diphenylphosphino)ferrocene]dichloropalladium(II) (0.049 g, 0.067 mmol). The reaction was then purged and evacuated with nitrogen several times before 9-benzyl-9-borabicyclo[3.3.1]nonane (9-BBN; 4.02 ml, 2.01 mmol) was added. The reaction vessel was then sealed and heated to 60° C. for 1 hour. Upon cooling, the resulting mixture was diluted with ethyl acetate and washed 5 times with a 1:1 mixture of water and saturated aqueous brine. The organics portion was dried (MgSO$_4$), filtered and concentrated to give an orange oil. The crude oil was purified by silica chromatography (eluting with 0-80% ethyl acetate in petrol) to yield 6-benzyl-3,4-bis(benzyloxy)pyridazine as a colourless oil (yield=64%).

$^1$H NMR (400 MHz, CDCl$_3$) δ 7.56 (d, J=7.33 Hz, 2 H), 7.12-7.48 (m, 13 H), 6.55 (s, 1 H), 5.64 (s, 2 H), 5.08 (s, 2 H), 4.17 (s, 2 H).

MS ES$^+$: 383.

Intermediate 24

3,4-bis(Benzyloxy)-6-((3-chlorophenyl)ethynyl)pyridazine

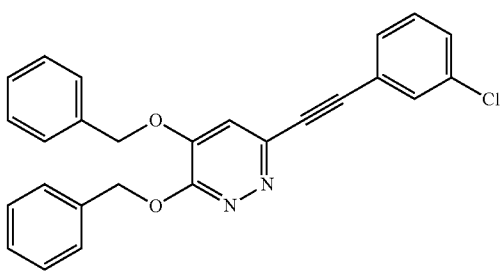 [SMILES: Clc1cccc(C#Cc2cc(OCc3ccccc3)c(OCc3ccccc3)nn2)c1]

To a solution of 1-chloro-3-iodobenzene (0.862 g, 3.62 mmol) in dry tetrahydrofuran (11 ml) was added copper(I) iodide (0.063 g, 0.33 mmol), bis(triphenylphosphine)-palladium(II) chloride (0.115 g, 0.16 mmol) and 1,8-diazabicycloundec-7-ene and (DBU; 2.97 ml, 19.72 mmol). The reaction was then purged and evacuated with nitrogen several times before 3,4-bis(benzyloxy)-6-ethynylpyridazine (Intermediate 5; 1.04 g, 3.29 mmol) was added. The reaction vessel was sealed and heated to 80° C. for 1 hour. Upon cooling, the resultant mixture was partitioned between ethyl acetate and water. The combined organic portions were washed with water (×2) and brine, dried (MgSO$_4$), filtered and concentrated to give a brown oil. The crude oil was purified by silica chromatography (eluting with 0-20% ethyl acetate in petrol) to yield 3,4-bis(benzyloxy)-6-((3-chlorophenyl)ethynyl)pyridazine as a yellow solid (yield=30%).

$^1$H NMR (400 MHz, CDCl$_3$) δ 7.21-7.65 (m, 14 H), 6.97 (s, 1 H), 5.70 (s, 2 H), 5.23 (s, 2 H).

MS ES$^+$: 427/429.

Intermediate 25

3,4-bis(Benzyloxy)-6-(1-phenylethenyl)pyridazine

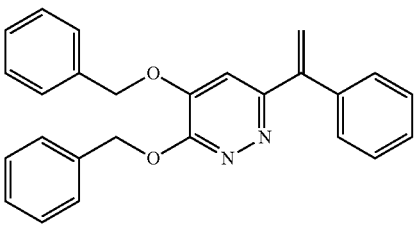 [SMILES: C=C(c1ccccc1)c1cc(OCc2ccccc2)c(OCc2ccccc2)nn1]

A mixture of 3,4-bis(benzyloxy)-6-chloropyridazine (Intermediate 1: 3 g, 9.18 mmol), dioxane (32.1 ml) and water (9.64 ml) was degassed and to this was added mono(bis(di-tert-butyl(4-(dimethylamino)phenyl)phosphonio)palladium (IV)) dichloride (0.195 g, 0.275 mmol), cesium carbonate (10.14 g, 31.1 mmol) and 4,4,5,5-tetramethyl-2-(1-phenylethenyl)-1,3,2-dioxaborolane (3 g, 13.04 mmol). The mixture was heated to 80° C. for 6 hours and upon cooling was partitioned between dichloromethane and water. The organic portion was dried (MgSO$_4$), filtered and concentrated to give an orange oil. The crude oil was purified by silica chromatography eluting with 0-60% ethyl acetate in petrol to afford 3,4-bis(benzyloxy)-6-(1-phenylethenyl)pyridazine as a brown oil (yield=91%).

$^1$H NMR (400 MHz, CHCl$_3$-d) δ 7.54-7.66 (m, 2 H), 7.24-7.44 (m, 13 H), 6.72 (s, 1H), 6.02 (s, 1H), 5.70 (s, 2H), 5.63 (s, 1H), 5.11 (s, 2H).

MS ES$^+$: 395.

Intermediate 26

3,4-bis(Benzyloxy)-6-(1-phenylcyclopropyl)pyridazine

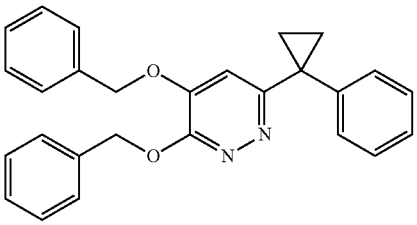 [SMILES: c1ccc(COc2cc(C3(c4ccccc4)CC3)nnc2OCc2ccccc2)cc1]

To a suspension of sodium hydride (0.487 g, 12.17 mmol, 60% in mineral oil) in DMSO (33.8 ml) stirring under nitrogen was added trimethyl sulfoxonium iodide (2.68 g, 12.17 mmol) in 4 portions over 20 minutes. A solution of 3,4-bis(benzyloxy)-6-(1-phenylethenyl)pyridazine (Intermediate 25; 3.2 g, 8.11 mmol) in tetrahydrofuran (50.7 ml) was added via a dropping funnel over 90 minutes before the reaction was left to stir at room temperature for 18 hours. The resulting mixture was concentrated, poured into ice water and extracted with ethyl acetate (×3). The organics portion was dried (MgSO$_4$), filtered and concentrated to give a brown oil. The crude oil was purified by silica chromatography (eluting with 0-50% ethyl acetate in petrol) to yield 3,4-bis(benzyloxy)-6-(1-phenylcyclopropyl)pyridazine as a yellow oil (yield=23%).

$^1$H NMR (400 MHz, CHCl$_3$-d) δ 7.47-7.63 (m, 2 H), 7.22-7.46 (m, 11 H), 7.10-7.25 (m, 2 H), 6.40 (s, 1 H), 5.62 (s, 2 H), 4.97 (s, 2 H), 1.71-1.85 (m, 2 H), 1.25-1.38 (m, 2 H).

MS ES$^+$: 409.

Scheme 5a:

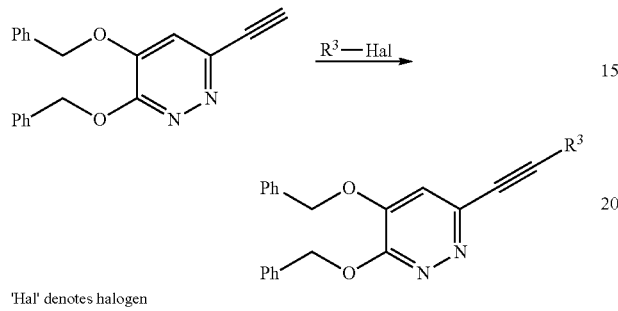

'Hal' denotes halogen

Intermediate 27

4-{2-[5, 6-bis(Benzyloxy)pyridazin 3-yl]ethynyl}benzonitrile

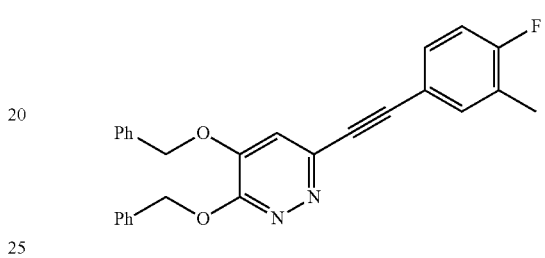

Prepared as described for 3,4-bis(benzyloxy)-6-{[5-(trifluoromethyl)pyridin-2-yl]ethynyl}pyridazine (Intermediate 6) from 3,4-bis(benzyloxy)-6-ethynylpyridazine (Intermediate 5) and 4-iodobenzonitrile in 73% yield.

$^1$H NMR (400 MHz, CD$_2$Cl$_2$) δ 7.67-7.81 (m, 4 H), 7.32-7.65 (m, 10 H), 7.08 (s, 1 H), 5.68 (s, 2 H) and 5.23 (s, 2 H).

MS ES$^+$: 418.

Intermediate 28

3,4-bis(Benzyloxy)-6-[2-(3-fluoro-4-methylphenyl)-ethynyl]pyridazine

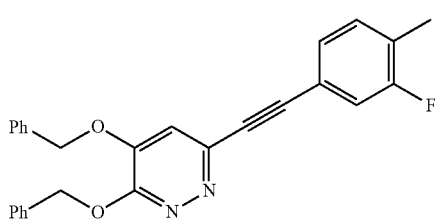 [SMILES: Cc1ccc(C#Cc2cc(OCc3ccccc3)c(OCc3ccccc3)nn2)cc1F]

Prepared as described for 3,4-bis(benzyloxy)-6-{[5-(trifluoromethyl)pyridin-2-yl]ethynyl}pyridazine (Intermediate 6) from 3,4-bis(benzyloxy)-6-ethynylpyridazine (Intermediate 5) and 2-fluoro-4-iodo-1-methylbenzene in 67% yield.

Intermediate 29

3,4-bis(Benzyloxy)-6-[2-(4-fluoro-3-methylphenyl)-ethynyl]pyridazine

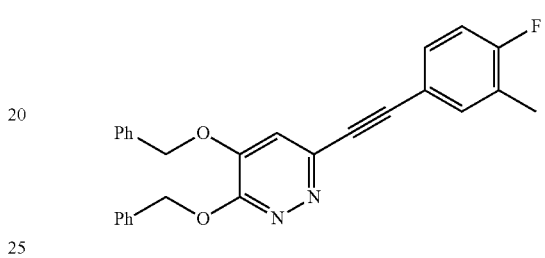

Prepared as described for 3,4-bis(benzyloxy)-6-{[5-(trifluoromethyl)pyridin-2-yl]ethynyl}pyridazine (Intermediate 6) from 3,4-bis(benzyloxy)-6-ethynylpyridazine (Intermediate 5) and 1-fluoro-4-iodo-2-methylbenzene in 67% yield.

$^1$H NMR (400 MHz, CD$_2$Cl$_2$) δ 7.29-7.58 (m, 12 H), 6.99-7.08 (m, 2H), 5.62 (s, 2 H), 5.17 (s, 2 H) and 2.29 (s, 3 H).

MS ES$^+$: 425.

Intermediate 30

3,4-bis(Benzyloxy)-6-[2-(3,4-dimethoxyphenyl) ethynyl]pyridazine

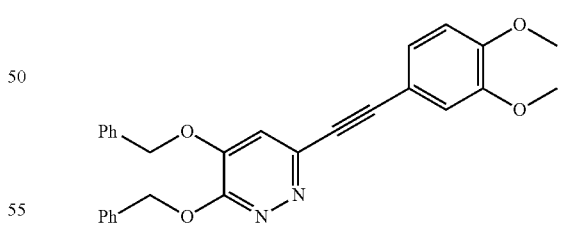

Prepared as described for 3,4-bis(benzyloxy)-6-{[5-(trifluoromethyl)pyridin-2-yl]ethynyl}pyridazine (Intermediate 6) from 3,4-bis(benzyloxy)-6-ethynylpyridazine (Intermediate 5) and 4-iodo-1,2-dimethoxybenzene in 17% yield.

$^1$H NMR (400 MHz, CDCl$_3$) δ 7.52-7.61 (m, 2 H), 7.33-7.47 (m, 8 H), 7.18-7.26 (m, 1 H), 7.09-7.15 (m, 1 H), 6.97 (s, 1 H), 6.87 (m, 1 H), 5.69 (s, 2 H), 5.22 (s, 2 H) and 3.89-3.96 (m, 6 H).

MS ES$^+$: 453.

Intermediate 31

3,4-bis(Benzyloxy)-6-{2-[5-(trifluoromethyl)pyridin-3-yl]ethynyl}pyridazine

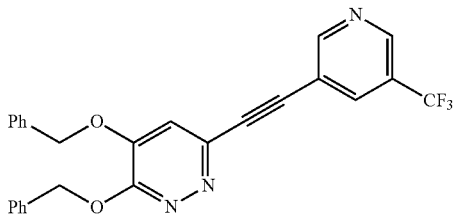 [SMILES: FC(F)(F)c1cncc(C#Cc2cc(OCc3ccccc3)c(OCc3ccccc3)nn2)c1]

Prepared as described for 3,4-bis(benzyloxy)-6-{[5-(trifluoromethyl)pyridin-2-yl]ethynyl}pyridazine (Intermediate 6) from 3,4-bis(benzyloxy)-6-ethynylpyridazine (Intermediate 5) and 3-bromo-5-(trifluoromethyl)pyridine in 31% yield.

MS ES$^+$: 462.

Intermediate 32

3,4-bis(Benzyloxy)-[2-(2-chloro-6-fluorophenyl)ethynyl]pyridazine

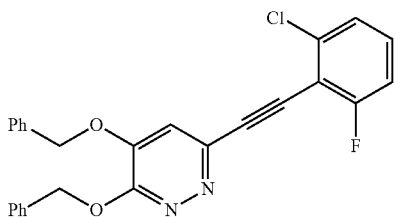 [SMILES: Fc1cccc(Cl)c1C#Cc1cc(OCc2ccccc2)c(OCc2ccccc2)nn1]

Prepared as described for 3,4-bis(benzyloxy)-6-{[5-(trifluoromethyl)pyridin-2-yl]ethynyl}pyridazine (Intermediate 6) from 3,4-bis(benzyloxy)-6-ethynylpyridazine (Intermediate 5) and 1-chloro-3-fluoro-2-iodobenzene.

MS ES$^+$: 445.

Intermediate 33

3,4-bis(Benzyloxy)-6-[2-(2,6-difluorophenyl)ethynyl]pyridazine

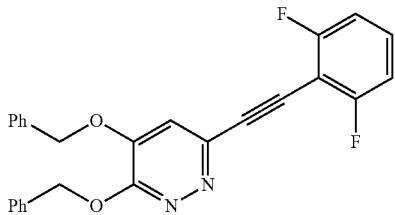

Prepared as described for 3,4-bis(benzyloxy)-6-{[5-(trifluoromethyl)pyridin-2-yl]ethynyl}pyridazine (Intermediate 6) from 3,4-bis(benzyloxy)-6-ethynylpyridazine (Intermediate 5) and 2-bromo-1,3-difluorobenzene.

MS ES$^+$: 429.

Intermediate 34

3,4-bis(Benzyloxy)-6-[2-(4-chlorophenyl)ethynyl]pyridazine

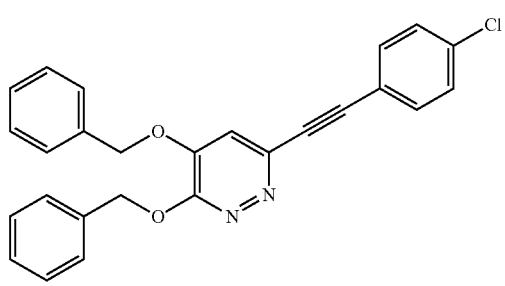 [SMILES: Clc1ccc(C#Cc2cc(OCc3ccccc3)c(OCc3ccccc3)nn2)cc1]

Prepared as described for 3,4-bis(benzyloxy)-6-{[5-(trifluoromethyl)pyridin-2-yl]ethynyl}pyridazine (intermediate 6) from 3,4-bis(benzyloxy)-6-ethynylpyridazine (Intermediate 5) and 1-chloro-4-iodobenzene in 70% yield.

$^1$H NMR (400 MHz, DMSO-d$_6$) δ 7.22-7.75 (m, 15 H), 5.45-5.68 (m, 2 H) and 5.30 (s, 2 H).

MS ES$^+$: 427.

Intermediate 35

3,4-bis(Benzyloxy)-6-[2-(2-2-chlorophenyl)ethynyl]pyridazine

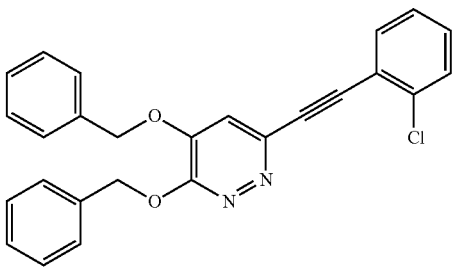 [SMILES: Clc1ccccc1C#Cc1cc(OCc2ccccc2)c(OCc2ccccc2)nn1]

Prepared as described for 3,4-bis(benzyloxy)-6-{[5-(trifluoromethyl)pyridin-2-yl]ethynyl}pyridazine (intermediate 6) from 3,4-bis(benzyloxy)-6-ethynylpyridazine (Intermediate 5) and 1-chloro-2-iodobenzene in 59% yield.

$^1$H NMR (400 MHz, DMSO-d$_6$) δ 7.72-7.81 (m, 1 H), 7.61-7.68 (m, 1 H), 7.29-7.58 (m, 13 H), 5.58 (s, 2 H) and 5.32 (s, 2 H).

MS ES$^+$: 427 and 429.

Intermediate 36

3,4-bis(Benzyloxy)-6-{2-[4-(difluoromethoxy)phenyl]-ethynyl}pyridazine

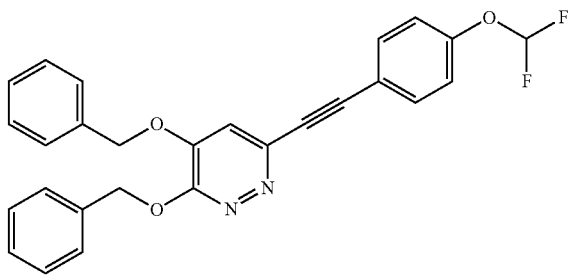 [SMILES: FC(F)Oc1ccc(C#Cc2cc(OCc3ccccc3)c(OCc3ccccc3)nn2)cc1]

Prepared as described for 3,4-bis(benzyloxy)-6-{[5-(trifluoromethyl)pyridin-2-yl]ethynyl}pyridazine (intermediate 6) from 3,4-bis(benzyloxy)-6-ethynylpyridazine (Intermediate 5) and 1-(difluoromethoxy)-4-iodobenzene in 58% yield.
$^1$H NMR (400 MHz, CD$_2$Cl$_2$) δ 7.60-7.69 (m, 2 H), 7.49-7.55 (m, 2 H), 7.32-7.48 (m, 8 H), 7.12-7.20 (m, 2 H), 7.03 (s, 1 H), 6.39-6.81 (m, 1 H), 5.63 (s, 2 H) and 5.14-5.22 (m, 2 H).
MS ES$^+$: 459.

Intermediate 37

3,4-bis(Benzyloxy)-6-{2-[4-(trifluoromethoxy)phenyl]-ethynyl}pyridazine

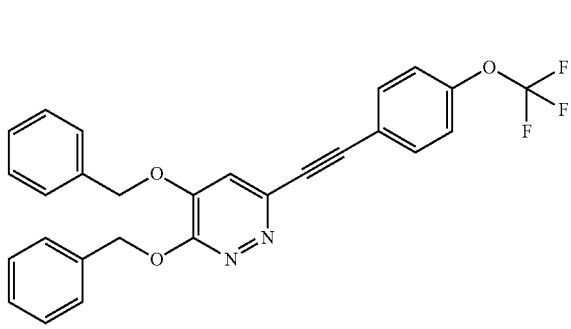 [SMILES: FC(F)(F)Oc1ccc(C#Cc2cc(OCc3ccccc3)c(OCc3ccccc3)nn2)cc1]

Prepared as described for 3,4-bis(benzyloxy)-6-{[5-(trifluoromethyl)pyridin-2-yl]ethynyl}pyridazine (Intermediate 6) from 3,4-bis(benzyloxy)-6-ethynylpyridazine (Intermediate 5) and 1-iodo-4-(trifluoromethoxy)benzene.
MS ES$^+$: 477.

Intermediate 38

3,4-bis(Benzyloxy)-6-{2-[3-(difluoromethoxy)phenyl]-ethynyl}pyridazine

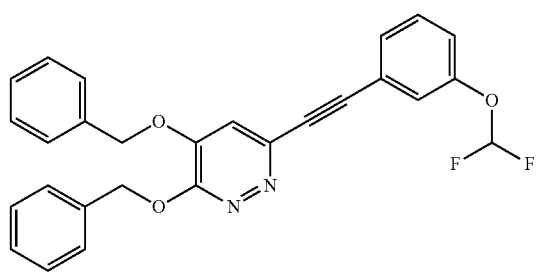 [SMILES: FC(F)Oc1cccc(C#Cc2cc(OCc3ccccc3)c(OCc3ccccc3)nn2)c1]

Prepared as described for 3,4-bis(benzyloxy)-6-{[5-(trifluoromethyl)pyridin-2-yl]ethynyl}pyridazine (Intermediate 6) from 3,4-bis(benzyloxy)-6-ethynylpyridazine (Intermediate 5) and 1-(difluoromethoxy)-3-iodobenzene in 87% yield.
$^1$H NMR (400 MHz, CD$_2$Cl$_2$) δ 7.29-7.56 (m, 13 H), 7.14-7.23 (m, 1 H), 6.39-6.79 (m, 1 H), 5.63 (s, 2 H) and 5.19 (s, 2H).
MS ES$^+$: 459.

Scheme 5b:

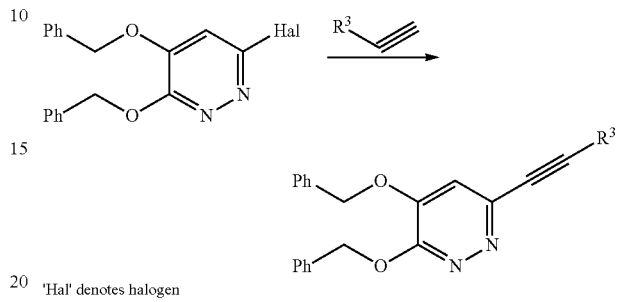

'Hal' denotes halogen

Intermediate 39

3,4-bis(Benzyloxy)-6-{2-(3-(trifluoromethoxy)phenyl)-ethynyl}pyridazine

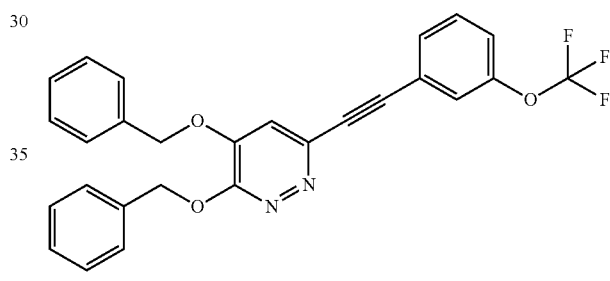

Prepared as described for 3,4-bis(benzyloxy)-6-(phenylethynyl)pyridazine (Intermediate 2) from 3,4-bis(benzyloxy)-6-chloropyridazine (Intermediate 1) and 1-ethynyl-3-(trifluoromethoxy)benzene in 37% yield.
$^1$H NMR (400 MHz, DMSO-d$_6$) δ 7.25-7.79 (m, 15 H), 5.59 (s, 2 H) and 5.25-5.34 (m, 2 H).
MS ES$^+$: 477.

Intermediate 40

3,4-bis(Benzyloxy)-6-{2-[2-(trifluoromethyl)phenyl]-ethynyl}pyridazine

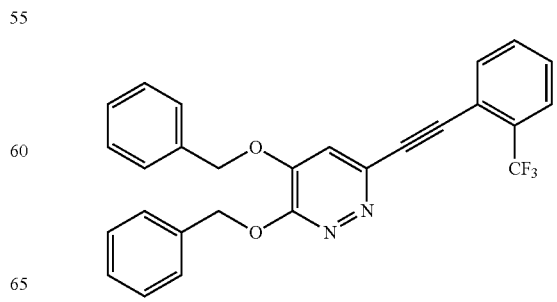

Prepared as described for 3,4-bis(benzyloxy)-6-(phenylethynyl)pyridazine (Intermediate 2) from 3,4-bis(benzyloxy)-6-chloropyridazine (Intermediate 1) and 1-ethynyl-2-(trifluoromethyl)benzene in quantitative yield.

¹H NMR (400 MHz, DMSO-d₆) δ 7.86-7.94 (m, 2 H), 7.76-7.83 (m, 1 H), 7.67-7.74 (m, 1 H), 7.28-7.54 (m, 11 H), 5.59 (s, 2 H) and 5.30-5.37 (m, 2 H).

MS ES⁺: 461.

Scheme 6:

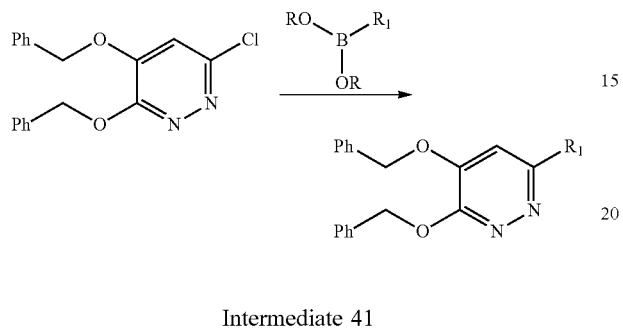

Intermediate 41

3,4-bis(Benzyloxy)-6-[1-(4-fluorophenyl)ethenyl]pyridazine

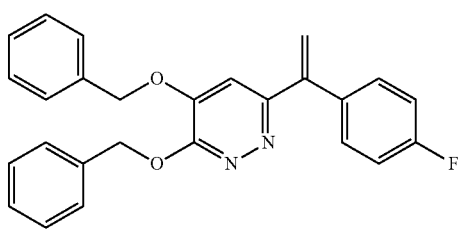 [SMILES: C=C(c1ccc(F)cc1)c1cc(OCc2ccccc2)c(OCc2ccccc2)nn1]

Prepared as described for 3,4-bis(benzyloxy)-6-(1-phenylethenyl)pyridazine (Intermediate 25) from 3,4-bis(benzyloxy)-6-chloropyridazine (Intermediate 1) and 2-(1-(4-fluorophenyl)ethenyl)-4,4,5,5-tetramethyl-1,3,2-dioxaborolane in 92% yield.

¹H NMR (400 MHz, CD₂Cl₂) δ 7.54-7.64 (m, 2 H), 7.18-7.46 (m, 10 H), 6.94-7.07 (m, 2 H), 6.71 (s, 1 H), 5.95 (s, 1 H), 5.70 (s, 2 H), 5.59 (s, 1 H) and 5.14 (s, 2 H)

MS ES⁺: 413.

Intermediate 42

3,4-bis(Benzyloxy)-6-[1-(4-fluorophenyl)cyclopropyl]pyridazine

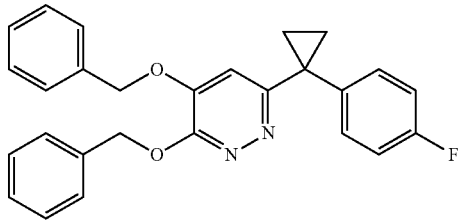 [SMILES: Fc1ccc(C2(c3cc(OCc4ccccc4)c(OCc4ccccc4)nn3)CC2)cc1]

Prepared as described for 3,4-bis(benzyloxy)-6-(1-phenylcyclopropyl)pyridazine (Intermediate 26) from 3,4-bis(benzyloxy)-6-(1-phenylethenyl)pyridazine (Intermediate 41) in 16% yield.

¹H NMR (400 MHz, CDCl₃) δ 7.48-7.60 (m, 2 H), 7.14-7.45 (m, 10 H), 6.95-7.07 (m, 2 H), 6.33 (s, 1 H), 5.62 (s, 2 H), 5.01 (s, 2 H), 1.73-1.82 (m, 2 H) and 1.22-1.34 (m, 2 H).

MS ES⁺: 427.

Intermediate 43

3,4-bis(Benzyloxy)-6-{1-[3-(trifluoromethyl)phenyl]-ethenyl}pyridazine

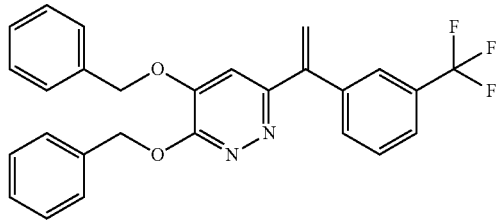 [SMILES: C=C(c1cccc(C(F)(F)F)c1)c1cc(OCc2ccccc2)c(OCc2ccccc2)nn1]

Prepared as described for 3,4-bis(benzyloxy)-6-(1-phenylethenyl)pyridazine (Intermediate 25) from 3,4-bis(benzyloxy)-6-chloropyridazine (Intermediate 1) and 4,4,5,5-tetramethyl-2-(1-(3-(trifluoromethyl)phenyl)ethenyl)-1,3,2-dioxaborolane in 45% yield.

MS ES⁺: 463.

4,4,5,5-Tetramethyl-2-(1(3-(trifluoromethyl)phenyl)ethenyl)-1,3,2-dioxaborolane was prepared as follows A flask was charged with (1,3-bis(2,6-diisopropylphenyl)-2,3-dihydro-1H-imidazol-2-yl)copper(II) chloride (0,675 g, 138 mmol), sodium tert-butoxide (0.133 g, 1.38 mmol) and THF (100 ml) and stirred under nitrogen for 0 minutes. Bis(pinacolato)diborane (7.72 g, 30.4 mmol) was added to the solution and the mixture was stirred at room temperature for 30 minutes. The mixture was cooled to −78° C. and a solution of 1-ethynyl-3-(trifluoromethyl)benzene (4.7 g, 27.6 mmol) in THF (20 ml) and MeOH (1.23 ml, 30.4 mmol) were added via syringe. The flask was then stirred at −40° C. (Acetonitrile/CO₂ bath) overnight. Reaction was at room temperature in the morning. The reaction was cooled to −78° C. and then filtered through a pad of silica and diatomaceous earth (sold under the trade mark "Celite") to give a brown solution which was concentrated and the residue was purified by silica chromatography eluting with 0-5% Et₂O/Petrol to yield 4,4,5,5-tetramethyl-2-(1-(3-(trifluoromethyl)phenyl)ethenyl)-1,3,2-dioxaborolane (2.15 g, 26%)

¹H NMR (400 MHz, Chloroform-d) δ 7.74 (s, 1H), 7.63-7.70 (m, 1H), 7.48-7.53 (m, 1H), 7.40-7.47 (m, 1H), 6.09-6.20 (m, 2H), 1.34 (s, 12H)

Intermediate 44

3,4-bis(Benzyloxy)-6-[(E)-2-[4-(trifluoromethyl)phenyl]-ethenyl]pyridazine

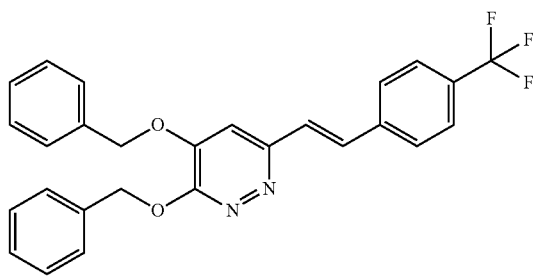 [SMILES: FC(F)(F)c1ccc(/C=C/c2cc(OCc3ccccc3)c(OCc3ccccc3)nn2)cc1]

A microwave vial was charged with 3,4-bis(benzyloxy)-6-chloropyridazine (Intermediate 1) (5 g, 15.30 mmol), (E)-4-(trifluoromethyl)styrylboronic acid (4.96 g, 22.95 mmol), potassium carbonate (7.40 g, 53.6 mmol) and tetrakis(triphenyl phosphine)palladium(0) (0.530 g, 0.459 mmol). The reaction was evacuated and purged with nitrogen before dioxane (3.40 ml) was added and the whole was heated under vacuum. Water (1.7 ml) was then added and the reaction mixture heated at 120° C. under microwave irradiation for 1 hour. The reaction mixture was diluted with ethyl acetate and washed with water and then brine and the combined organics were dried (MgSO$_4$) and concentrated in vacuo to give the desired compound as an orange solid (5.6 g, 79%),
$^1$H NMR (400 MHz, DMSO-d$_6$) δ 7.85-7.94 (m, 2 H), 7.65-7.82 (m, 4 H), 7.28-7.55 (m, 11 H), 5.57 (s, 2 H) and 5.33 (s, 2 H).
MS ES$^+$: 463.

Scheme 7:

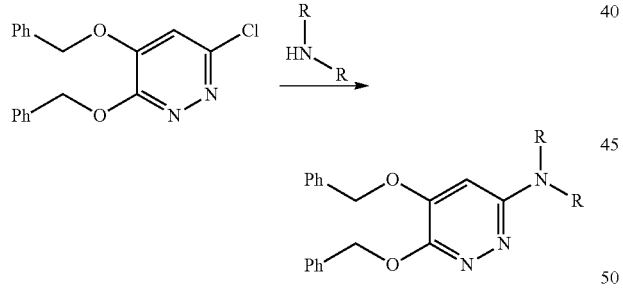

Intermediate 45

5,6-bis(Benzyloxy)-N-(4-fluorophenyl)methyl-pyridazin-3-anine

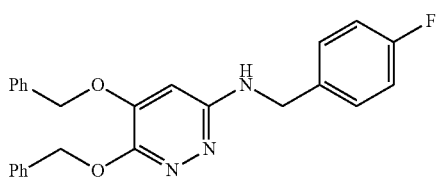 [SMILES: Fc1ccc(CNc2cc(OCc3ccccc3)c(OCc3ccccc3)nn2)cc1]

3,4-Bis(benzyloxy)-6-chloropyridazine (Intermediate 1) (1 g, 3.1 mmol), [1,1'-bis(di-tert-butylphosphino)ferrocene]palladium(II) dichloride (0.100 g, 0.15 mmol) and sodium tert-butoxide (0.59 g, 6.1 mmol) were added to dioxane (10.2 ml). The resulting mixture was purged with nitrogen before 4-fluorobenzylamine (78 mg, 6.1 mmol) was added. The mixture was heated at 120° C. for 1 hour under microwave irradiation. Upon cooling the crude mixture was quenched with water and extracted with ethyl acetate before the organic extracts were dried (MgSO$_4$) and concentrated in vacuo. The residue was purified by column chromatography on silica eluting with 0-100% ethyl acetate/petrol to yield the title compound.
MS ES$^+$: 416.

Intermediate 46

5,6-bis(Benzyloxy)-N-(cyclopropylmethyl)-N-methylpyridazin-3-amine

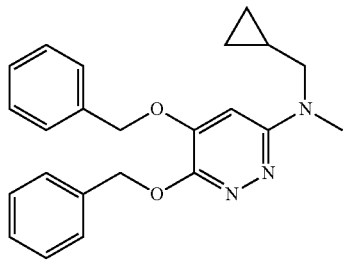 [SMILES: CN(CC1CC1)c1cc(OCc2ccccc2)c(OCc2ccccc2)nn1]

Prepared as described for 5,6-bis(benzyloxy)-N-[(4-fluorophenyl)methyl]pyridazin-3-amine (Intermediate 45) from 3,4-bis(benzyloxy)-6-chloropyridazine (Intermediate 1) and 1-cyclopropyl-N-methylmethanamine in 17% yield.
$^1$H NMR (400 MHz, CD$_2$Cl$_2$) δ 7.25-7.53 (m, 10 H), 6.29 (s, 1 H), 5.45 (s, 2 H), 5.15 (s, 2 H), 3.28-3.37 (m, 2 H), 3.07 (s, 3 H), 0.91-1.03 (m, 1 H), 0.41-0.53 (m, 2 H) and 0.14-0.27 (m, 2 H).
MS ES$^+$: 376.

Intermediate 47

5,6-bis(Benzyloxy)-N-(cyclohexylmethyl)-N-methylpyridazin-3-amine

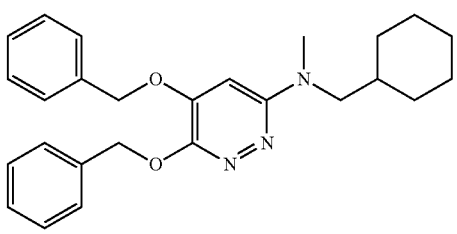 [SMILES: CN(CC1CCCCC1)c1cc(OCc2ccccc2)c(OCc2ccccc2)nn1]

Prepared as described for 5,6-bis(benzyloxy)-N-[(4-fluorophenyl)methyl]pyridazin-3-amine (Intermediate 45) from 3,4-bis(benzyloxy)-6-chloropyridazine (Intermediate 1) and 1-cyclohexyl-N-methylmethanamine in 26% yield.

$^1$H NMR (400 MHz, CD$_2$Cl$_2$) δ 7.27-7.50 (m, 10 H), 6.17 (s, 1 H), 5.43 (s, 2 H), 5.15 (s, 2 H), 3.14-3.20 (m, 2 H), 3.01 (s, 3 H) and 1.07-1.76 (m, 11 H).
MS ES$^+$: 418.

Scheme 8:

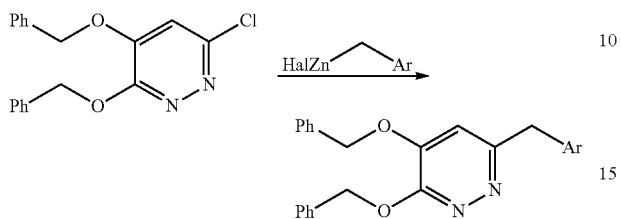

'Hal' denotes halogen; Ar denotes an aromatic moiety

Intermediate 48

3,4-bis(Benzyloxy)-6-[(3-chlorophenyl)methyl]pyridazine

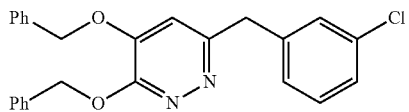 [SMILES: Clc1cccc(Cc2cc(OCc3ccccc3)c(OCc3ccccc3)nn2)c1]

To a stirred solution of 3,4-bis(benzyloxy)-6-chloropyridazine (Intermediate 1) (1 g, 3.1 mmol) in dry tetrahydrofuran (12.2 nil) was added tetrakis(triphenylphosphine)palladium(0) (0.18 g, 0.153 mmol) and (3-chlorobenzyl)zinc(II) chloride (9.2 ml of a 0.5 M solution in tetrahydrofuran, 4.6 mmol). The reaction was stirred at 60° C. for 17 hours and then partitioned between ethyl acetate and water. The organic extracts were washed with water and brine and then dried, filtered and concentrated to give a yellow oil. The oil was purified using 0-70% ethyl acetate in petrol to afford the title compound (310 mg, 23%),
$^1$H NMR (400 MHz, CD$_2$Cl$_2$) δ 7.47-7.55 (m, 2 H), 7.29-7.44 (m, 8 H), 7.19-7.28 (m, 3 H), 7.09-7.17 (m, 1 H), 6.57-6.63 (m, 1 H), 5.57 (s, 2 H), 5.04-5.12 (m, 2 H) and 4.09-4.15 (m, 2 H).
MS ES$^+$: 417.

Intermediate 49

3,4-bis(Benzyloxy)-6-[(4-chlorophenyl)methyl]pyridazine

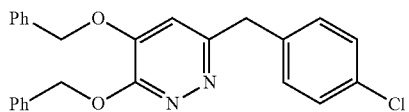 [SMILES: Clc1ccc(Cc2cc(OCc3ccccc3)c(OCc3ccccc3)nn2)cc1]

Prepared as described for 3,4-bis(benzyloxy)-6-[(3-chlorophenyl)methyl]pyridazine (Intermediate 48) from 3,4-bis(benzyloxy)-6-chloropyridazine (Intermediate 1) and (4-chlorobenzyl)zinc(II) chloride in 95% yield.
$^1$H NMR (400 MHz, CD$_2$Cl$_2$) δ 7.47-7.55 (m, 2 H), 7.23-7.43 (m, 10 H), 7.12-7.19 (m, 2 H), 6.56 (s, 1 H), 5.56 (s, 2 H), 5.04-5.10 (m, 2 H) and 4.02-4.16 (m, 2 H).
MS ES$^+$: 417.

Intermediate 50

3,4-bis(Benzyloxy)-6-(cyclohexylmethyl)pyridazine

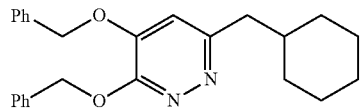 [SMILES: c1ccc(COc2cc(CC3CCCCC3)nnc2OCc2ccccc2)cc1]

To a solution of 3,4-bis(benzyloxy)-6-chloropyridazine (Intermediate 1) (1 g, 3.06 mmol) and bis(tri-tert-butylphosphine)palladium (0.063 g, 0.122 mmol) in N-methylpyrrolidine (30.0 ml) under nitrogen was added (cyclohexylmethyl)zinc(II) bromide (0.5 M in tetrahydrofuran) (12.24 ml, 6.12 mmol) and the resulting brown mixture was stirred at room temperature overnight and then heated at 100° C. for 2 hours. The reaction mixture was then allowed to cool, diluted with ethyl acetate and washed with saturated aqueous sodium bicarbonate solution, saturated aqueous ammonium chloride solution and brine. The organics were dried (MgSO$_4$), filtered and solvent removed in vacuo to give a brown oil. The oil was purified by silica chromatography (eluting with 0-30% ethyl acetate in petrol) to yield the title compound (540 mg, 1.39 mmol, 45% yield).
$^1$H NMR (400 MHz, CDCl$_3$) δ 7.50-7.61 (m, 2 H), 7.30-7.45 (m, 8 H), 6.56 (s, 1 H), 5.62 (s, 2 H), 5.20 (s, 2 H), 2.61-2.69 (m, 2 H), 1.53-1.76 (m, 7 H), 1.10-1.23 (m, 2 H) and 0.84-1.04 (m, 2H).
MS ES$^+$: 389, Intermediate 51

3,4-bis(Benzyloxy)-6-[(4-fluorophenyl)methyl]pyridazine

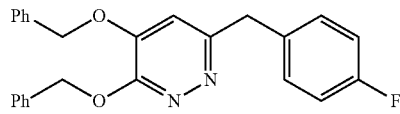 [SMILES: Fc1ccc(Cc2cc(OCc3ccccc3)c(OCc3ccccc3)nn2)cc1]

To a solution of 3,4-bis(benzyloxy)-6-chloropyridazine (Intermediate 1) (1 g, 3.06 mmol), dicyclohexyl(2',4',6'-triisopropylbiphenyl-2-yl)phosphine (0.117 g, 0.245 mmol) and palladium (II) acetate (0.027 g, 0.122 mmol) in tetrahydrofuran (6.12 ml) under nitrogen was added (4-fluorobenzyl)zinc(II) bromide (9.18 ml, 4.59 mmol) and the resulting red/brown mixture was heated at 65° C. for 24 hours. The reaction mixture was cooled, diluted with ethyl acetate and washed with saturated aqueous sodium bicarbonate solution, saturated ammonium chloride solution and brine. The organics were dried (MgSO$_4$), filtered and solvent removed in vacuo to give a brown oil. The oil was purified by silica chromatography (eluting with 0-100% ethyl acetate in petrol) to yield the title compound (663 n mg, 1.61 mmol, 97% yield).
$^1$H NMR (400 MHz, CDCl$_3$) δ 7.49-7.60 (m, 2 H), 7.23-7.44 (m, 8 H), 7.11-7.20 (m, 2 H), 6.92-7.02 (m 2 H), 6.48 (s, 1 H), 5.62 (s, 2 H), 5.08 (s, 2 H) and 4.07-4.20 (m, 2 H).

MS ES+: 401.

Intermediate 52

3,4-bis(Benzyloxy)-6-[(2-chloro-6-fluorophenyl)methyl]pyridazine

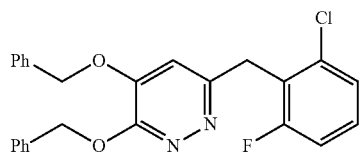 [SMILES: Fc1cccc(Cl)c1Cc1cc(OCc2ccccc2)c(OCc2ccccc2)nn1]

Prepared as described for 3,4-bis(benzyloxy)-6-[(4-fluorophenyl)methyl]pyridazine (Intermediate 51) from 3,4-bis(benzyloxy)-6-chloropyridazine (Intermediate 1) and (2-chloro-6-fluorobenzyl)zinc(II) chloride in 23% yield.

$^1$H NMR (400 MHz, CDCl$_3$) δ 7.45-7.58 (m, 2 H), 7.12-7.43 (m, 10 H), 6.96-7.08 (m, 1 H), 6.60 (s, 1 H), 5.61 (s, 2 H), 5.12 (s, 2 H) and 4.34 (s, 2 H),

MS ES+: 435.

Intermediate 53

3,4-bis(Benzyloxy)-6-[(2-chlorophenyl)methyl]pyridazine

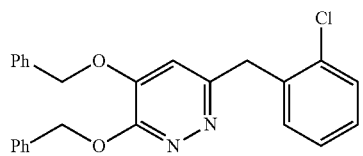 [SMILES: Clc1ccccc1Cc1cc(OCc2ccccc2)c(OCc2ccccc2)nn1]

Prepared as described for 3,4-bis(benzyloxy)-6-[(4-fluorophenyl)methyl]pyridazine (Intermediate 51) from 3,4-bis(benzyloxy)-6-chloropyridazine (Intermediate 1) and (2-chlorobenzyl)zinc(II) chloride in 38% yield.

$^1$H NMR (400 MHz, CDCl$_3$) δ 7.48-7.62 (m, 2 H), 7.15-7.45 (m, 12 H), 6.62 (s, 1 H), 5.62 (s, 2 H), 5.11 (s, 2 H) and 4.29 (s, 2 H).

MS ES+: 417.

Intermediate 54

3,4-bis(Benzyloxy)-6-[(3-fluorophenyl)methyl]pyridazine

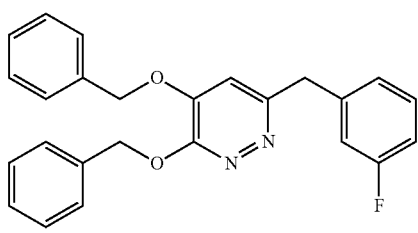 [SMILES: Fc1cccc(Cc2cc(OCc3ccccc3)c(OCc3ccccc3)nn2)c1]

Prepared as described for 3,4-bis(benzyloxy)-6-[(4-fluorophenyl)methyl]pyridazine (Intermediate 51) from 3,4-bis(benzyloxy)-6-chloropyridazine (Intermediate 1) and (3-fluorobenzyl)zinc(II) chloride in 32% yield.

$^1$H NMR (400 MHz, DMSO-d$_6$) δ 66.99-7.55 (m, 15 H), 5.43-5.58 (m, 2 H), 5.18-5.31 (m, 2 H) and 4.08-4.17 (m, 2H)

MS ES+: 401.

Intermediate 55

3,4-bis(Benzyloxy)-6-[(2-fluorophenyl)methyl]pyridazine

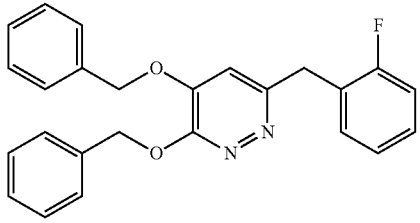 [SMILES: Fc1ccccc1Cc1cc(OCc2ccccc2)c(OCc2ccccc2)nn1]

Prepared as described for 3,4-bis(benzyloxy)-6-((4-fluorophenyl)methyl)pyridazine (Intermediate 51) from 3,4-bis(benzyloxy)-6-chloropyridazine (Intermediate 1) and (2-fluorobenzyl)zinc(II) chloride in 77% yield.

$^1$H NMR (400 MHz, DMSO-d$_6$) δ 7.23-7.51 (m, 12 H), 7.09-7.23 (m, 3 H), 5.48 (s, 2 H), 5.14-5.29 (m, 2 H) and 4.13 (s, 2H).

MS ES+: 401.

Intermediate 56

3,4-bis(Benzyloxy)-6-[(4-methylphenyl)methyl]pyridazine

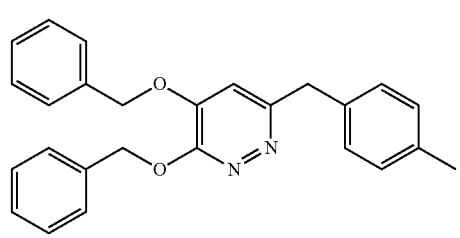 [SMILES: Cc1ccc(Cc2cc(OCc3ccccc3)c(OCc3ccccc3)nn2)cc1]

Prepared as described for 3,4-bis(benzyloxy)-6-[(4-fluorophenyl)methyl]pyridazine (Intermediate 51) from 3,4-bis(benzyloxy)-6-chloropyridazine (Intermediate 1) and (4-methylbenzyl)zinc(II) chloride in 45% yield.

$^1$H NMR (400 MHz, DMSO-d$_6$) δ 7.05-7.50 (m, 15 H), 5.48 (s, 2 H), 5.18 (s, 2 H), 3.99-4.07 (m, 2 H) and 2.23-2.28 (m, 3 H).

MS ES+: 397.

Intermediate 57

3,4-bis(Benzyloxy)-6-[(3-methylphenyl)methyl]pyridazine

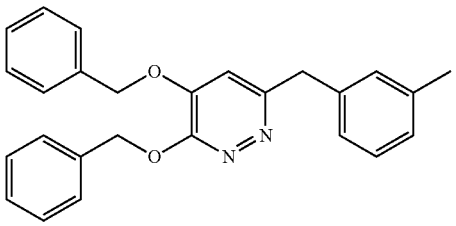 [SMILES: Cc1cccc(Cc2cc(OCc3ccccc3)c(OCc3ccccc3)nn2)c1]

Prepared as described for 3,4-bis(benzyloxy)-6-[(4-fluorophenyl)methyl]pyridazine (Intermediate 51) from 3,4-bis(benzyloxy)-6-chloropyridazine (Intermediate 1) and (3-methylbenzyl)zinc(II) chloride in 66% yield.

$^1$H NMR (400 MHz, DMSO-d$_6$) δ 7.00-7.50 (m, 15 H), 5.31-5.62 (m, 2 H), 5.11-5.25 (m, 2 H), 3.97-4.14 (m, 2 H) and 2.21-2.29 (m, 3H).

MS ES$^+$: 397.

Intermediate 58

3,4-bis(Benzyloxy)-6-{[3-(trifluoromethyl)phenyl]methyl}pyridazine

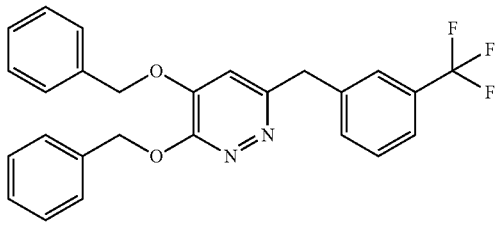 [SMILES: FC(F)(F)c1cccc(Cc2cc(OCc3ccccc3)c(OCc3ccccc3)nn2)c1]

Prepared as described for 3,4-bis(benzyloxy)-6-[(4-fluorophenyl)methyl]pyridazine (Intermediate 51) from 3,4-bis(benzyloxy)-6-chloropyridazine (Intermediate 1) and (3-(trifluoromethyl)benzyl)zinc(II) chloride in 33% yield.

$^1$H NMR (400 MHz, CD$_2$Cl$_2$) δ ppm 7.47-7.54 (m, 4 H), 7.42-7.46 (m, 2 H), 7.29-7.42 (m, 8 H), 6.61 (s, 1 H), 5.56 (s, 2 H), 5.09 (s, 2 H) and 4.24 (br s, 2 H).

MS ES$^+$: 451.

Intermediate 58a 3,4-bis(Benzyloxy)-6-{[3,5-bis(trifluoromethyl)phenyl]-methyl}pyridazine

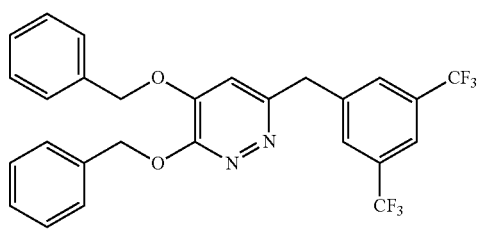 [SMILES: FC(F)(F)c1cc(Cc2cc(OCc3ccccc3)c(OCc3ccccc3)nn2)cc(C(F)(F)F)c1]

To a solution of 3,4-bis(benzyloxy)-6-chloropyridazine (Intermediate 1) (1 g, 3.06 mmol)dicyclohexyl(2',4',6'-triisopropylbiphenyl-2-yl)phosphine (0.143 g, 0.3 mmol) and palladium (II) acetate (0.034 g, 0.15 mmol) in tetrahydrofuran (10 ml) under nitrogen was added the supernatant zinc reagent [generated from the addition of 1-(chloromethyl)-3,5-bis(trifluoromethyl)benzene (3 g, 11.43 mmol) to a suspension of magnesium (0.694 g, 28.6 mmol) in lithium chloride (28.6 ml, 14.28 mmol) in tetrahydrofuran (1M) and zinc(II) chloride (12.57 ml, 12.57 mmol) in tetrahydrofuran, warmed to 30° C. to initiate and stirred for one hour to complete] and the resulting red/brown mixture was heated at 65° C. for 16 hours. The reaction mixture was cooled, diluted with ethyl acetate and washed with saturated aqueous sodium bicarbonate solution, saturated aqueous ammonium chloride solution and brine. The organics were dried (MgSO$_4$), filtered and solvent removed in vacuo to give a brown oil. The oil was purified by silica chromatography eluting with 0-40% ethyl acetate in petrol to yield the title compound (520 mg 33%).

$^1$H NMR (400 MHz, DMSO-d$_6$) δ 7.93-8.10 (m, 3 H), 7.23-7.53 (m, 11), 5.49 (s, 2 H), 5.23 (s, 2 H) and 4.34 (s, 2 H).

MS ES$^+$: 519.

Scheme 9:

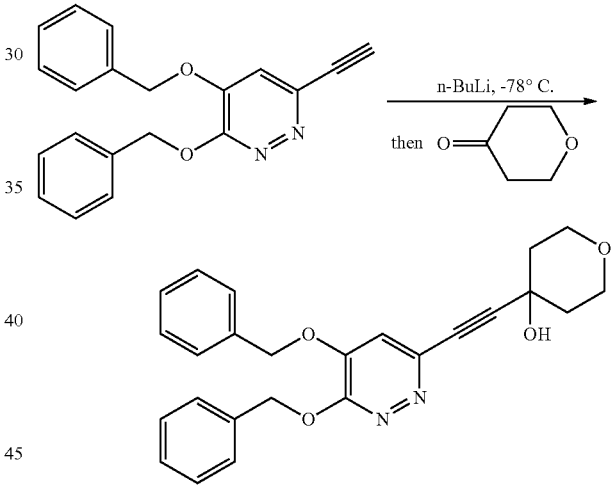

Intermediate 59

4-{2-[5, 6-bis(Benzyloxy)pyridazin-3-yl]ethynyl}oxan-4-ol

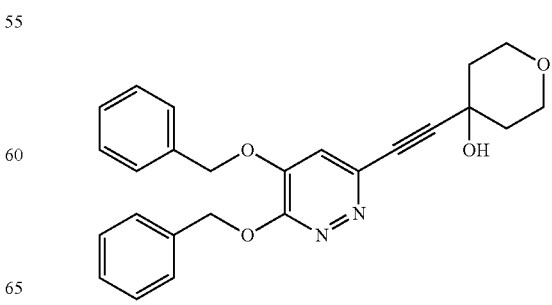

3,4-bis(Benzyloxy)-6-ethynylpyridazine (Intermediate 5; 3.0 g, 9.49 mmol) was dissolved in tetrahydrofuran (24 ml) under nitrogen atmosphere and the resulting solution was cooled to −78° C. n-Butyl lithium (23% solution in hexane; 7.92 ml, 28.48 mmol, 3.0 eq) was added slowly at −78° C. and the resulting mixture was allowed to stir for 30 minutes. Dihydro-2H-pyran-4(3H)-one (1.0 g, 10.44 mmol, 1.1 equiv.) was added slowly to reaction mass and the whole was allowed to warm to room temperature. The crude mixture was then poured into a saturated solution of aqueous ammonium chloride (300 ml) and product was extracted into ethyl acetate (100 ml×2). The organic layer was separated, washed with brine, dried (Na$_2$SO$_4$) and concentrated in vacuo. The crude product was purified by column chromatography on silica gel (eluting with 0-30% ethyl acetate in hexane) to yield the desired material (2.0 g, 501% yield).

Scheme 10:

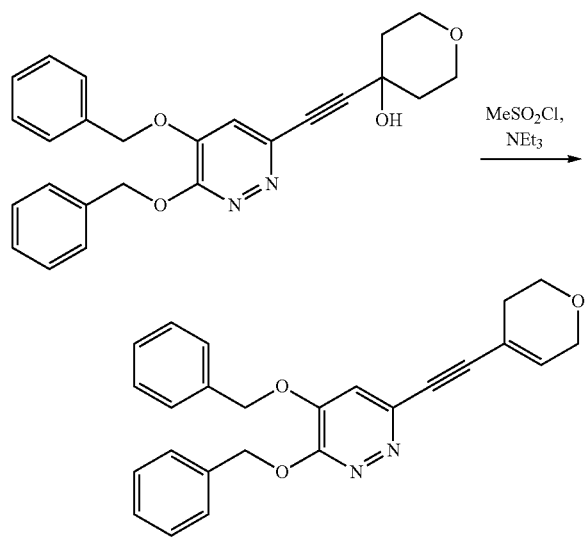

Intermediate 60

3,4-bis(Benzyloxy)-6-[2-(3,6-dihydro-2H-pyran-4-yl)ethynyl]pyridazine

4-{2-[5,6-bis(Benzyloxy)pyridazin-3-yl]ethyl}oxan-4-ol (Intermediate 59; 2.0 g, 4.8 mmol) was dissolved in dichloromethane (20 ml). Triethylamine (2.94 g, 28.82 mmol, 6.0 equiv.) was added to the clear solution followed by the addition of methanesulfonyl chloride (1.64 g, 14.42 mmol, 3.0 equiv.) at room temperature. The reaction mixture was stirred for an hour at room temperature before the reaction mass was poured into water (200 ml) and product was extracted into ethyl acetate (100 ml×2). The organic layer was separated, washed with brine, dried (Na$_2$SO$_4$) and concentrated in vacuo to get the crude title compound (1.0 g, 52% yield) which was used as such for the next step without further purification.

Scheme 11:

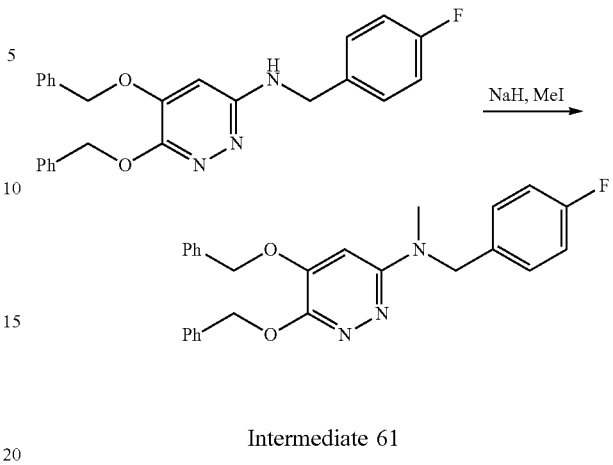

Intermediate 61

5,6-bis(Benzyloxy)-N-[(4-fluorophenyl)methyl]-N-methylpyridazin-3-amine 5,6-bis(Benzyloxy)-N-[(4-fluorophenyl)methyl]pyridazin-3-amine (Intermediate 45; 0.7 g, 1.68 mmol) was dissolved in N,N-dimethylformamide (8 ml) and the solution was cooled to 0° C. before sodium hydride (60% by weight in paraffin; 0.101 g, 2.53 mmol, 1.5 equiv.) was added under nitrogen atmosphere. The reaction mixture was allowed to warm at room temperature for approximately 30 minutes and iodomethane (1.189 g, 8.43 mmol, 5 equiv.) was added. The reaction was allowed to stir at room temperature for one hour before being poured into water (100 ml) and the organic materials were extracted into ethyl acetate (50 ml×2). The organic layer was separated, washed with brine, dried (Na$_2$SO$_4$) and concentrated in vacuo. The crude compound was purified by column chromatography (silica gel, eluting with 0-50% ethyl acetate in hexane) to yield 5,6-bis(benzyloxy)-N-(4-fluorobenzyl)-N-methylpyridazin-3-amine (0.51 g, 64% yield).

Scheme 12:

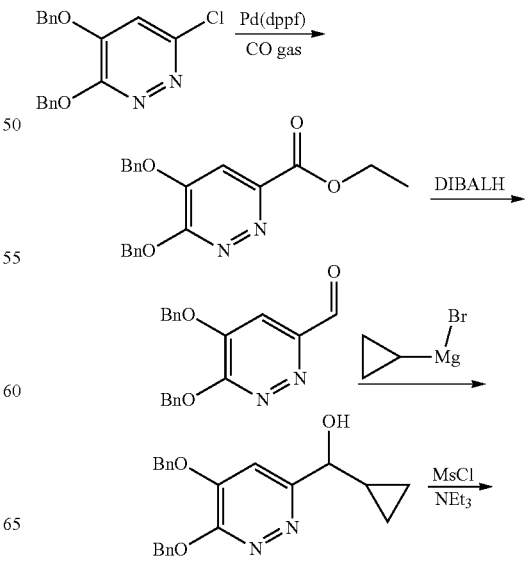

-continued

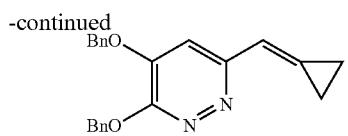

Intermediate 62

Ethyl 5,6-bis(benzyloxy)pyridazine-3-carboxylate

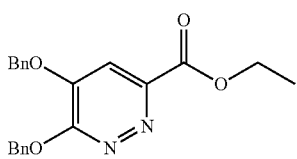 [SMILES: CCOC(=O)c1cc(OCc2ccccc2)c(OCc2ccccc2)nn1]

3,4-Bis(benzyloxy)-6-chloropyridazine (Intermediate 1; 5.0 g, 15.33 mmol) was dissolved in ethanol (75 ml) at room temperature. Sodium acetate (2.52 g, 30.67 mmol) was added and the resulting suspension was purged with nitrogen for 10 minutes. [1,1'-Bis(diphenylphosphino)ferrocene]dichloropalladium(II) dichloromethane complex (0.877 g, 1.073 mmol) was added and reaction was flushed with carbon monoxide gas. Further carbon monoxide was bubbled into the reaction for 15 minutes at room temperature and then the whole was stirred at 90° C. with carbon monoxide bubbling for 2 hours. Upon completion, the reaction mass was poured into water (50 ml) followed by brine (100 ml) and product was extracted into ethyl acetate (3×100 ml). The combined organic layers were separated, dried (Na$_2$SO$_4$) and concentrated in vacuo. The crude product was purified on column chromatography (silica, 0-20% ethyl acetate in hexane) to afford 5,6-bis(benzyloxy) pyridazine-3-carboxylate (3.8 g, 68% yield).

$^1$H NMR (DMSO-d$_6$) δ 7.28-7.58 (m, 11 H), 5.73 (s, 2 H), 5.26 (s, 2 H), 4.46-4.52 (q, 2 H) and 1.44-1.48 (t, 3 H).

Intermediate 63

5,6-bis(Benzyloxy)pyridazine-3-carbaldehyde

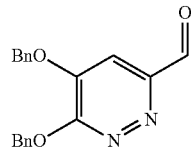 [SMILES: O=Cc1cc(OCc2ccccc2)c(OCc2ccccc2)nn1]

Ethyl 5,6-bis(benzyloxy)pyridazine-3-carboxylate (Intermediate 62; 3.8 g, 10.43 mmol) was dissolved in THF (95 ml) and cooled to 0-5° C. under nitrogen atmosphere. A solution of di-isobutyl-aluminium hydride in THF (1 M, 21 ml, 20.8 mmol) was added at 0-5° C. and reaction mixture was stirred at room temperature for 2 hours. Upon completion the reaction was quenched by the addition of ethyl acetate and then saturated aqueous ammonium chloride solution. The resulting mass was filtered and extracted into ethyl acetate (3×50 ml) and the combined organics were washed with brine, dried (Na$_2$SO$_4$) and concentrated in vacuo. The crude product was purified by column chromatography (silica, eluting with dichloromethane) to afford 5,6-bis(benzyloxy)pyridazine-3-carbaldehyde (2.9 g, 87% yield).

Intermediate 64

(5,6-bis(Benzyloxy)pyridazin-3-yl)(cyclopropyl) methanol

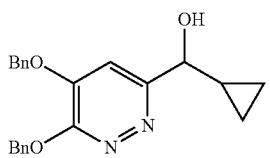

5,6-bis(Benzyloxy)pyridazine-3-carbaldehyde (Intermediate 63; 0.5 g, 1.562 mmol) was dissolved into THF (10 ml) and cooled to 0-5° C. under a nitrogen atmosphere. A solution of cyclopropyl magnesium bromide in THF (0.5 M, 4.7 ml, 2.34 mmol) was added at 0-5° C. and reaction mixture was stirred at room temperature for 4 hours. Upon completion, the reaction was quenched by addition of ethyl acetate and saturated aqueous ammonium chloride solution and extracted into ethyl acetate (2×50 ml). The combined organics were separated and washed with brine, dried (Na$_2$SO$_4$) and concentrated in vacuo. The crude compound was purified by column chromatography (silica, 0-2% methanol in dichloromethane) to afford (5,6-bis(benzyloxy) pyridazin-3-yl)(cyclopropyl)methanol (0.35 g, 61.9% yield).

MS ES$^+$: 363.

Intermediate 65

3,4-bis(Benzyloxy)-6-(cyclopropylidenemethyl) pyridazine

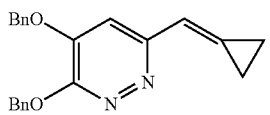 [SMILES: C(=C1CC1)c1cc(OCc2ccccc2)c(OCc2ccccc2)nn1]

(5,6-bis(Benzyloxy)pyridazin-3-yl)(cyclopropyl)methanol (Intermediate 64, 0.34 g, 0.94 mmol) was dissolved in dichloromethane (10.2 ml) and cooled at 0-5° C. under nitrogen atmosphere. Triethylamine (0.474 g, 4.70 mmol) and methanesulfonylchloride (0.162 g, 1.401 mmol) were added to the reaction and it was allowed to stir at room temperature for 3 hours. Upon completion the reaction was quenched by pouring into saturated aqueous sodium bicarbonate solution (25 ml) and the product was extracted into ethyl acetate (2×50 ml). The combined organics were separated, washed with brine, dried (Na$_2$SO$_4$) and concentrated in vacuo. The crude compound was purified by column chromatography (silica, 0-10% ethyl acetate in n-hexane) to afford 3,4-bis(benzyloxy)-6-(cyclopropylidenemethyl) pyridazine (0.18 g, 56% yield).

$^1$H NMR (CDCl$_1$) δ 7.28-7.57 (m, 10 H), 6.67 (s, 1 H), 6.23 (s, 1 H), 5.59 (s, 2 H), 5.14-5.19 (m, 2 H) and 1.90-2.05 (m, 4 H).

MS ES$^+$: 345.

Intermediate 66

4,4,5-Tetramethyl-2-{1-[4-(trifluoromethyl)phenyl] ethenyl}-1,3,2-dioxaborolane

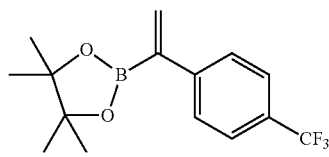 [SMILES: C=C(B1OC(C)(C)C(C)(C)O1)c1ccc(C(F)(F)F)cc1]

A mixture of (1,3-bis(2,6-diisopropylphenyl)-2,3-dihydro-1H-imidazol-2-yl)copper(II) chloride (0.718 g, 1.469 mmol), sodium tert-butoxide (0.141 g, 1.469 mmol) and THF (106 ml) was allowed to stir under nitrogen for 10 minutes. 4,4,4',4',5,5,5',5'-Octamethyl-2,2'-bi(1,3,2-dioxaborolane) (8.21 g, 32.3 mmol) was added and the mixture stirred for 30 minutes at room temperature. The mixture was cooled to −78° C. and a solution of 1-ethynyl-4-(trifluoromethyl)benzene (5 g, 29.4 mmol) in THF (21.30 ml) and methanol (1.308 ml, 32.3 mmol) was added via syringe. The whole mixture was then stirred at −40° C. with slow warming to 20° C. overnight. The resulting mixture was filtered through a pad of diatomaceous earth to give a brown solution which was concentrated in vacuo. The residue was purified by column chromatography (silica, eluting with 0-6% diethyl ether in petrol). The combined fractions were subjected to further purification by column chromatography (silica, eluting with 0-50% dichloromethane in petrol) to afford 4,4,5,5-tetramethyl-2-{1-[4-(trifluoromethyl)phenyl] ethenyl}-1,3,2-dioxaborolane as a yellow solid (2.82 g, 32%).

$^1$H NMR (DMSO-d$_6$) δ 7.67-7.72 (m, 2 H) 7.61-7.66 (m, 2 H) 6.21 (m, 1 H) 6.11 (m, 1 H) and 1.28 (s, 12 H).

Intermediate 67

3,4-bis(Benzyloxy)-6-{1-[4-(trifluoromethyl)phenyl] ethenyl}-pyridazine

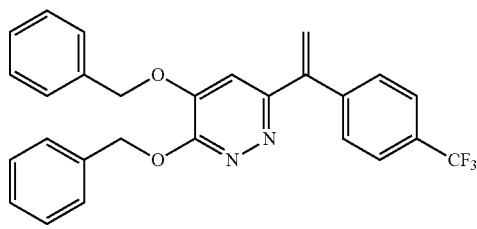 [SMILES: C=C(c1ccc(C(F)(F)F)cc1)c1cc(OCc2ccccc2)c(OCc2ccccc2)nn1]

Prepared according to the method for 3,4-bis(benzyloxy)-6-(1-phenylethenyl)pyridazine (Intermediate 25) from 3,4-bis(benzyloxy)-6-chloropyridazine (Intermediate 1) and 4,4,5,5-tetramethyl-2-{1-[4-(trifluoromethyl)-phenyl]ethenyl}-1,3,2-dioxaborolane (Intermediate 66) in 48% yield.

$^1$H NMR (DMSO-d$_6$) δ 7.72 (m, 2 H), 7.30-7.50 (m, 13 H), 6.02 (s, 1 H), 5.87 (s, 1 H), 5.55 (s, 2 H) and 5.31 (s, 2 H).

MS: ES$^+$: 463.

Intermediate 68

3,4-bis(Benzyloxy)-6-{1-[4-(trifluoromethyl)phenyl]-cyclopropyl}pyridazine

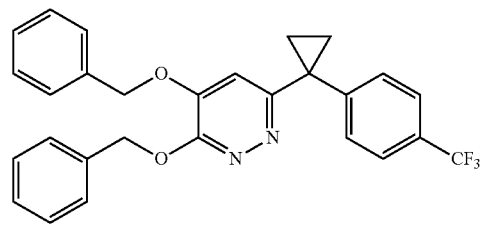 [SMILES: FC(F)(F)c1ccc(C2(c3cc(OCc4ccccc4)c(OCc4ccccc4)nn3)CC2)cc1]

Prepared according to the method for 3,4-bis(benzyloxy)-6-(1-phenylcyclopropyl)pyridazine (Intermediate 26) from 3,4-bis(benzyloxy)-6-{1-[4-(trifluoromethyl)phenyl]ethenyl}-pyridazine (Intermediate 67) in 38% yield.

$^1$H NMR (DMSO-d$_6$) δ 7.65 (m, 2 H) 7.29-7.48 (m, 12 H) 6.90 (s, 1 H) 5.50 (s, 2 H) 5.19 (s, 2 H) 1.54-1.59 (m, 2 H) and 1.34-1.38 (m, 2 H).

MS: ES$^+$: 477.

Intermediate 69

3,4=bis(Benzyloxy)-6-{2-[2-chloro-4-(trifluoromethyl)phenyl]-ethynyl}pyridazine

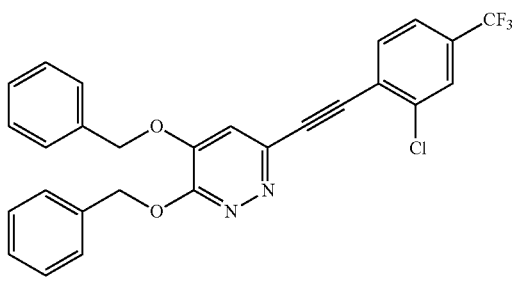 [SMILES: FC(F)(F)c1ccc(C#Cc2cc(OCc3ccccc3)c(OCc3ccccc3)nn2)c(Cl)c1]

Prepared as described for 3,4-bis(benzyloxy)-6-((3-methyl-4-(trifluoromethyl)phenyl)-ethynyl)pyridazine (Intermediate 74) from 3,4-bis(benzyloxy)-6-ethynylpyridazine (Intermediate 5) and 1-bromo-2-chloro-4-(trifluoromethyl)benzene in 75% yield.

$^1$H NMR (DMSO-d$_6$) δ 8.11 (s, 1 H), 8.00 (m, 1 H), 7.84 (m, 1 H), 7.62 (s, 1 H), 7.32-7.52 (m, 10 H), 5.60 (s, 2 H) and 5.33 (s, 2 H).

MS: ES$^+$: 495.

Intermediate 70

3,4-bis(Benzyloxy)-6-{2-[2-fluoro-4-(trifluoromethyl)phenyl]-ethynyl}pyridazine

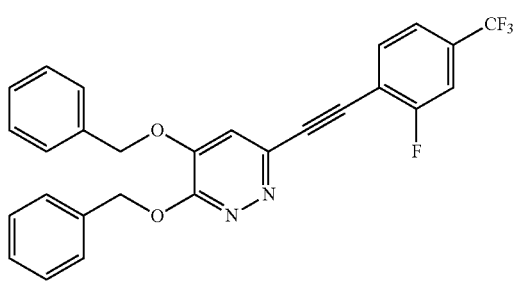 [SMILES: Fc1cc(C(F)(F)F)ccc1C#Cc1cc(OCc2ccccc2)c(OCc2ccccc2)nn1]

Prepared as described for 3,4-bis(benzyloxy)-6-((3-methyl-4-(trifluoromethyl)phenyl)-ethynyl)pyridazine (Intermediate 74) from 3,4-bis(benzyloxy)-6-ethynylpyridazine (Intermediate 5) and 1-bromo-2-fluoro-4-(trifluoromethyl)benzene in 16% yield.

$^1$H NMR (DMSO-d$_6$) δ 7.90-8.00 (m, 2 H), 7.72 (m, 1 H), 7.64 (s, 1 H) 7.30-7.53 (m, 10 H), 5.60 (s, 2 H) and 5.33 (s, 2 H).

MS: ES$^+$: 479.

Intermediate 71

3,4-bis(Benzyloxy)-6-[(E)-2-[3,5-bis(trifluoromethyl)phenyl]-ethenyl]pyridazine

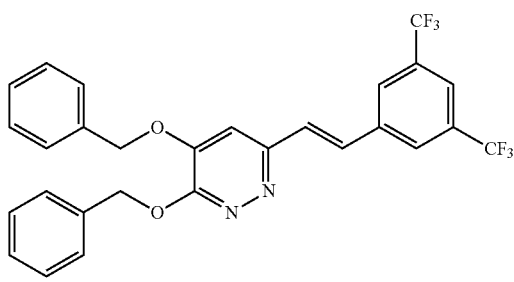 [SMILES: FC(F)(F)c1cc(/C=C/c2cc(OCc3ccccc3)c(OCc3ccccc3)nn2)cc(C(F)(F)F)c1]

Prepared as described for 3,4-bis(benzyloxy)-6-(1-phenylethenyl)pyridazine (Intermediate 25) from 3,4-bis(benzyloxy)-6-chloropyridazine (Intermediate 1) and 2-[(E)-2-[3,5-bis(trifluoromethyl)phenyl]ethenyl]-4,4,5,5-tetramethyl-1,3,2-dioxaborolane in 77% yield.

$^1$H NMR (DMSO-d$_6$) δ 8.38 (s, 2 H), 8.04 (s, 1 H), 7.82-7.89 (m, 1 H), 7.67-7.76 (m, 2 H), 7.31-7.54 (m, 10 H), 5.58 (s, 2 H) and 5.32 (s, 2 H).

MS: ES$^+$: 531.

Intermediate 72

3,4-bis(Benzyloxy)-6-[(E)-2-[2,4-bis(trifluoromethyl)phenyl]-ethenyl]pyridazine

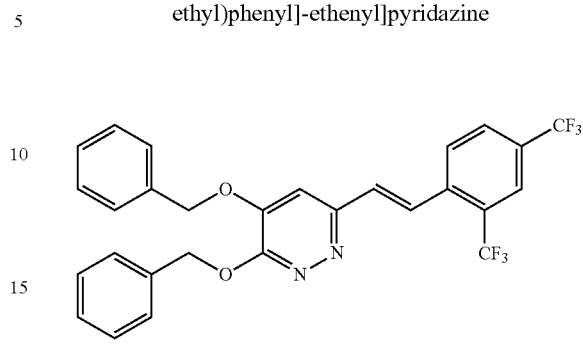

Prepared from 3,4-bis(benzyloxy)-6-ethenylpyridazine (Intermediate 78) according to the procedure used to synthesise 3,4-bis(benzyloxy)-6-[(E)-2-[2-methyl-4-(trifluoromethyl)phenyl]ethenyl]pyridazine (Intermediate 76) in 36% yield.

$^1$H NMR (DMSO-d$_6$) δ 8.27 (m, 1 H), 8.14 (m, 1 H), 8.08 (s, 1 H), 7.87 (m, 1 H), 7.59 (s, 1 H), 7.47-7.55 (m, 5 H), 7.32-7.46 (m, 6 H), 5.59 (s, 2 H) and 5.35 (s, 2 H).

Intermediate 73

3,4-bis(Benzyloxy)-6-[(E)-2-[3,4-bis(trifluoromethyl)phenyl]ethenyl]pyridazine

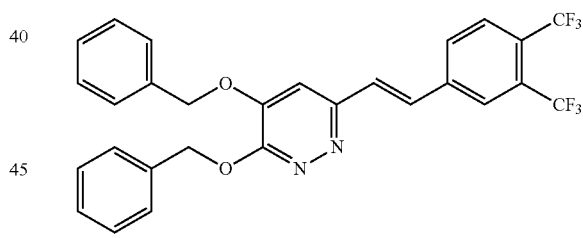

3,4-bis(Benzyloxy)-6-ethenylpyridazine (Intermediate 78: 0.578 g, 1.816 mmol), cesium carbonate (0.887 g, 2.72 mmol), dichloropalladiumtricyclohexylphosphane (1:2) (0.067 g, 0.091 mmol) and 4-chloro-1,2-bis(trifluoromethyl)benzene (0.542 g, 2.179 mmol) were combined. The reaction vessel was evacuated and purged with nitrogen before toluene (6.05 ml) was added under vacuum and the whole was stirred under nitrogen and heated to 140° C. for 11 hours. Upon quenching with saturated aqueous ammonium chloride, the resulting mixture was diluted with dichloromethane, passed through a phase separator and concentrated in vacuo. The residue was purified by column chromatography eluting (silica, 0-50% ethyl acetate in petrol) to yield crude 3,4-bis(benzyloxy)-6-[(E)-2-[3,4-bis(trifluoromethyl)phenyl]-ethenyl]-pyridazine which was used directly in the next step without further purification.

MS: ES$^+$: 531.

Intermediate 74

3,4-bis(Benzyloxy)-6-((3-methyl-4-(trifluoromethyl)phenyl)-ethynyl)pyridazine

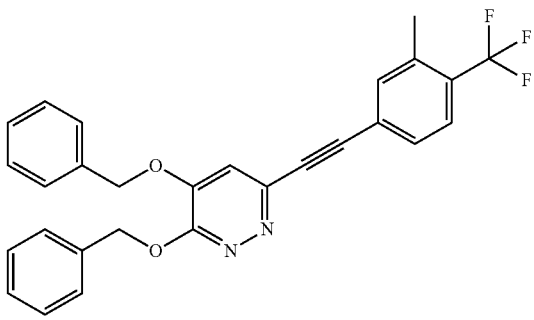 [SMILES: Cc1cc(C#Cc2cc(OCc3ccccc3)c(OCc3ccccc3)nn2)ccc1C(F)(F)F]

3,4-bis(Benzyloxy)-6-ethynylpyridazine (Intermediate 5; 3.0 g, 9.48 mmol), copper(I) iodide (0.181 g, 0.948 mmol) and bis(triphenylphosphine)-palladium(II) dichloride (0.333 g, 0.474 mmol) were combined. The reaction vessel was purged with nitrogen, followed by the addition of 4-bromo-2-methyl-1-(trifluoromethyl)benzene (2.493 g, 10.43 mmol), 1,8-diazabicycloundec-7-ene (8.66 g, 56.9 mmol) and tetrahydrofuran (32 ml) before the resulting mixture was allowed to stir at room temperature overnight. The reaction was quenched with brine and extracted into ethyl acetate (×2) and the combined organic extracts were washed with brine, dried (MgSO$_4$) and concentrated in vacuo to afford a dark brown gum. The gum was purified by column chromatography (silica, 0-50% ethyl acetate in petrol) to afford 3,4-bis(benzyloxy)-6-((3-methyl-4-(trifluoromethyl)phenyl)-ethynyl)pyridazine as a dark brown oil (1.22 g, 27%).

$^1$H NMR (CD$_2$Cl$_2$) δ 7.49-7.67 (m, 3 H), 7.33-7.46 (m, 10 H), 7.06 (s, 1 H), 5.64 (s, 2 H), 5.20 (s, 2 H) and 2.50 (s, 3 H).

MS ES$^+$: 475.

Intermediate 75

3,4-bis(Benzyloxy)-6-{2-[3-chloro-4-(trifluoromethyl)phenyl]-ethynyl}pyridazine

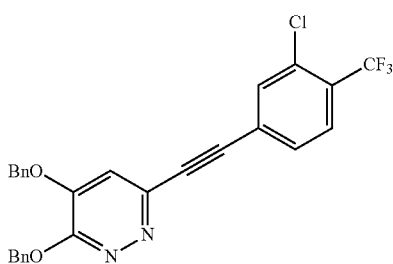 [SMILES: FC(F)(F)c1ccc(C#Cc2cc(OCc3ccccc3)c(OCc3ccccc3)nn2)cc1Cl]

Prepared as described for 3,4-bis(benzyloxy)-6-((3-methyl-4-(trifluoromethyl)-phenyl)ethynyl)pyridazine (Intermediate 74) using 4-bromo-2-chloro-1-(trifluoromethyl)benzene in 98% yield.

$^1$H NMR (CD$_2$Cl$_2$) δ 7.80 (s, 1 H), 7.71-7.76 (m, 1 H), 7.62-7.69 (m, 1 H), 7.52 (d, 1 H), 7.32-7.46 (m, 9 H), 7.08 (s, 1 H), 5.64 (s, 2 H) and 5.22 (s, 2 H).

MS ES$^+$: 495.

Intermediate 76

3,4-bis(Benzyloxy)-6-[(E)-2-[2-methyl-4-(trifluoromethyl)phenyl]ethenyl]pyridazine

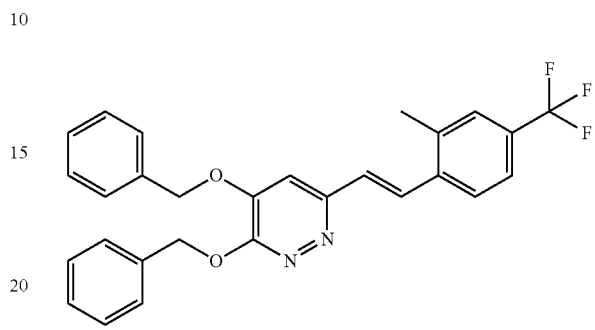

1-Bromo-2-methyl-4-(trifluoromethyl)benzene (1.144 g, 4.79 mmol), 3,4-bis(benzyloxy)-6-ethenylpyridazine (Intermediate 78; 1.27 g, 3.99 mmol), palladium(II) acetate (0.045 g, 0.199 mmol), triethylamine (10.56 ml, 76 mmol), tri-o-tolylphosphine (0.243 g, 0.798 mmol) and acetonitrile (8 ml) were combined. The reaction mixture was subjected to microwave irradiation at 120° C. for 30 minutes before being quenched with water and extracted into ethyl acetate. The combined organics were washed with brine, dried (MgSO$_4$) and concentrated in vacuo to afford an orange gum. This was purified by column chromatography (silica, eluting with 0-30% ethyl acetate in petrol) to afford 3,4-bis(benzyloxy)-6-[(E)-2-[2-methyl-4-(trifluoromethyl)phenyl]ethenyl]pyridazine as a white solid (1.04 g, 55%).

$^1$H NMR (CD$_2$Cl$_2$) δ 7.78 (d, 1 H), 7.71 (d, 1 H), 7.26-7.57 (m, 13 H), 7.09 (br. s., 1 H), 5.62 (s, 2 H), 5.28 (s, 2 H) and 2.52 (s, 3 H).

MS ES$^+$: 477.

Intermediate 77

3,4-bis(Benzyloxy)-6-[(E)-2-[3,5-difluoro-4-(trifluoromethyl)phenyl]ethenyl]pyridazine

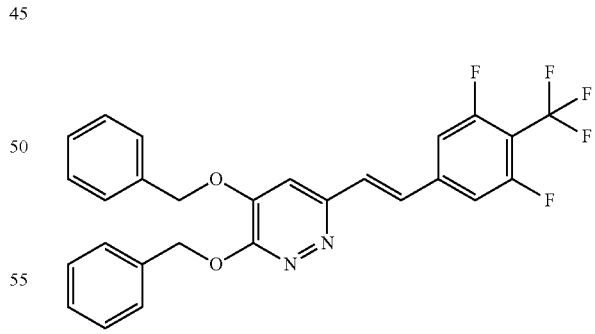

A mixture of 3,4-bis(benzyloxy)-6-ethenylpyridazine (Intermediate 78; 1.09 g, 3.42 mmol), tri-o-tolylphosphine (0.208 g, 0.685 mmol), palladium(II) acetate (0.038 g, 0.171 mmol), 5-bromo-1,3-difluoro-2-(trifluoromethyl)benzene (1.07 g, 4.11 mmol), triethylamine (9.07 ml, 65.1 mmol) and acetonitrile (10 ml) was subjected to microwave irradiation at 120° C. for 2 hours. The reaction mixture was filtered through diatomaceous earth to remove the insoluble white precipitate and the filtrate partitioned between ethyl acetate and brine. The organics were dried (MgSO₄) and concentrated in vacuo before the crude product was purified by column chromatography (silica, eluting with 0-30% ethyl acetate in petrol) to afford, 3,4-bis(benzyloxy)-6-[(E)-2-[3,5-difluoro-4-(trifluoromethyl)phenyl]ethenyl]pyridazine, the title compound as a yellow solid (1.21 g, 71%).

¹H NMR (CD₂Cl₂) δ 7.56 (d, 2 H), 7.34-7.52 (m, 10 H), 7.27 (d, 2 H), 7.09 (s, 1 H), 5.67 (s, 2 H) and 5.28 (s, 2 H).
MS ES⁺: 499.

Intermediate 78

3,4-bis(Benzyloxy)-6-ethenylpyridazine

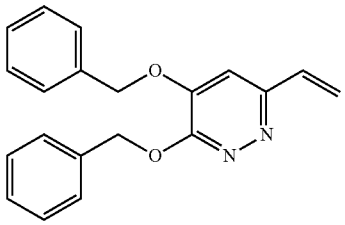 [SMILES: C=Cc1cc(OCc2ccccc2)c(OCc2ccccc2)nn1]

A vessel containing 2,4,6-triethenyl-1,3,5,2,4,6-trioxatriborinane compound with pyridine (1:1) (1.105 g, 4.59 mmol), 3,4-bis(benzyloxy)-6-chloropyridazine (Intermediate 1, 3 g, 9.18 mmol) and potassium carbonate (3.17 g, 22.95 mmol) was evacuated and flushed with nitrogen. Dioxane (30 ml) and water (3 ml) were added in vacuo and the reaction was degassed before tetrakis(triphenyl-phosphine)palladium(0) (0.530 g, 0.459 mmol) was added. The resulting mixture was then heated at 80° C. for 18 hours and upon cooling, was diluted with ethyl acetate and washed with saturated aqueous sodium carbonate solution. The organics were dried (MgSO₄), filtered and solvent removed in vacuo to give a brown oil. This was purified by column chromatography (silica, eluting with 0-30% ethyl acetate in petrol) to afford 3,4-bis(benzyloxy)-6-ethenylpyridazine (1.1 g, 38% yield).

¹H NMR (CDCl₃) δ 7.51-7.65 (m, 2 H), 7.29-7.49 (m, 8 H), 6.82-6.98 (m, 2 H), 5.89-6.03 (m, 1 H), 5.67 (s, 2 H), 5.45-5.59 (m, 1 H) and 5.24 (s, 2 H).
MS ES⁺: 319.

Intermediate 79

3,4-bis(Benzyloxy)-6-[(E)-2-[3-fluoro-4-(trifluoromethyl)-phenyl]ethenyl]pyridazine

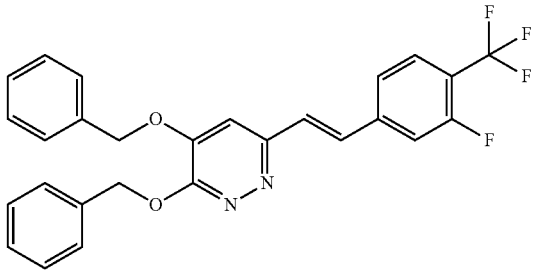 [SMILES: Fc1cc(/C=C/c2cc(OCc3ccccc3)c(OCc3ccccc3)nn2)ccc1C(F)(F)F]

A vessel containing 3,4-bis(benzyloxy)-6-ethenylpyridazine (Intermediate 78, 1.09 g, 3.42 mmol), tris-(2-methylphenyl)phosphane (0.208 g, 0.685 mmol), 2-fluoro-4-iodo-1-(trifluoromethyl)benzene (1.191 g, 4.11 mmol) and palladium(II) acetate (0.038 g, 0.171 mmol) was evacuated and acetonitrile (10 ml) and triethylamine (9.07 ml, 65.1 mmol) were added in vacuo and then the mixture was flushed with nitrogen. The reaction was then heated in the microwave at 80° C. for 4 hours and, upon cooling, was diluted with dichloromethane and washed with saturated aqueous ammonium chloride solution. The organics were dried (MgSO₄), filtered and solvent removed in vacuo to give a brown oil which was purified by column chromatography (silica, eluting with 30-100% dichloromethane in petrol) to yield 3,4-bis(benzyloxy)-6-[(E)-2-[3-fluoro-4-(trifluoromethyl)phenyl]ethenyl]pyridazine (1.1 g, 2.29 mmol, 67% yield).

¹H NMR (CDCl₃) δ 7.53-7.68 (m, 3 H), 7.31-7.53 (m, 12 H), 6.97 (s, 1 H), 5.71 (s, 2 H) and 5.28 (s, 2 H).
MS ES⁺: 481.

2. EXAMPLES

Scheme A:

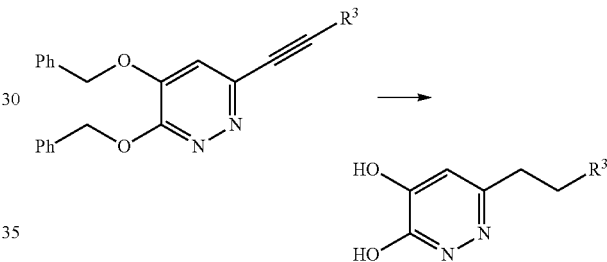

Example 1

4-Hydroxy-6-(2-phenylethyl)pyridazin-3(2H)-one

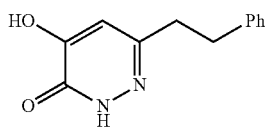

3,4-bis(Benzyloxy)-6-(phenylethynyl)pyridazine (Intermediate 2; 320 mg, 0.815 mmol) was dissolved in ethanol and palladium on carbon (87 mgs, 0.815 mmol) was added before the mixture was purged and subjected to hydrogen gas. The reaction was then filtered and evaporated and the residue was purified on silica using 0-10% methanol in dichloromethane to yield a red solid. This was triturated with ethanol to give the crude title compound as a white solid and the mother liquors were evaporated and dissolved in a minimum amount of dimethyl sulfoxide and purified by C₁₈ reverse phase silica chromatography to yield 4-hydroxy-6-(2-phenethyl)pyridazin-3(2H)-one (31 mg, 0.14 mmol, 17.6% yield).

¹H NMR (400 MHz, DMSO-d₆) δ 12.80 (s, br, 1 H), 10.7 (s, br, 1 H), 7.15-7.30 (m, 6 H), 2.85-2.95 (m, 2 H) and 2.76-2.83 (s, 2 H).
MS ES⁺: 217.

Example 2

6-[2-(4-Fluorophenyl)ethyl]-4-hydroxypyridazin-3(2H)-one

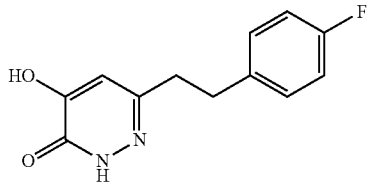 [SMILES: O=c1[nH]nc(CCc2ccc(F)cc2)cc1O]

Prepared as described for 4-hydroxy-6-(2-phenylethyl)pyridazin-3(2H)-one (Example 1) from 3,4-bis(benzyloxy)-6-[(4-fluorophenyl)ethynyl]pyridazine (Intermediate 3).

$^1$H NMR (400 MHz, DMSO-d$_6$) δ 7.22-7.28 (m, 2 H), 7.05-7.13 (m, 2 H), 6.58 (s, 1 H), 2.85-2.94 (m, 2 H) and 2.73-2.79 (m, 2H)

MS ES$^+$: 236.

Example 3

4-Hydroxy-6-{2-[5-(trifluoromethyl)pyridin-2-yl]ethyl}pyridazin-3(2H)-one

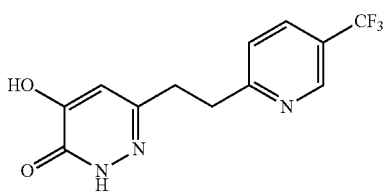 [SMILES: O=c1[nH]nc(CCc2ccc(C(F)(F)F)cn2)cc1O]

3,4-bis(benzyloxy)-6-{[5-(trifluoromethyl)pyridin-2-yl]ethynyl}pyridazine (Intermediate 6; 460 mg, 0.997 mmol) was dissolved in ethanol and palladium on carbon was added before the mixture was purged and subjected to hydrogen gas. On completion of the reaction the solvent was removed in vacuo to yield a residue which was purified by reverse phase chromatography using 5-90% acetonitrile in acidic water (0.05% trifluoroacetic acid) to give, after recrystallisation from an ethanol-heptane mixture, 4-hydroxy-6-(2-(5-(trifluoromethyl)pyridin-2-yl)ethyl)pyridazin-3(2H)-one (136 mg, 0.48 mmol, 48% yield).

$^1$H NMR (400 MHz, DMSO-d$_6$) δ 12.66 (br s, 1 H), 10.72 (br s, 1 H), 8.89 (s, 1 H), 8.11 (s, 1 H), 7.54 (s, 1 H), 6.62 (s, 1 H), 3.13-3.19 (m, 2 H) and 2.90-2.98 (m, 2 H)

MS ES$^+$: 286.

Scheme B:

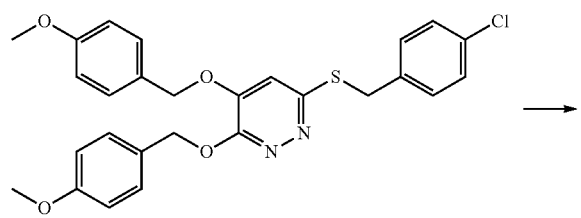

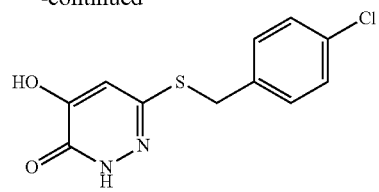

Example 4

6-[(4-Chlorobenzyl)sulfanyl]-4-hydroxypyridazin-3(2H)-one

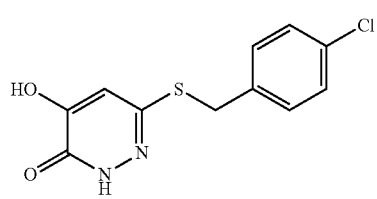 [SMILES: O=c1[nH]nc(SCc2ccc(Cl)cc2)cc1O]

To a solution of 6-[(4-chlorobenzyl)sulfanyl]-3,4-bis[(4-methoxybenzyl)oxy]pyridazine (Intermediate 8; 527 mg, 1.04 mmol) in methanol (5177 μl) was added a solution of hydrogen chloride in dioxane (4.0 M, 5177 μl, 20.71 mmol) and the reaction was allowed to stir at room temperature for 72 hours. The resulting mixture was concentrated in vacuo to afford a yellow solid which was recrystallised from ethanol to afford 6-[(4-chlorobenzyl)sulfanyl]-4-hydroxypyridazin-3(2H)-one as white crystals (153 mg, 56.9 mmol, 55%).

$^1$H NMR (400 MHz, DMSO-d$_6$): δ 12.99 (s, br, 1 H), 10.6 (s, br, 1 H), 7.35-7.46 (m, 4 H), 6.53 (s, 1 H) and 4.24 (s, 2 H).

MS ES$^+$: 269.

Example 5

4-Hydroxy-6-{2-[6-(trifluoromethyl)pyridin-3-yl]ethyl}pyridazin-3(2H)-one

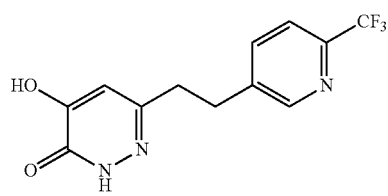 [SMILES: O=c1[nH]nc(CCc2ccc(C(F)(F)F)nc2)cc1O]

Prepared as described for 4-hydroxy-6-(2-phenethyl)pyridazin-3(2H)-one (Example 1) from 3,4-bis(benzyloxy)-6-{[6-(trifluoromethyl)pyridin-3-yl]ethynyl}pyridazine (Intermediate 9) except that the reaction was carried out in a mixture of methanol and tetrahydrofuran (1:1). The resulting crude product was purified by preparative HPLC under acidic conditions to afford 4-hydroxy-6-{(2-[6-(trifluoromethyl)pyridin-3-yl]ethyl}pyridazin-3(2H)-one as a cream solid (26% yield).

$^1$H NMR (400 MHz, DMSO-$d_6$): δ 12.68 (br s, 1 H), 10.80 (s, br, 1 H), 8.64 (s, 1 H), 7.92-7.98 (m, 1 H), 7.80-7.88 (m, 1 H), 6.61 (s, 1 H), 2.98-3.08 (m, 2 H) and 2.80-2.88 (m, 2 H).

MS ES$^+$: 286.

Example 6

6-[2-(3-Fluorophenyl)ethyl]-4-hydroxypyridazin-3(2H)-one

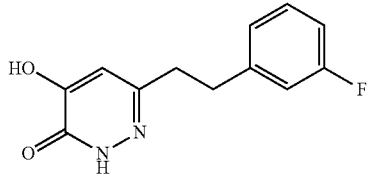 [SMILES: O=c1[nH]nc(CCc2cccc(F)c2)cc1O]

Prepared as described for 4-hydroxy-6-(2-phenethyl)pyridazin-3(2H)-one (Example 1) from 3,4-bis(benzyloxy)-6-[(3-fluorophenyl)ethynyl]pyridazine (Intermediate 10) except that the reaction was carried out in methanol. The resulting crude product was recrystallised from a mixture of ethanol and heptane to afford 6-[2-(3-fluorophenyl)ethyl]-4-hydroxypyridazin-3(2H)-one as cream crystals (yield=63%).

$^1$H NMR (400 MHz, DMSO-$d_6$): δ 12.67 (br s, 1 H), 10.71 (br s, 1 H), 7.25-7.38 (s, 1 H), 6.95-7.15 (m, 3 H), 6.61 (s, 1 H), 2.88-2.95 (m, 2 H) and 2.73-2.81 (m, 2 H).

MS ES$^+$: 235.

Example 7

6-[2-(2-Fluorophenyl)ethyl]-4-hydroxypyridazin-3(2H)-one

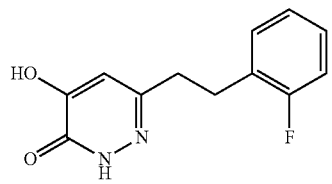

Prepared as described for 4-hydroxy-6-(2-phenethyl))pyridazin-3(2H)-one (Example 1) from 3,4-bis(benzyloxy)-6-[(2-fluorophenyl)ethynyl]pyridazine (Intermediate 11).

$^1$H NMR (400 MHz, DMSO-$d_6$) δ 12.69 (br s, 1 H), 10.77 (br s, 1 H), 7.21-7.35 (m, 2 H), 7.08-7.21 (m, 2 H), 6.60 (s, 1 H), 2.85-2.95 (m, 2 H) and 2.72-2.79 (m, 2H)

MS ES$^+$: 235.

Example 8

6-[2-(3,5-Difluorophenyl)ethyl]-4-hydroxy-pyridazin-3(2H)-one

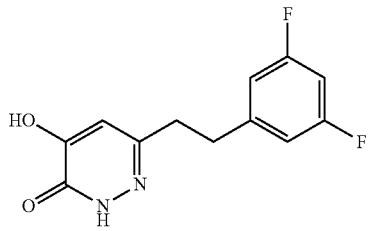 [SMILES: O=c1[nH]nc(CCc2cc(F)cc(F)c2)cc1O]

Prepared as described for 4-hydroxy-6-(2-phenethyl)pyridazin-3(2H)-one (Example 1) from 3,4-bis(benzyloxy)-6-[(3,5-difluorophenyl)ethynyl]pyridazine (Intermediate 12). The crude material was purified by reverse phase column chromatography (10 g C18) cartridge eluting with 0-100% methanol and water with acidic modifier to afford a pale orange oil solid. This was recrystallised from a mixture of ethanol and heptane to give a peach coloured solid (yield=29%).

$^1$H NMR (400 MHz, DMSO-$d_6$): δ 12.69 (br s, 1 H), 10.74 (br s, 1 H), 6.95-7.05 (m, 3 H), 6.60 (s, 1 H), 2.88-2.95 (m, 2 H) and 2.74-2.81 (m, 2 H).

MS ES$^+$: 253.

Example 9

6-[2-(3,4-Difluorophenyl)ethyl]-4-hydroxy-pyridazin-3(2H)-one

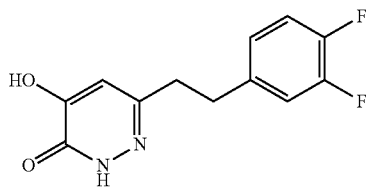 [SMILES: O=c1[nH]nc(CCc2ccc(F)c(F)c2)cc1O]

Prepared as described for 4-hydroxy-6-(2-phenethyl)pyridazin-3(2H)-one (Example 1) from 3,4-bis(benzyloxy)-6-[2-(3,4-difluorophenyl)ethynyl]pyridazine (Intermediate 13). The crude material was purified by reverse phase chromatography, eluting with 5-100% acetonitrile in water with a 0.05% formic acid modifier in the water.

$^1$H NMR (400 MHz, DMSO-$d_6$): δ 12.6 (s, br, 1 H), 10.8 (s, br, 1 H), 7.24-7.38 (m, 2 H), 7.02-7.09 (m, 1 H), 6.64 (s, 1 H), 2.84-2.92 (m, 2 H) and 2.72-2.81 (m, 2 H).

MS ES$^+$: 253.

Example 10

4-Hydroxy-6-{2-[3-(trifluoromethoxy)phenyl]ethyl}pyridazin-3(2H)-one

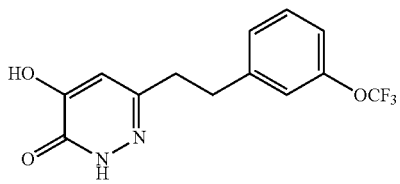 [SMILES: O=c1[nH]nc(CCc2cccc(OC(F)(F)F)c2)cc1O]

Prepared as described for 4-hydroxy-6-(2-phenethyl)pyridazin-3(2H)-one (Example 1) from 3,4-bis(benzyloxy)-6-(2-[3-(trifluoromethoxy)phenyl]ethynyl)pyridazine (Intermediate 14). The residue was purified by reverse phase column chromatography (30 g C18) cartridge eluting with 0-100% methanol in water with acidic modifier and the appropriate fractions combined and concentrated. The crude product was recrystallised from ethyl acetate/heptane to give a white solid (yield=23%).

$^1$H NMR (400 MHz, DMSO-d$_6$): δ 12.67 (br s, 1 H), 10.71 (br s, 1 H), 7.35-7.45 (m, 1 H), 7.15-7.30 (m, 3 H), 6.51 (s, 1 H), 2.92-2.98 (m, 2 H) and 2.74-2.84 (m, 2 H).

MS ES$^+$: 301.

Example 11

4-Hydroxy-6-{2-[3-(trifluoromethyl)phenyl]ethyl}pyridazin-3(2H)-one

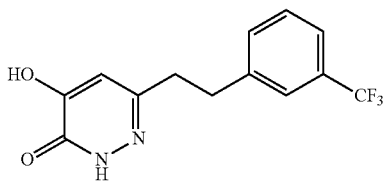 [SMILES: O=c1[nH]nc(CCc2cccc(C(F)(F)F)c2)cc1O]

Prepared as described for 4-hydroxy-6-(2-phenethyl)pyridazin-3(2H)-one (Example 1) from 3,4-bis(benzyloxy)-6-{2-[3-(trifluoromethyl)phenyl]ethynyl}pyridazine (Intermediate 15) except that the reaction was carried out in a mixture of methanol and tetrahydrofuran (2:1). The crude material was purified by reverse phase chromatography, eluting with 5-80% acetonitrile/water with a 0.05% formic acid modifier in the water. The crude product was recrystallised from ethanol/heptane to give a white solid (yield=27%).

$^1$H NMR (400 MHz, DMSO-d$_6$): δ 12.7 (s, br, 1 H), 10.7 (s, br, 1 H), 7.59 (s, 1 H), 7.49-7.53 (m, 3 H), 6.61 (s, 1 H), 2.95-3.01 (m, 2 H) and 2.77-2.81 (m, 2 H).

MS ES$^+$: 285.

Example 12

4-Hydroxy-6-{2-[5-(trifluoromethyl)pyridin-3-yl]ethyl}pyridazin-3(2H)-one

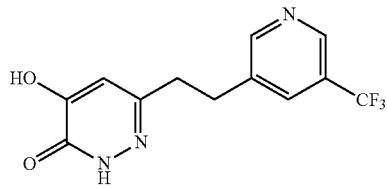 [SMILES: O=c1[nH]nc(CCc2cncc(C(F)(F)F)c2)cc1O]

To a solution of 3,4-bis(benzyloxy)-6-{2-[5-(trifluoromethyl)pyridin-3-yl]ethynyl}pyridazine (Intermediate 16, 1.5 g) in methanol (10 ml) was added 10% palladium on carbon (0.04 g) slowly under nitrogen and the reaction mixture was stirred for 30 minutes at room temperature under a hydrogen atmosphere. The resulting mixture was filtered through a "Celite" (trade mark) diatomaceous earth bed under nitrogen atmosphere and washed with methanol before the filtrate was concentrated under vacuum to afford crude 3,4-bis(benzyloxy)-6-(2-(5-(trifluoromethyl)pyridin-3-yl)ethyl)pyridazine (0.4 g, 0.86 mmol). This was taken up in methanol (10 ml) at room temperature and 10% palladium on carbon (0.04 g) was added slowly under nitrogen atmosphere. The mixture was then stirred under hydrogen (200 psi) at room temperature overnight before being filtered through a bed of "Celite" diatomaceous earth under nitrogen and washed with methanol. The organic layer was concentrated in vacuo to afford the crude product (0.2 g) which was purified by the preparative HPLC to afford homogeneous 4-hydroxy-6-{2-[5-(trifluoromethyl)pyridin-3-yl]ethyl}pyridazin-3(2H)-one (0.03 g, 81.6% yield).

$^1$H NMR (400 MHz, DMSO-d$_6$): δ 12.72 (s, br, 1 H), 10.81 (s, br, 1 H), 8.80 (s, 1 H), 8.75 (s, 1 H), 8.10 (s, 1 H), 6.63 (s, 1 H), 3.00-3.34 (m, 2 H) and 2.81-2.85 (m, 2 H).

MS ES$^+$: 286.

Example 13

6-(2-Cyclohexylethyl)-4-hydroxypyridazin-3(2H)-one

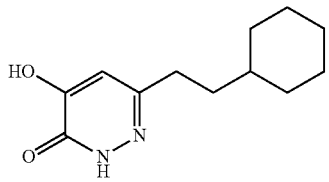 [SMILES: O=c1[nH]nc(CCC2CCCCC2)cc1O]

Prepared as described for 4-hydroxy-6-(2-phenethyl)pyridazin-3(2H)-one (Example 1) from 3,4-bis(benzyloxy)-6-(cyclohexylethynyl)pyridazine (Intermediate 17) except that the reaction was carried out in a mixture of methanol and tetrahydrofuran (1:1). The resulting crude product was purified by preparative HPLC under acidic conditions. The solid obtained was recrystallised from methyl tert-butyl ether and ethyl acetate to afford 6-(2-cyclohexylethyl)-4-hydroxypyridazin-3(2H)-one as a cream solid (11% yield).

$^1$H NMR (400 MHz, DMSO-d$_6$) δ 12.62 (br s, 1 H), 10.68 (br s, 1 H), 6.52 (s, 1 H), 2.39-2.48 (m, 2 H), 1.56-1.76 (m, 5 H), 1.38-1.49 (m, 2 H), 1.05-1.27 (m, 4 H), 0.80-0.97 (m, 2 H)

MS ES$^+$: 223.

Example 14

6-(2-Cyclopropylethyl)-4-hydroxypyridazin-3(2H)-one

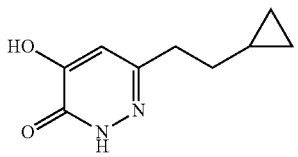 [SMILES: O=c1[nH]nc(CCC2CC2)cc1O]

Prepared as described for 4-hydroxy-6-(2-phenethyl)pyridazin-3(2H)-one (Example 1) from 3,4-bis(benzyloxy)-6-(cyclopropylethynyl)pyridazine (Intermediate 18) except that the reaction was carried out in ethanol. The resulting crude product was purified by preparative HPLC under acidic conditions to afford 6-(2-cyclopropylethyl)-4-hydroxypyridazin-3(2H)-one as a cream solid (14% yield).

$^1$H NMR (400 MHz, MeOH-$d_6$) δ 6.55 (s, 1 H), 2.55-2.63 (m, 2 H), 1.45-1.54 (m, 2 H), 0.67-0.75 (m, 1 H), 0.38-0.42 (m, 2 H) and −0.04-0.06 (m, 2 H)

MS ES$^+$: 181.

Example 15

6-(2-Cyclopentylethyl)-4-hydroxypyridazin-3(2H)-one

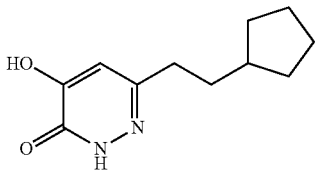 [SMILES: O=c1[nH]nc(CCC2CCCC2)cc1O]

Prepared as described for 4-hydroxy-6-(2-phenethyl)pyridazin-3(2H)-one (Example 1) from 3,4-bis(benzyloxy)-6-(cyclopentylethynyl)pyridazine (Intermediate 19) except that the reaction was carried out in a mixture of methanol and tetrahydrofuran (1:1). The resulting crude product was purified by preparative HPLC under acidic conditions to afford 6-(2-cyclopentylethyl)-4-hydroxypyridazin-3(2H)-one after recrystallisation from ethanol and heptane as a white solid (51% yield).

$^1$H NMR (400 MHz, DMSO-$d_6$) δ 12.63 (br s, 1 H), 10.67 (br s, 1 H), 6.54 (s, 1 H), 2.41-2.48 (m, 2 H), 1.67-1.79 (m, 3 H), 1.41-1.63 (m, 6 H), 1.00-1.15 (m, 2 H).

MS ES$^+$: 209.

Example 16

4-Hydroxy-6-[2-(4-methoxycyclohexyl)ethyl]pyridazin-3(2H)-one

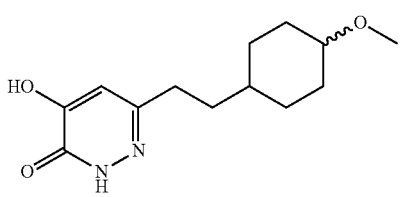 [SMILES: COC1CCC(CCc2cc(O)c(=O)[nH]n2)CC1]

Prepared as described for 4-hydroxy-6-(2-phenethyl)pyridazin-3(2H)-one (Example 1) from 3,4-bis(benzyloxy)-6-[(4-methoxycyclohex-1-en-1-yl)ethynyl]pyridazine (Intermediate 20) except that the reaction was carried out in methanol. The resulting crude product was purified by preparative HPLC under acidic conditions to afford 4-hydroxy-6-[2-(4-methoxycyclohexyl)ethyl]pyridazin-3(2H)-one (mixture of isomers) as a white solid (26% yield).

$^1$H NMR (400 MHz, DMSO-$d_6$) δ 12.62 (s, 1 H), 10.66 (br s, 1 H), 6.52-6.55 (m, 1 H), 3.21 and 3.18 (2 singlets, total 3 H), 2.97-3.08 (m, 1 H), 2.40-2.47 (m, 2 H), 1.91-2.01 (m, 1 H), 1.70-1.80 (m, 2 H), 0.84-1.51 (m, 8 H)

MS ES$^+$: 253.

Example 17

6-[2-(2,4-Difluorophenyl)ethyl]-4-hydroxypyridazin-3(2H)-one

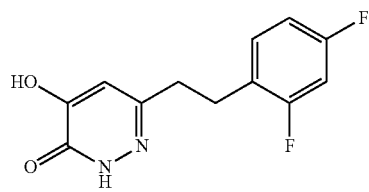 [SMILES: O=c1[nH]nc(CCc2ccc(F)cc2F)cc1O]

Prepared as described for 4-hydroxy-6-(2-phenethyl)pyridazin-3(2H)-one (Example 1) from 3,4-bis(benzyloxy)-6-[(2,4-difluorophenyl)ethynyl]pyridazine (Intermediate 21) except that the reaction was carried out in a mixture of ethanol and tetrahydrofuran (1:1). The crude material was purified by reverse phase chromatography (25 g C18) cartridge eluting with 5-100% acetonitrile/water with acidic modifier and the appropriate fractions combined to give a yellow solid. This was recrystallised from ethanol to give a white solid (yield=26%).

$^1$H NMR (400 MHz, DMSO-$d_6$) δ 12.69 (s, 1 H), 10.78 (br s, 1 H), 7.24-7.40 (m, 1 H), 7.09-7.26 (m, 1 H), 6.93-7.07 (m, 1 H), 6.58 (s, 1 H), 2.82-2.97 (m, 2 H), 2.63-2.80 (m, 2 H).

MS ES$^+$: 253.

Example 18

6-{2-[3-(Difluoromethyl)phenyl]ethyl}-4-hydroxypyridazin-3(2H)-one

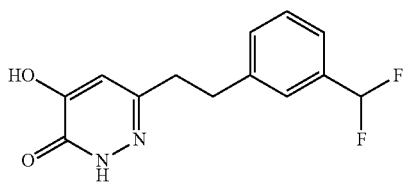 [SMILES: O=c1[nH]nc(CCc2cccc(C(F)F)c2)cc1O]

Prepared as described for 4-hydroxy-6-(2-phenethyl)pyridazin-3(2H)-one (Example 1) from 3,4-bis(benzyloxy)-6-[(3-(difluoromethyl)phenyl)ethynyl]pyridazine (Intermediate 22) except that the reaction was carried out in a mixture of ethanol and tetrahydrofuran (1:1). The crude material was purified by reverse phase chromatography (25 g C18) cartridge eluting with 5.100% acetonitrile/water with acidic modifier and the appropriate fractions combined to give a pale orange solid (yield=32%).

$^1$H NMR (400 MHz, DMSO-d$_6$) δ 12.69 (s, 1 H), 10.77 (br s, 1 H), 7.33-7.47 (m, 5 H), 6.79-7.18 (m, 1 H), 6.61 (s, 1 H), 2.89-3.00 (m, 2 H), 2.71-2.83 (m, 2 H).

MS ES$^+$: 267.

Example 19

6-Benzyl-4-hydroxypyridazin-3(2H)-one

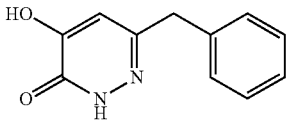 [SMILES: O=c1[nH]nc(Cc2ccccc2)cc1O]

To a degassed solution of 6-benzyl-3,4-bis(benzyloxy)pyridazine (Intermediate 23: 0.16 g, 0.418 mmol) in methanol (4.18 ml) was added 10% palladium on carbon (0.045 g, 0.042 mmol). The mixture was degassed, evacuated and filled with hydrogen from a balloon. After 1 hour the reaction mixture was degassed and filtered through a pad of "Celite" diatomaceous earth, washing with methanol and concentrated to give a yellow oil. The crude oil was purified by reverse phase chromatography (25 g C18) cartridge eluting with 5-100% acetonitrile/water with acidic modifier and the appropriate fractions combined to give a cream solid (yield=77%).

$^1$H NMR (400 MHz, DMSO-d$_6$) δ 12.72 (br s, 1 H), 10.78 (br s, 1 H), 7.15-7.40 (m, 5 H), 6.46 (s, 1 H), 3.79 (s, 2 H).

MS ES$^+$: 203.

Example 20

6-[2-(3-Chlorophenyl)ethyl]-4-hydroxypyridazin-3(2H)-one

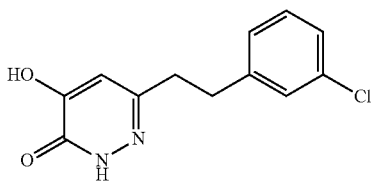 [SMILES: O=c1[nH]nc(CCc2cccc(Cl)c2)cc1O]

Prepared as described for 4-hydroxy-6-(2-phenethyl)pyridazin-3(2H)-one (Example 1) from 3,4-bis(benzyloxy)-6-[(3-chloromethyl)phenyl)ethynyl]pyridazine (Intermediate purified by reverse phase chromatography (50 g C18) cartridge eluting with 5-100% acetonitrile/water with acidic modifier and the appropriate fractions combined to give an orange solid. This was recrystallised from ethyl acetate to give a white solid (yield=32%).

$^1$H NMR (400 MHz, DMSO-d$_6$) δ 12.67 (s, 1 H), 10.72 (br s, 1 H), 7.10-7.40 (m, 4 H), 6.60 (s, 1 H), 2.82-3.05 (m, 2 H), 2.71-2.82 (m, 2 H).

MS ES$^+$: 251.

Example 21

4-Hydroxy-6-(1-phenylcyclopropyl)pyridazin-3(2H)-one

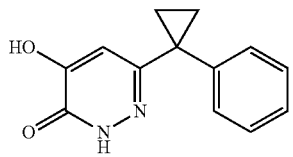 [SMILES: O=c1[nH]nc(C2(c3ccccc3)CC2)cc1O]

Prepared as described for 4-hydroxy-6-(2-phenethyl)pyridazin-3(2H)-one (Example 1) from 3,4-bis(benzyloxy)-6-(1-phenylcyclopropyl)pyridazine (Intermediate 26) except that the reaction was carried out in ethyl acetate. The crude material was recrystallised from ethyl acetate to give a pink solid (yield=27%).

$^1$H NMR (400 MHz, DMSO-d$_6$) δ 12.69 (s, 1 H), 10.74 (br s, 1 H), 7.13-7.39 (m, 5 H), 6.32 (s, 1 H), 1.27-1.39 (m, 2 H), 1.10-1.24 (m, 2 H).

MS ES$^+$: 229.

Example 22

4-[2-(5-Hydroxy-6-oxo-1,6-dihydropyridazin-3-yl)ethyl]benzonitrile

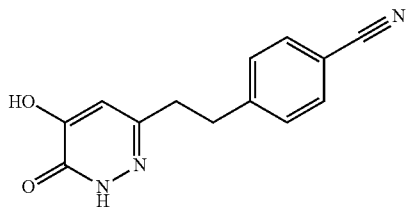 [SMILES: N#Cc1ccc(CCc2cc(O)c(=O)[nH]n2)cc1]

Prepared by the same method as for 4-hydroxy-6-(2-phenylethyl)pyridazin-3(2H)-one (Example 1) from 4-{2-[5,6-bis(benzyloxy)pyridazin-3-yl]ethynyl}benzonitrile (Intermediate 27) except that the solvent mixture used for the hydrogenation was made up from tetrahydrofuran and methanol (1:1) and the final compound was recrystallised from tetrahydrofuran.

$^1$H NMR (400 MHz, DMSO-d$_6$) δ 12.59 (br a, 1 H), 10.66 (br s, 1 H), 7.56-7.78 (m, 2 H), 7.27-7.44 (m, 2 H), 6.52 (s, 1 H), 2.82-3.01 (m, 2 H) and 2.56-2.82 (m, 2 H).

MS ES$^+$: 242.

Example 23

6-[2-(3-Fluoro-4-methylphenyl)ethyl]-4-hydroxy-pyridazin-3(2H)-one

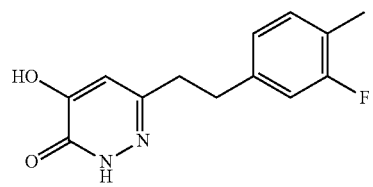 [SMILES: Cc1ccc(CCc2cc(O)c(=O)[nH]n2)cc1F]

Prepared by the same method as for 4-hydroxy-6-(2-phenylethyl)pyridazin-3(2H)-one (Example 1) from 3,4-bis(benzyloxy)-6-[2-(3-fluoro-4-methylphenyl)ethynyl]pyridazine (Intermediate 28) except that the solvent mixture used for the hydrogenation was ethyl acetate and methanol (1:1) and the final product was recrystallised from ethyl acetate.

$^1$H NMR (400 MHz, DMSO-$d_6$) δ 12.67 (s, 1 H), 10.71 (br s, 1 H), 7.09-7.24 (m, 1 H), 6.85-7.07 (m, 2 H), 6.59 (s, 1 H), 2.80-2.93 (m, 2 H), 2.68-2.77 (m, 2 H) and 2.18 (s, 3 H).

MS ES$^+$: 249.

Example 24

6-[2-(4-Fluoro-3-methylphenyl)ethyl]-4-hydroxy-pyridazin-3(2H)-one

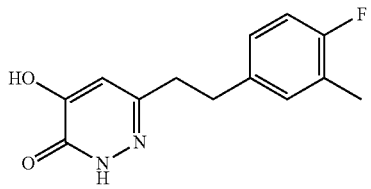 [SMILES: Cc1cc(CCc2cc(O)c(=O)[nH]n2)ccc1F]

Prepared by the same method as for 4-hydroxy-6-(2-phenylethyl)pyridazin-3(2H)-one (Example 1) from 3,4-bis(benzyloxy)-6-[2-(4-fluoro-3-methylphenyl)ethynyl]pyridazine (Intermediate 29) except that the solvent mixture used for the hydrogenation was made up of ethyl acetate and methanol (1:1) and the final material was recrystallised from ethyl acetate.

$^1$H NMR (400 MHz, DMSO-$d_6$) δ 12.67 (s, 1 H), 10.70 (br s, 1 H), 6.90-7.20 (m, 3 H), 6.58 (s, 1 H), 2.61-2.91 (m, 4 H) and 2.20 (s, 3 H).

MS ES$^+$: 249.

Example 25

6-[2-(3,4-Dimethoxyphenyl)ethyl]-4-hydroxy-pyridazin-3(2H)-one

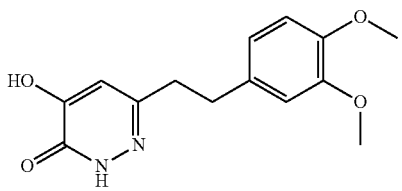 [SMILES: COc1ccc(CCc2cc(O)c(=O)[nH]n2)cc1OC]

Prepared by the same method as for 4-hydroxy-6-(2-phenylethyl)pyridazin-3(2H)-one (Example 1) from 3,4-bis(benzyloxy)-6-[2-(3,4-dimethoxyphenyl)ethynyl]pyridazine (Intermediate 30) except that the solvent mixture used for the hydrogenation was ethanol and tetrahydrofuran (1:1) and the final material was recrystallised from a mixture of ethyl acetate and heptane.

$^1$H NMR (400 MHz, DMSO-$d_6$) δ 12.66 (br s, 1 H), 10.69 (br s, 1 H), 6.76-6.94 (m, 2 H), 6.63-6.77 (m, 1 H), 6.58 (s, 1 H), 3.59-3.82 (m, 6 H) and 2.60-2.91 (m, 4 H).

MS ES$^+$: 277.

Example 26

4-Hydroxy-6-{2-[3-(trifluoromethoxy)phenyl]ethyl}pyridazin-3(2H)-one

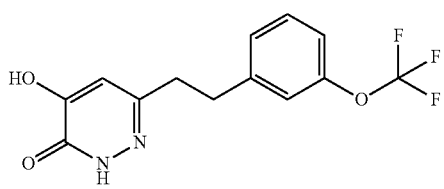 [SMILES: O=c1[nH]nc(CCc2cccc(OC(F)(F)F)c2)cc1O]

Prepared by the same method as for 4-hydroxy-6-(2-phenylethyl)pyridazin-3(2H)-one (Example 1) from 3,4-bis(benzyloxy)-6-((3(trifluoromethoxy)phenyl)ethynyl)pyridazine (Intermediate 39) except that the solvent used for the hydrogenation was ethanol and the final compound was recrystallised from a mixture of ethyl acetate and heptane.

$^1$H NMR (400 MHz, DMSO-$d_6$) δ 12.67 (s, 1 H), 10.71 (br s, 1 H), 7.36-7.45 (m, 1 H), 7.13-7.30 (m, 3 H), 6.60 (s, 1 H), 2.88-2.99 (m, 2 H) and 2.73-2.82 (m, 2 H).

MS ES$^+$: 301.

Example 27

6-[2-(4-Chlorophenyl)ethyl]-4-hydroxypyridazin-3(2H)-one

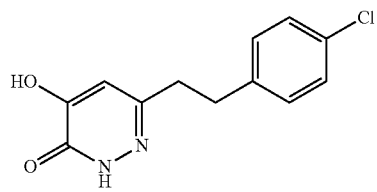 [SMILES: O=c1[nH]nc(CCc2ccc(Cl)cc2)cc1O]

Prepared by the same method as for 4-hydroxy-6-(2-phenylethyl)pyridazin-3(2H)-one (Example 1) from 3,4-bis(benzyloxy)-6-((4-chlorophenyl)ethynyl)pyridazine (Intermediate 34) except that the solvent used for the hydrogenation was tetrahydrofuran and the final compound was recrystallised from a mixture of ethyl acetate and heptane.

$^1$H NMR (400 MHz, DMSO-$d_6$) δ 12.66 (s, 1 H), 10.72 (br s, 1 H), 7.14-7.44 (m, 4 H), 6.58 (s, 1 H), 2.83-2.92 (m, 2 H) and 2.69-2.79 (m, 2 H).

MS ES$^+$: 251, 253.

Example 28

6-[2-(2-Chlorophenyl)ethyl]-4-hydroxypyridazin-3(2H)-one

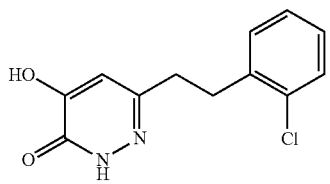 [SMILES: O=c1[nH]nc(CCc2ccccc2Cl)cc1O]

Prepared by the same method as for 4-hydroxy-6-(2-phenylethyl)pyridazin-3(2H)-one (Example 1) from 3,4-bis(benzyloxy)-6-((2-chlorophenyl)ethynyl)pyridazine (Intermediate 35) except that the solvent used for the hydrogenation was ethyl acetate and the final material was recrystallised from a mixture of ethyl acetate and heptane $^1$H NMR (400 MHz, DMSO-$d_6$) δ 12.67 (s, 1 H), 10.73 (br s, 1 H), 7.14-7.46 (m, 4 H), 6.58 (s, 1 H), 2.91-3.05 (m, 2 H) and 2.70-2.81 (m, 2 H).

MS ES$^+$: 251, 253.

Example 29

4-Hydroxy-6-{2-[2-(trifluoromethyl)phenyl]ethyl})pyridazin-3(2H)-one

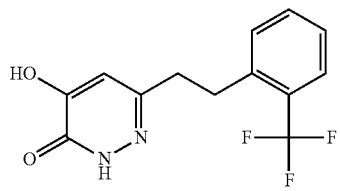 [SMILES: O=c1[nH]nc(CCc2ccccc2C(F)(F)F)cc1O]

Prepared by the same method as for 4-hydroxy-6-(2-phenylethyl)pyridazin-3(2H)-one (Example 1) from 3,4-bis(benzyloxy)-6-((2-trifluoromethylphenyl)ethynyl)pyridazine (Intermediate 40) except that the final product was recrystallised from a mixture of ethyl acetate and heptane.

$^1$H NMR (400 MHz, DMSO-$d_6$) δ 12.66 (br s, 1 H), 10.79 (br s, 1 H), 7.35-7.74 (m, 4 H), 6.56 (s, 1 H), 2.97-3.11 (m, 2 H) and 2.71-2.82 (m, 2 H).

MS ES$^+$: 285.

Example 30

6-(4-(Difluoromethoxy)phenethyl)-4-hydroxy-pyridazin-3(2H)-one

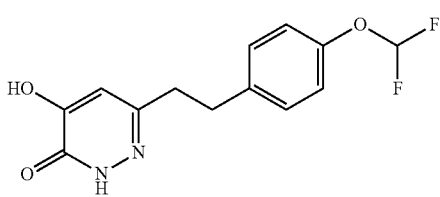 [SMILES: O=c1[nH]nc(CCc2ccc(OC(F)F)cc2)cc1O]

Prepared by the same method as for 4-hydroxy-6-(2-phenylethyl)pyridazin-3(2H)-one (Example 1) from 3,4-bis(benzyloxy)-6-((4-(difluoromethoxy)phenyl)ethynyl)pyridazine (Intermediate 36) except that the solvent mixture used for the hydrogenation was made up of tetrahydrofuran and methanol and the final material was recrystallised from 2-propanol and heptanes.

$^1$H NMR (400 MHz, CD$_2$Cl$_2$) δ 7.17-7.24 (m, 2 H), 7.00-7.11 (m, 2 H), 6.55 (s, 1 H), 6.31-6.74 (m, 1 H), 2.91-3.00 (m, 2 H) and 2.81-2.91 (m, 2 H).

MS ES$^+$ 283.

Example 31

6-(4-(Trifluoromethoxy)phenethyl)-4-hydroxy-pyridazin-3(2H)-one

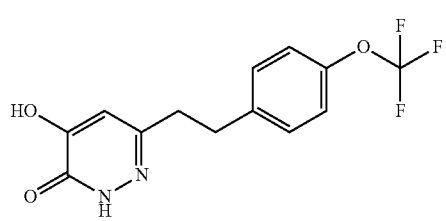 [SMILES: O=c1[nH]nc(CCc2ccc(OC(F)(F)F)cc2)cc1O]

Prepared by the same method as for 4-hydroxy-6-(2-phenylethyl)pyridazin-3(2H)-one (Example 1) from 3,4-bis(benzyloxy)-6-((4-(trifluoromethoxy)phenyl)ethynyl)pyridazine (Intermediate 37) except that the solvent mixture used for the hydrogenation was made up of tetrahydrofuran and methanol and the final compound was recrystallised from MTBE and heptane.

$^1$H NMR (400 MHz, DMSO-$d_6$) δ 12.70 (s, 1 H), 10.75 (br s, 1 H), 7.21-7.41 (m, 4 H), 6.61 (s, 1 H) and 2.67-2.99 (m, 4 H).

MS ES$^+$ 301.

Example 32

6-(3-(Difluoromethoxy)phenethyl)-4-hydroxy-pyridazin-3(2H)-one

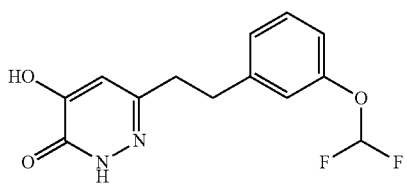 [SMILES: O=c1[nH]nc(CCc2cccc(OC(F)F)c2)cc1O]

Prepared by the same method as for 4-hydroxy-6-(2-phenylethyl)pyridazin-3(2H)-one (Example 1) from 3,4-bis(benzyloxy)-6-((3-(difluoromethoxy)phenyl)ethynyl)pyridazine (Intermediate 38) except that the mixture of solvent mixture used for the hydrogenation was made up of tetrahydrofuran and methanol and the final compound was recrystallised from a mixture of ethanol and heptane.

$^1$H NMR (400 MHz, DMSO-$d_6$) δ 12.65 (br s, 1 H), 6.92-7.43 (m, 6 H), 6.58 (s, 1 H), 2.83-2.97 (m, 2 H) and 2.70-2.84 (m, 2 H).

MS ES$^+$283.

Example 33

6-[1-(4-Fluorophenyl)cyclopropyl]-4-hydroxy-pyridazin-3(2H)-one

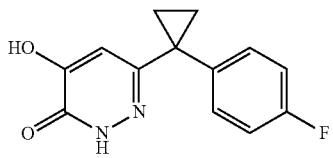 [SMILES: O=c1[nH]nc(C2(c3ccc(F)cc3)CC2)cc1O]

Prepared by the same method as for 4-hydroxy-6-(2-phenylethyl)pyridazin-3(2H)-one (Example 1) from 3,4-bis(benzyloxy)-6-[1-(4-fluorophenyl)cyclopropyl]pyridazine (Intermediate 42) except that the solvent used for the hydrogenation was ethyl acetate and the product was recrystallised from a mixture of ethyl acetate and MTBE.

$^1$H NMR (400 MHz, DMSO-$d_6$) δ 12.69 (s, 1 H), 10.77 (br s, 1 H), 7.26-7.42 (m, 2 H), 7.01-7.26 (m, 2 H), 6.32 (s, 1 H), 1.28-1.39 (m, 2 H) and 1.09-1.22 (m, 2 H).

MS ES$^+$: 247.

Example 34

6-[1-(4-Fluorophenyl)ethyl]-4-hydroxypyridazin-3(2H)-one

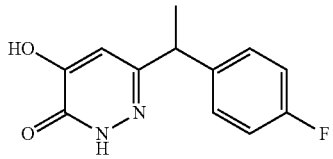 [SMILES: CC(c1ccc(F)cc1)c1cc(O)c(=O)[nH]n1]

Prepared by the same method as for 4-hydroxy-6-(2-phenylethyl)pyridazin-3(2H)-one (Example 1) from 3,4-bis(benzyloxy)-6-(1-phenylethenyl)pyridazine (Intermediate 41) except that the solvent mixture used for the hydrogenation consisted of ethyl acetate and tetrahydrofuran and the product was recrystallised from a mixture of heptane and MTBE.

$^1$H NMR (400 MHz, DMSO-$d_6$) δ 12.75 (s, 1 H), 10.74 (br s, 1 H), 7.24-7.35 (m, 2 H), 7.00-7.19 (m, 2 H), 6.43 (s, 1 H), 3.85-4.13 (m, 1 H) and 1.38-1.55 (m, 3 H).

MS ES$^+$: 235.

Example 35

4-Hydroxy-6-{1-[3-(trifluoremethyl)phenyl]ethyl}pyridazin-3(2H)-one

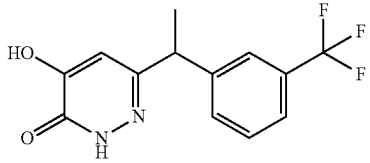 [SMILES: CC(c1cccc(C(F)(F)F)c1)c1cc(O)c(=O)[nH]n1]

Prepared by the same method as for 4-hydroxy-6-(2-phenylethyl)pyridazin-3(2H)-one (Example 1) from 3,4-bis(benzyloxy)-6-(3-methylbut-1-ynyl)pyridazine (Intermediate 43) except that the solvent mixture used for the hydrogenation was made up of ethyl acetate and tetrahydrofuran and the product was recrystallised from heptane and MTBE.

$^1$H NMR (400 MHz, DMSO-$d_6$) δ 12.79 (s, 1H), 10.80 (br. s., 1H), 7.47-7.66 (m, 4H), 6.51 (s, 1H), 4.02-4.25 (m, 1H), 1.41-1.60 (m, 3H)

MS ES$^+$: 285

Example 36

4-Hydroxy-6-{2-[4-(trifluoromethyl)phenyl]ethyl}pyridazin-3(2H)-one

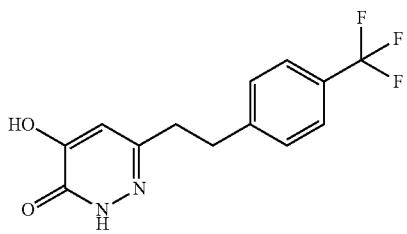 [SMILES: O=c1[nH]nc(CCc2ccc(C(F)(F)F)cc2)cc1O]

Prepared by the same method as for 4-hydroxy-6-(2-phenylethyl)pyridazin-3(2H)-one (Example 1) from (E)-3,4-bis(benzyloxy)-6-(4-(trifluoromethyl)styryl)pyridazine (Intermediate 44) except that the product was recrystallised from a mixture of heptane and ethyl acetate.

$^1$H NMR (400 MHz, DMSO-$d_6$) δ 12.67 (s, 1 H), 10.73 (br s, 1 H), 7.58-7.68 (m, 2 H), 7.40-7.49 (m, 2 H), 6.61 (s, 1 H), 2.92-3.03 (m, 2 H) and 2.72-2.85 (m, 2 H)

MS ES$^+$: 285.

Example 37

6-((Cyclopropylmethyl)(methyl)amino)-4-hydroxy-pyridazin-3(2H)-one

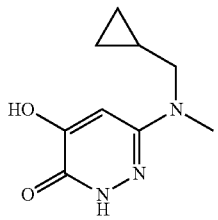

A suspension of 5,6-bis(benzyloxy)-N-(cyclopropylmethyl)-N-methylpyridazin-3, amine (Intermediate 46; 2.44 mmol) and palladium on carbon (10% wt loading, dry basis; 0.259 g, 0.244 mmol) in ethyl acetate (10 ml) was stirred under a hydrogen atmosphere for 2 hours. The reaction mixture was filtered through a diatomaceous earth cartridge commercially sold under the trade mark 'Celite', eluting with ethyl acetate, tetrahydrofuran and methanol. The filtrate was concentrated in vacuo to afford a brown solid, which was triturated from ethyl acetate to give the title compound as a pale brown solid (27.9 mg, 38%).

$^1$H NMR (400 MHz, DMSO-d$_6$) δ 11.81-11.98 (m, 1 H), 6.48 (s, 1 H), 3.12 (d, 2 H), 2.84 (s, 3 H), 0.84-1.01 (m, 1 H), 0.36-0.51 (m, 2 H) and 0.09-0.26 (m, 2H).
MS ES$^+$ 196.

Example 38

6-(((Cyclopropylmethyl)(methyl)amino)-4-hydroxypyridazin-3(2H)-one

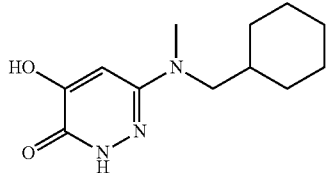 [SMILES: CN(CC1CCCCC1)c1cc(O)c(=O)[nH]n1]

Prepared according to the procedure for 6-((cyclopropylmethyl)(methyl)amino)-4-hydroxypyridazin-3(2H)-one (Example 37) using 5,6-bis(benzyloxy)-N-(cyclohexylmethyl)-N-methylpyridazin-3-amine (Intermediate 47) but purified by reverse phase C18 chromatography, eluting with 5-100% acetonitrile/water with a 0.1% ammonia modifier in both the water and acetonitrile to give the title compound as a pale cream solid (45 mg, 26%).
$^1$H NMR (400 MHz, DMSO-d$_6$) δ ppm 11.88 (br s, 1 H), 6.44 (s, 1 H), 2.98-3.13 (m, 2 H), 2.82 (s, 3 H), 1.52-1.74 (m, 6 H), 1.04-1.26 (m, 3 H) and 0.82-0.99 (m, 2 H).
MS ES+ 238.

Example 39

6-(3-Chlorobenzyl)-4-hydroxypyridazin-3(2H)-one

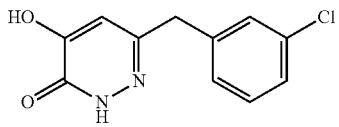 [SMILES: O=c1[nH]nc(Cc2cccc(Cl)c2)cc1O]

Prepared in the same way as 4-hydroxy-6-(2-phenylethyl)pyridazin-3(2H)-one (Example 1) from 3,4-bis(benzyloxy)-6-[(3-chlorophenyl)methyl]pyridazine (Intermediate 48) except that the solvent used for the hydrogenation was ethyl acetate and the product was recrystallised from ethyl acetate.
$^1$H NMR (400 MHz, DMSO-d$_6$) δ 12.75 (s, 1 H), 10.83 (br s, 1 H), 7.15-7.40 (m, 4 H), 6.52 (s, 1 H) and 3.81 (s, 2 H).
MS ES$^+$: 237 and 239.

Example 40

6-(4-Chlorobenzyl)-4-hydroxypyridazin-3(2H)-one

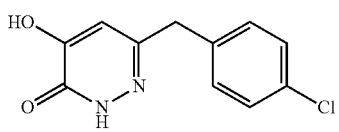 [SMILES: O=c1[nH]nc(Cc2ccc(Cl)cc2)cc1O]

Prepared in the same way as 4-hydroxy-6-(2-phenylethyl)pyridazin-3(2H)-one (Example 1) from 3,4-bis(benzyloxy)-6-[(4-chlorophenyl)methyl]pyridazine (Intermediate 49) except that the solvent used for the hydrogenation was ethyl acetate and tetrahydrofuran and the product was recrystallised from ethyl acetate.
$^1$H NMR (400 MHz, DMSO-d6) δ 12.74 (s, 1 H), 10.81 (br s, 1 H), 7.32-7.45 (m, 2 H), 7.16-7.32 (m, 2 H), 6.48 (s, 1 H) and 3.79 (s, 2 H).
MS ES$^+$: 237 and 239.

Example 41

6-(Cyclohexylmethyl)-4-hydroxypyridazin-3(2H)-one

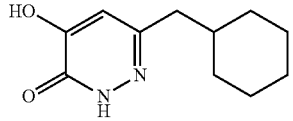 [SMILES: O=c1[nH]nc(CC2CCCCC2)cc1O]

Prepared in the same way as 4-hydroxy-6-(2-phenylethyl)pyridazin-3(2H)-one (Example 1) from 3,4-bis(benzyloxy)-6-(cyclohexylmethyl)pyridazine (Intermediate 50) except that the solvent used for the hydrogenation was ethyl acetate and the product was recrystallised from a mixture of MTBE and heptanes.
$^1$H NMR (400 MHz, DMSO-d$_6$) δ 12.64 (s, 1 H), 10.64 (br s, 1 H), 6.51 (s, 1 H), 2.21-2.39 (m, 2 H), 1.44-1.72 (m, 6 H), 1.03-1.25 (m, 3 H) and 0.75-1.05 (m, 2 H).
MS ES$^+$: 209.

Example 42

6-(4-Fluorobenzyl)-4-hydroxypyridazin-3(2H)-one

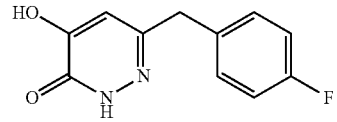 [SMILES: O=c1[nH]nc(Cc2ccc(F)cc2)cc1O]

Prepared in the same way as 4-hydroxy-6-(2-phenylethyl)pyridazin-3(2H)-one (Example 1) from 3,4-bis(benzyloxy)-6-[(4-fluorophenyl)methyl]pyridazine (Intermediate 51) except that the solvent used for the hydrogenation was ethyl acetate and the product was recrystallised from a mixture of MTBE and heptanes.
$^1$H NMR (400 MHz, DMSO-d$_6$) δ 12.73 (s, 1 H), 10.79 (br s, 1 H), 7.22-7.33 (m, 2 H), 6.96-7.18 (m, 2 H), 6.47 (s, 1 H) and 3.79 (s, 2 H).
MS ES$^+$: 221.

Example 43

6-(2-Chloro-6-fluorobenzyl)-4-hydroxypyridazin-3(2H)-one

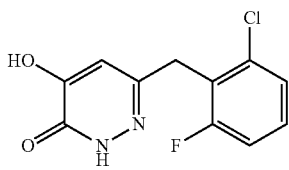 [SMILES: O=c1[nH]nc(Cc2c(F)cccc2Cl)cc1O]

Prepared in the same way as 4-hydroxy-6-(2-phenylethyl)pyridazin-3(2H)-one (Example 1) from 3,4-bis(benzyloxy)-6-[(2-chloro-6-fluorophenyl)methyl]pyridazine (Intermediate 52) except that the solvent used for the hydrogenation was tetrahydrofuran and the product was recrystallised from a mixture of MTBE and heptanes.

$^1$H NMR (400 MHz, DMSO-$d_6$) δ 12.66 (s, 1 H), 10.90 (br s, 1 H), 7.31-7.48 (m, 2), 7.05-7.32 (m, 1 H), 6.55 (s, 1) and 4.00 (s, 2 H).

MS ES$^+$: 255, 257.

Example 44

6-(2-Chlorobenzyl)-4-hydroxypyridazin-3(2H)-one

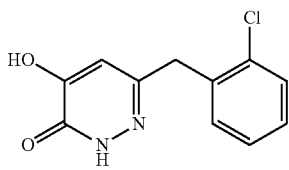

Prepared in the same way as 4-hydroxy-6-(2-phenylethyl)pyridazin-3(2H)-one (Example 1) from 3,4-bis(benzyloxy)-6-[(2-chlorophenyl)methyl]pyridazine (Intermediate 53) except that the solvent used for the hydrogenation was tetrahydrofuran and the product was recrystallised from a mixture of MTBE and heptanes.

$^1$H NMR (400 MHz, DMSO-$d_6$) δ 12.72 (s, 1 H), 10.80 (br s, 1 H), 7.40-7.57 (m, 1 H), 7.20-7.42 (m, 3 H), 6.48 (s, 1 H) and 3.95 (s, 2 H).

MS ES$^+$: 237, 239.

Example 45

6-(3-Fluorobenzyl)-4-hydroxypyridazin-3(2H)-one

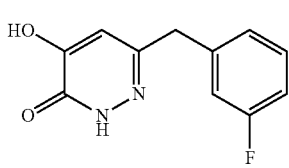 [SMILES: O=c1[nH]nc(Cc2cccc(F)c2)cc1O]

Prepared in the same way as 4-hydroxy-6-(2-phenylethyl)pyridazin-3(2H)-one (Example 1) from 3,4-bis(benzyloxy)-6-[(3-fluorophenyl)methyl]pyridazine (Intermediate 54) except that the solvent used for the hydrogenation was ethanol and the product was recrystallised from a mixture of MTBE and heptanes.

$^1$H NMR (400 MHz, DMSO-$d_6$) δ 12.75 (s, 1 H), 10.82 (br s, 1 H), 7.25-7.44 (m, 1 H), 6.99-7.14 (m, 3 H), 6.41-6.58 (m, 1 H) and 3.68-3.89 (m, 2 H).

MS ES$^+$: 221.

Example 46

6-(2-Fluorobenzyl)-4-hydroxypyridazin-3(2H)-one

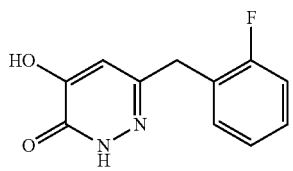 [SMILES: O=c1[nH]nc(Cc2ccccc2F)cc1O]

Prepared in the same way as 4-hydroxy-6-(2-phenylethyl)pyridazin-3(2H)-one (Example 1) from 3,4-bis(benzyloxy)-6-[(2-fluorophenyl)methyl]pyridazine (Intermediate 55) except that the product was recrystallised from a mixture of ethyl acetate and heptanes.

$^1$H NMR (400 MHz, DMSO-$d_6$) δ 12.71 (br s, 1 H), 10.85 (br s, 1 H), 7.26-7.37 (m, 2 H), 7.12-7.22 (m, 2 H), 6.48 (s, 1 H) and 3.85 (s, 2 H).

MS ES$^+$: 221.

Example 47

6-(4-Methylbenzyl)-4-hydroxypyridazin-3(2H)-one

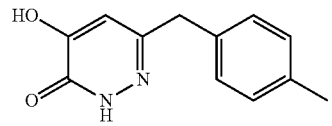 [SMILES: Cc1ccc(Cc2cc(O)c(=O)[nH]n2)cc1]

Prepared in the same way as 4-hydroxy-6-(2-phenylethyl)pyridazin-3(2H)-one (Example 1) from 3,4-bis(benzyloxy)-6-[(4-methylphenyl)methyl]pyridazine (Intermediate 56) except that the solvent mixture used for the hydrogenation was made up of tetrahydrofuran and ethyl acetate and the product was recrystallised from a mixture of ethyl acetate and heptanes.

$^1$H NMR (400 MHz, DMSO-$d_6$) δ 12.70 (br s, 1 H), 10.75 (br s, 1 H), 7.12 (s, 4 H), 6.42 (s, 1 H), 3.64-3.82 (s, 2 H) and 2.26 (s, 3 H).

MS ES$^+$: 217.

Example 48

6-(3-Methylbenzyl)-4-hydroxypyridazin-3(2H)-one

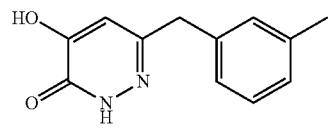 [SMILES: Cc1cccc(Cc2cc(O)c(=O)[nH]n2)c1]

Prepared in the same way as 4-hydroxy-6-(2-phenylethyl)pyridazin-3(2H)-one (Example 1) from 3,4-bis(benzyloxy)-6-[(3-methylphenyl)methyl]pyridazine (Intermediate 57) except that the solvent mixture used for the hydrogenation was made up from tetrahydrofuran and ethyl acetate and the product was recrystallised from a mixture of ethyl acetate and heptane.

$^1$H NMR (400 MHz, DMSO-$d_6$) δ 12.71 (br s, 1 H), 10.78 (br s, 1 H), 7.14-7.25 (m, 1 H), 6.96-7.10 (m, 3 H), 6.44 (s, 1 H), 3.74 (s, 2 H) and 2.17-2.35 (m, 3 H).
MS ES$^+$: 217.

Example 49

4-Hydroxy-6-(3-(trifluoromethyl)benzyl)pyridazin-3(2H)-one

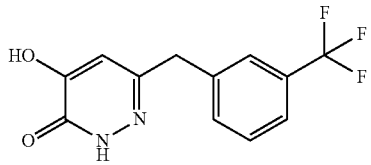 [SMILES: O=c1[nH]nc(Cc2cccc(C(F)(F)F)c2)cc1O]

Prepared in the same way as 4-hydroxy-6-(2-phenylethyl)pyridazin-3(2H)-one (Example 1) from 3,4-bis(benzyloxy)-6-(3-(trifluoromethyl)benzyl)pyridazine (Intermediate 58) except that the solvent used for the hydrogenation was ethyl acetate and the product was recrystallised from a mixture of ethyl acetate and heptanes.

1H NMR (400 MHz, CD$_2$Cl$_2$) δ ppm 10.68 (br s, 1 H), 7.40-7.70 (m, 4 H), 6.56 (s, 1 H) and 3.99 (s, 2 H).
MS ES$^+$ 271.

Example 50

4-Hydroxy-6-{2-[5-(trifluoromethyl)pyridin-3-yl]ethyl}pyridazin-3(2H)-one

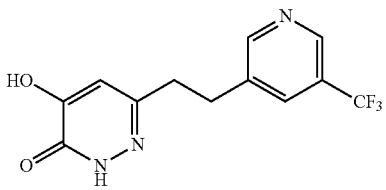 [SMILES: O=c1[nH]nc(CCc2cncc(C(F)(F)F)c2)cc1O]

3,4-bis(Benzyloxy)-6-{2-[5-(trifluoromethyl)pyridin-3-yl]ethynyl}pyridazine (Intermediate 31; 1.5 g, 3.25 mmol) was dissolved in methanol (10 mL) and 10% palladium on carbon (0.04 g) was added before the mixture was purged and subjected to hydrogen gas. The reaction mixture was stirred for 30 min at room temperature under a hydrogen atmosphere. The reaction mass was then filtered through a celite bed under nitrogen atmosphere and washed with methanol. The filtrate was concentrated in vacuo before the crude was re-dissolved in methanol (10 mL) and 10% palladium on carbon (0.04 g) was added before the mixture was purged and subjected to a pressure of hydrogen gas (200 psi), stirring at room temperature overnight. Upon completion the resulting mixture was filtered through celite under nitrogen and washed with methanol. The filtrate was concentrated under vacuum to afford the crude compound (0.2 g) which was then purified by the preparative HPLC to yield 4-hydroxy-6-(2-(5-(trifluoromethyl)pyridin-3-yl)ethyl)pyridazin-3(2H)-one (0.03 g, 82% yield).

$^1$H NMR (400 MHz, DMSO-$d_6$) δ 12.72 (s, 1 H), 10.82 (s, 1 H), 8.75-8.80 (d, 2 H), 8.10 (s, 1 H), 6.63 (s, 1 H), 3.30-3.04 (t, 2 H) and 2.81-2.85 (t, 2 H).
LC-MS ES$^+$: 286.

Example 51

4-Hydroxy-6-[2-(oxan-4-yl)ethyl]pyridazin-3(2H)-one

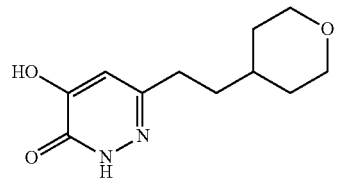

Prepared in the same way as 4-hydroxy-6-(2-phenylethyl)pyridazin-3(2H)-one (Example 1) from 3,4-bis(benzyloxy)-6-[2-(3,6-dihydro-2H-pyran-4-yl)ethynyl]pyridazine (Intermediate 60) except that the pressure of hydrogen gas was 200 psi at room temperature overnight and the solvent used for the hydrogenation was methanol and the product was purified by column chromatography (silica gel, eluting with 0-5% methanol in dichloromethane to afford the title compound (0.1 g, 16% yield).

$^1$H NMR (400 MHz, DMSO-$d_6$) δ 12.67 (s, 1 H), 10.72 (s, 1 H), 6.56 (s, 1 H), 3.802-3.84 (q, 2 H), 3.22-3.34 (q, 2 H), 1.57-1.60 (d, 2 H), 1.43-1.52 (m, 4 H) and 1.19-1.24 (m, 3 H).
LC-MS ES$^+$: 225.

Example 52

6-{[(4-Fluorophenyl)methyl](methyl)amino}-4-hydroxy-pyridazin-3(2H)-one

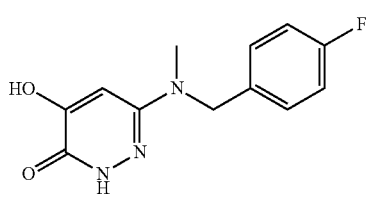

Prepared in the same way as 4-hydroxy-6-(2-phenylethyl)pyridazin-3(2H)-one (Example 1) from 5,6-bis(benzyloxy)-N-[(4-fluorophenyl)methyl]-N-methylpyridazin-3-amine (Intermediate 61) except that the solvent used for the hydrogenation was methanol and the product was purified by triturating in n-pentane (0.15 g, 52% yield)

$^1$H NMR (400 MHz, DMSO-$d_6$) δ 12.07 (s, 1 H), 10.6 (s, 1 H), 7.2-7.34 (m, 2 H), 7.12-7.18 (m, 2H), 4.49 (s, 2 H) and 2.84 (s, 3 H).
LC-MS ES$^+$: 250.

Example 53

6-[2-(2,6-Difluorophenyl)ethyl]-4-hydroxy-pyridazin-3(2H)-one

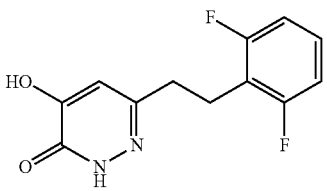 [SMILES: O=c1[nH]nc(CCc2c(F)cccc2F)cc1O]

Prepared by the same method as for 4-hydroxy-6-(2-phenylethyl)pyridazin-3(2H)-one (Example 1) from 3,4-bis(benzyloxy)-6-[2-(2,6-difluorophenyl)ethynyl]pyridazine (Intermediate 33) except that the solvent mixture used for the hydrogenation was methanol and the final material was purified by preparative HPLC (0.035 g, 24.8% yield).

$^1$H NMR (400 MHz, DMSO-$d_6$) δ 12.68 (s, 1 H), 10.78 (s, 1 H), 7.27-7.35 (m, 1 H), 7.03-7.07 (m, 2 H), 6.55 (s, 1 H), 2.90-2.94 (t, 2 H) and 2.69-2.73 (t, 2 H).

LC-MS ES$^+$: 253.

Example 54

6-[2-(2-Chloro-6-fluorophenyl)ethyl]-4-hydroxy-pyridazin-3(2H)-one

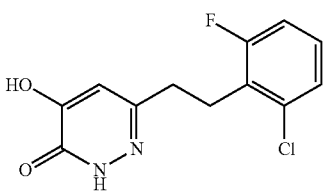 [SMILES: O=c1[nH]nc(CCc2c(F)cccc2Cl)cc1O]

Prepared by the same method as for 4-hydroxy-6-(2-phenylethyl)pyridazin-3(2H)-one (Example 1) from 3,4-bis(benzyloxy)-6-[2-(2-chloro-6-fluorophenyl)ethynyl]pyridazine (Intermediate 32) except that the catalyst used for the hydrogenation was platinum oxide and the solvent was methanol and the final material was purified by preparative HPLC (0.035 g, 24.8% yield).

$^1$H NMR (400 MHz, DMSO-d) δ 12.68 (s, 1 H), 10.78 (s, 1 H), 7.27-7.35 (m, 1 H), 7.03-7.07 (m, 2 H), 6.55 (s, 1 H), 2.90-2.94 (t, 2 H) and 2.69-2.73 (t, 2 H).

LC-MS ES$^+$: 253.

Example 55

6-{[3,5-bis(Trifluoromethyl)phenyl]methyl}-4-hydroxypyridazin-3(2H)-one

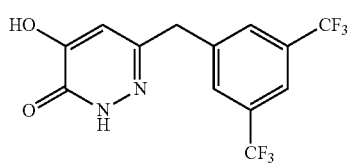 [SMILES: O=c1[nH]nc(Cc2cc(C(F)(F)F)cc(C(F)(F)F)c2)cc1O]

Prepared by the same method as for 4-hydroxy-6-(2-phenylethyl)pyridazin-3(2H)-one (Example 1) from 3,4-bis(benzyloxy)-6-{[3,5-bis(trifluoromethyl)phenyl]methyl}pyridazine (Intermediate 58a) except that the solvent used for the hydrogenation was tetrahydrofuran and the final compound was recrystallised from a mixture of ethyl acetate and heptanes (27% yield).

$^1$H NMR (400 MHz, DMSO-$d_6$) δ 12.80 (br s, 1 H), 10.95 (br s, 1 H), 7.93-8.02 (m, 3 H), 6.60 (s, 1 H) and 4.05 (s, 2 H).

MS ES$^+$: 339.

Example 56

6-(1-Phenylethyl)-4-hydroxypyridazin-3(2H)-one

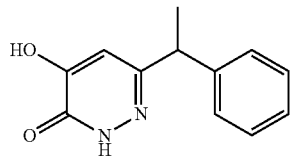 [SMILES: CC(c1ccccc1)c1cc(O)c(=O)[nH]n1]

Prepared by the same method as for 4-hydroxy-6-(2-phenylethyl)pyridazin-3(2H)-one (Example 1) from 3,4-bis(benzyloxy)-6-(1-phenylethenyl)pyridazine (Intermediate 25) except that upon completion of the reaction the resulting mixture was filtered through Celite washing with ethanol and then concentrated in vacuo to afford an orange solid. This was purified initially by eluting on a reverse phase C18 chromatography column (0-60% methanol in water with an acidic modifier) and upon combining and concentrating the appropriate fractions the crude product was recrystallised from a mixture of ethyl acetate and heptanes to afford a white solid and the final compound was recrystallised from a mixture of ethyl acetate and heptanes (32% yield).

$^1$H NMR (400 MHz. DMSO-$d_6$) δ 12.90 (br s, 1 H), 10.80 (br s, 1 H), 7.13-7.35 (m, 6 H), 3.99 (q, 1 H) and 1.47 (d, 3 H).

MS ES$^+$: 217.

Example 57

6-(Cyclopropylmethyl)-4-hydroxy-2,3-dihydro-pyridazin-3-one

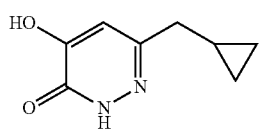

Prepared in the same manner as 4-hydroxy-6-(2-phenylethyl)pyridazin-3(2H)-one (Example 1) from 3,4-bis(benzyloxy)-6-(cyclopropylidenemethyl)pyridazine (Intermediate 65) except that methanol was used as the reaction solvent. The crude compound was purified by preparative HPLC to yield 6-(cyclopropylmethyl)-4-hydroxypyridazin-3(2H)-one (46% yield)

$^1$H NMR (DMSO-$d_6$): δ 12.69 (s, 1 H), 10.75 (s, 1 H), 6.63 (s, 1 H), 2.09-2.34 (d, 2 H), 0.89-0.99 (m, 1 H), 0.43-0.49 (in, 2 H) and 0.16-0.17 (m, 2 H).

LC-MS ES$^+$: 167.

Example 58

4-Hydroxy-6-{1-[4-((trifluoromethyl)phenyl]cyclopropyl}-2,3-dihydropyridazin-3-one

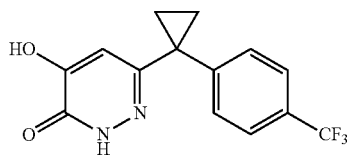 [SMILES: O=c1[nH]nc(C2(c3ccc(C(F)(F)F)cc3)CC2)cc1O]

Prepared in the same manner as 4-hydroxy-6-(2-phenylethyl)pyridazin-3(2H)-one (Example 1) from 3,4-bis(benzyloxy)-6-{1-[4-(trifluoromethyl)phenyl]-cyclopropyl}-pyridazine (Intermediate 68) in 20% yield.

$^1$H NMR (DMSO-d$_6$) δ 12.76 (s, 1 H), 10.87 (br. s., 1 H) 7.67 (m, 2 H), 7.47 (m, 2 H), 6.37 (s, 1 H), 1.38-1.42 (m, 2 H) and 1.23-1.28 (m, 2 H).

MS: ES$^+$: 297.

Example 59

6-{2-[2-Chloro-4-(trifluoromethyl)phenyl]ethyl}-4-hydroxy-2,3-dihydropyridazin-3-one

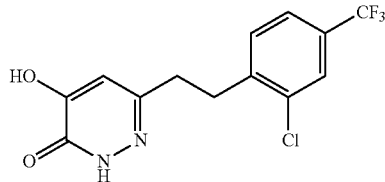 [SMILES: O=c1[nH]nc(CCc2ccc(C(F)(F)F)cc2Cl)cc1O]

Prepared as described for 4-hydroxy-6-(2-phenylethyl) pyridazin-3(2H)-one (Example 1) from 3,4-bis(benzyloxy)-6-{2-[2-chloro-4-(trifluoromethyl)phenyl]-ethynyl}pyridazine (Intermediate 69) in 11% yield.

$^1$H NMR (DMSO-d$_6$) δ 12.68 (s, 1 H), 10.78 (br. s., 1 H), 7.83 (s, 1 H), 7.64-7.68 (m, 1 H), 7.55-7.59 (m, 1 H), 6.61 (s, 1 H), 3.05-3.11 (m, 2 H) and 2.80 (m, 2 H).

MS: ES$^+$: 319.

Example 60

6-{2-[2-Fluoro-4-(trifluoromethyl)phenyl]ethyl}-4-hydroxy-2,3-dihydropyridazin-3-one

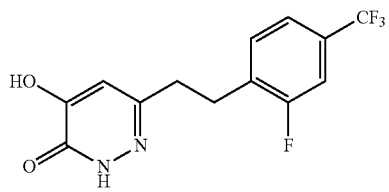 [SMILES: O=c1[nH]nc(CCc2ccc(C(F)(F)F)cc2F)cc1O]

Prepared as described for 4-hydroxy-6-(2-phenylethyl) pyridazin-3(2H)-one (Example 1) from 3,4-bis(benzyloxy)-6-{2-[2-fluoro-4-(trifluoromethyl)phenyl]-ethynyl}pyridazine (Intermediate 70) except that THF was used as the solvent. The reaction was filtered through diatomaceous earth flushing with further tetrahydrofuran and concentrated in vacuo. The residue was purified by column chromatography (silica C18 cartridge; eluting with 0-65% acetonitrile in water with acid modifier). The appropriate fractions were combined and concentrated in vacuo to remove the acetonitrile before the aqueous portion was extracted with ethyl acetate (×2), dried (MgSO$_4$) and concentrated in vacuo. The resulting solid was recrystallised from a mixture of methyl tert-butyl ether and heptane to afford 6-{2-[2-fluoro-4-(trifluoromethyl)phenyl]ethyl}-4-hydroxy-2,3-dihydropyridazin-3-one as a cream solid (29% yield).

$^1$H NMR (DMSO-d$_6$) δ 12.67 (s, 1 H), 10.76 (br. s., 1 H), 7.60 (m, 1 H), 7.48-7.57 (m, 2 H), 6.61 (s, 1 H), 2.95-3.04 (m, 2 H) and 2.75-2.83 (m, 2 H)

MS: ES$^+$: 303.

Example 61

6-{2-[3,5-bis(Trifluoromethyl)phenyl]ethyl}-4-hydroxy-2,3-dihydropyridazin-3-one

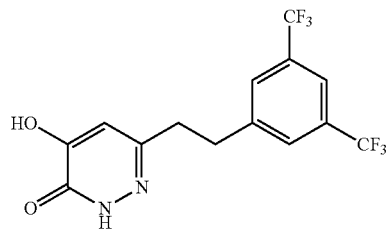 [SMILES: O=c1[nH]nc(CCc2cc(C(F)(F)F)cc(C(F)(F)F)c2)cc1O]

Prepared as described for 4-hydroxy-6-(2-phenylethyl) pyridazin-3(2H)-one (Example 1) from 3,4-bis(benzyloxy)-6-[(E)-2-[3,5-bis(trifluoromethyl)phenyl]-ethenyl] pyridazine (Intermediate 71) in 49% yield.

$^1$H NMR (DMSO-d$_6$) δ 12.69 (s, 1 H), 10.75 (br. s., 1 H), 7.96 (s, 2 H), 7.91 (s, 1 H), 6.64 (s, 1 H), 3.06-3.14 (m, 2 H) and 2.84 (m, 2 H)

MS: ES$^+$: 353.

Example 62

6-{2-[2,4-bis(Trifluoromethyl)phenyl]ethyl}-4-hydroxy-2,3-dihydro-pyridazin-3-one

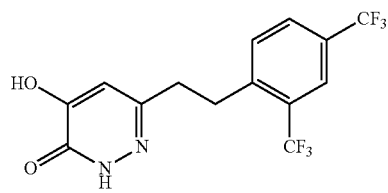 [SMILES: O=c1[nH]nc(CCc2ccc(C(F)(F)F)cc2C(F)(F)F)cc1O]

Prepared as described for 4-hydroxy-6-(2-phenylethyl) pyridazin-3(2H)-one (Example 1) from 3,4-bis(benzyloxy)-6-[(E)-2-[2,4-bis(trifluoromethyl)phenyl]-ethenyl] pyridazine (Intermediate 72) in 31% yield.

$^1$H NMR (DMSO-4) δ 12.71 (s, 1 H), 10.80 (br. s., 1 H), 8.03 (m, 1 H), 7.97 (s, 1 H), 7.79 (m, 1 H), 6.62 (s, 1 H), 3.14 (m, 2 H), 2.77-2.86 (m, 2 H)

MS: ES$^+$: 353.

Example 63

6-{2-[3,4-bis(Trifluoromethyl)phenyl]ethyl}-4-hydroxy-2,3-dihydropyridazin-3-one

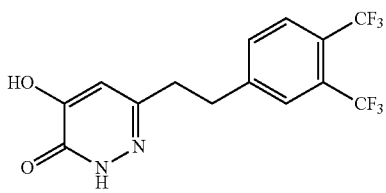 [SMILES: O=c1[nH]nc(CCc2ccc(C(F)(F)F)c(C(F)(F)F)c2)cc1O]

To a solution of 3,4-bis(benzyloxy)-6-[(E)-2-[3,4-bis(trifluoromethyl)phenyl]-ethenyl]pyridazine (Intermediate 73, 227 mg, 0.428 mmol) in THF (4279 µl) was added palladium on carbon (45.5 mg, 0.043 mmol) and the reaction vessel evacuated and purged with nitrogen (×3). The reaction was stirred under a hydrogen atmosphere for 4 hours and the resulting mixture was filtered through a short pad of diatomacious earth and concentrated in vacuo. The residue was purified by chromatography (C18 silica cartridge eluting with 0-50% acetonitrile in water with basic modifier). The appropriate fractions were combined and concentrated to remove the organics and the aqueous fractions were acidified with hydrochloric acid (2 N) and extracted with ethyl acetate (×2), dried (MgSO$_4$) and concentrated in vacuo to yield 6-{2-[3,4-bis(trifluoromethyl)phenyl]ethyl}-4-hydroxy-2,3-dihydropyridazin-3-one as a cream solid (39 mg, 26%)

$^1$H NMR (DMSO-d$_6$) δ 12.69 (s, 1 H), 10.76 (br. s., 1 H), 7.95 (m, 1 H), 7.88-7.93 (m, 1 H), 7.76 (m, 1 H), 6.65 (s, 1 H), 3.04-3.12 (m, 2 H) and 2.83 (m, 2 H).

MS: ES$^+$: 353

Example 64

4-Hydroxy-6-(3-methyl-4-(trifluoromethyl)phenethyl)pyridazin-3(2H)-one

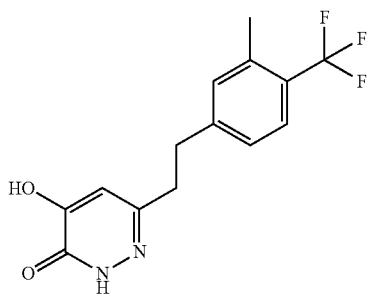 [SMILES: Cc1cc(CCc2cc(O)c(=O)[nH]n2)ccc1C(F)(F)F]

Prepared as described for 4-hydroxy-6-(2-phenylethyl)pyridazin-3(2H)-one (Example 1) from 3,4-bis(benzyloxy)-6-((3-methyl-4-(trifluoromethyl)phenyl)-ethynyl)pyridazine (Intermediate 74) except THF was used as the solvent. The reaction mixture was filtered through a diatomacious earth cartridge, eluting with further THF and methanol. The filtrate was concentrated under reduced pressure and purified by reverse phase column chromatography (eluting with 5-100% aqueous acetonitrile with acid modifier). The desired fractions were combined and freeze dried to give a pale yellow solid, which was recrystallised from methyl tert-butyl ether to give a white solid. The filtrate was concentrated under reduced pressure, and the filtrate and crystals purified separately by preparative HPLC. The two batches were combined and recrystallised from a mixture of methyl tert-butyl ether and ethyl acetate to afford 4-hydroxy-6-(3-methyl-4-(trifluoromethyl)-phenethyl)pyridazin-3 (2H)-one as a white solid (31 mg, 4%).

$^1$H NMR (CD$_3$OD) δ 7.51 (d, 1 H), 7.22 (s, 1 H), 7.16 (d, 1 H), 6.57 (s, 1 H), 2.94-3.02 (m, 2 H), 2.81-2.90 (m, 2 H) and 2.44 (s, 3 H).

MS ES$^+$: 299

M. p.=174-175° C.

Example 65

3,4-bis(Benzyloxy)-6-((3-chloro-4-(trifluoromethyl)phenyl)ethyl)-pyridazine

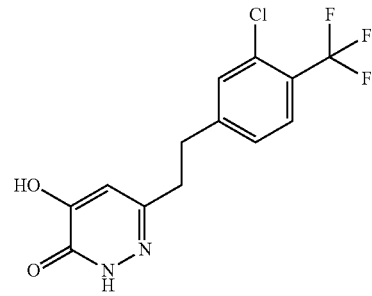 [SMILES: O=c1[nH]nc(CCc2ccc(C(F)(F)F)c(Cl)c2)cc1O]

Prepared as described for 4-hydroxy-6-(2-phenylethyl)pyridazin-3(2H)-one (Example 1) from 3,4-bis(benzyloxy)-6-{2-[3-chloro-4-(trifluoromethyl)phenyl]-ethynyl}pyridazine (Intermediate 75) except that THF was used as the solvent. The crude product was purified by reverse phase chromatography (eluting with 5-100% acetonitrile in water with acid modifier) to give a pale yellow solid. The solid was recrystallised from a mixture of methyl tert-butyl ether and ethyl acetate to afford 3,4-bis(benzyloxy)-6-((3-chloro-4-(trifluoromethyl)phenyl)ethyl)-pyridazine as a white solid (0.182 g, 17%).

$^1$H NMR (CD$_3$OD) δ 7.67 (d, 1 H), 7.50 (s, 1 H), 7.33 (d, 1 H), 6.63 (s, 1 H), 3.00-3.09 (m, 2 H) and 2.85-2.93 (m, 2 H).

MS ES$^+$: 319.

M. p.=169-170° C.

Example 66

4-Hydroxy-6-{2-[2-methyl-4-(trifluoromethyl)phenyl]ethyl}-2,3-dihydropyridazin-3-one

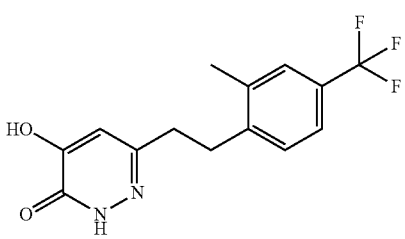 [SMILES: Cc1cc(C(F)(F)F)ccc1CCc1cc(O)c(=O)[nH]n1]

Prepared as described for 4-hydroxy-6-(2-phenylethyl)pyridazin-3(2H)-one (Example 1) from 3,4-bis(benzyloxy)-6-[(E)-2-[2-methyl-4-(trifluoromethyl)phenyl]-ethenyl]

pyridazine (Intermediate 76) except that THF was used as the solvent. The crude product was purified by reverse phase chromatography, eluting with 5-100% acetonitrile with acid modifier) and then recrystallised from a mixture of methyl tert-butyl ether and ethyl acetate to afford 4-hydroxy-6-{2-[2-methyl-4-(trifluoromethyl)phenyl]ethyl}-2,3-dihydropyridazin-3-one as a white powder (0.23 g, 36%).

$^1$H NMR (CD$_2$Cl$_2$) δ, 7.42 (s, 1 H), 7.39 (d, 1 H), 7.25 (d, 1 H), 6.60 (s, 1 H), 2.96-3.08 (m, 2 H), 2.77-2.90 (m, 2 H), and 2.38 (s, 3 H).

MS ES$^+$: 299.

M. p.=170-172° C.

Example 67

6-{2-[3,5-Difluoro-4-(trifluoromethyl)phenyl]ethyl}-4-hydroxy-2,3-dihydropyridazin-3-one

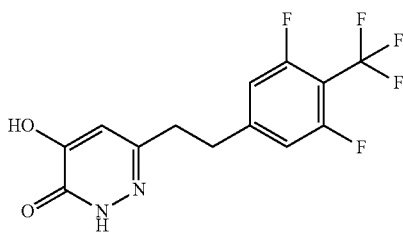 [SMILES: O=c1[nH]nc(CCc2cc(F)c(C(F)(F)F)c(F)c2)cc1O]

Prepared as described for 4-hydroxy-6-(2-phenylethyl)pyridazin-3(2H)-one (Example 1) from 3,4-bis(benzyloxy)-6-[(E)-2-[3,5-difluoro-4-(trifluoromethyl)phenyl]ethenyl]-pyridazine (Intermediate 77) except that THF was used as the solvent. The crude product was purified by reverse phase chromatography (silica, eluting with 5-100% acetonitrile in water with acid modifier) to afford a white solid, which was recrystallised from a mixture of methyl tert-butyl ether and ethyl acetate to afford 6-{2-[3,5-difluoro-4-(trifluoromethyl)phenyl]ethyl}-4-hydroxy-2,3-dihydropyridazin-3-one as a white solid (0.079 g, 10%).

$^1$H NMR (CD$_3$OD) δ 7.09 (d, 2 H), 6.64 (s, 1 H), 3.00-3.10 (m, 2 H) and 2.82-2.96 (m, 2 H).

MS ES$^+$: 321.

M.p.=211-212° C.

Example 68

6-{2-[3-Fluoro-4-(trifluoromethyl)phenyl]ethyl}-4-hydroxy-2,3-dihydropyridazin-3-one

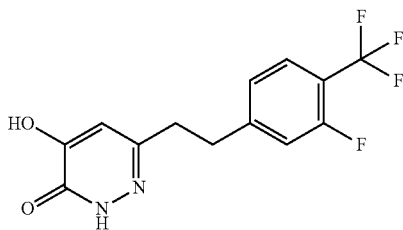 [SMILES: O=c1[nH]nc(CCc2ccc(C(F)(F)F)c(F)c2)cc1O]

Prepared as described for 4-hydroxy-6-(2-phenylethyl)pyridazin-3(2H)-one (Example 1) from 3,4-bis(benzyloxy)-6-[(E)-2-[3-fluoro-4-(trifluoromethyl)phenyl]ethenyl]pyridazine (Intermediate 79) in 60% yield. The solid was purified by reverse phase chromatography, eluting with 5-100% acetonitrile in water with acid modifier to yield 6-{2-[3-fluoro-4-(trifluoromethyl)phenyl]ethyl}-4-hydroxy-2,3-dihydropyridazin-3-one in 60% yield.

$^1$H NMR (DMSO-d$_6$) δ 12.68 (s, 1 H), 10.76 (br. s., 1 H), 7.68 (m, 1 H), 7.42 (m, 1 H), 7.27 (m, 1 H), 6.61 (s, 1 H), 2.93-3.04 (m, 2 H) and 2.73-2.87 (m, 2 H).

MS ES$^+$: 303.

3. BIOLOGICAL EFFICACY OF COMPOUNDS OF THE INVENTION

In Vitro DAAO Enzyme Assay

The functional activity of compounds inhibiting the DAAO enzyme was determined by utilizing the co-product of the catalysis of D-Serine, H$_2$O$_2$ which can be quantitatively measured using the 'Amplex' (trade mark) Red (Invitrogen) detection. 'Amplex' Red reagent is a colorless substrate that reacts with hydrogen peroxide (H$_2$O$_2$) with a 1:1 stoichiometry in the presence of hydrogen peroxide to produce highly fluorescent resorufin (excitation/emission maxima=570/585 nm). The changes in fluorescence were monitored by a fluorescence plate reader, Envision (Perkin Elmer) and increases in DAAO activity were readily detected upon addition of D-Serine and suppression of this response observed with the application of test compounds.

Human DAAO enzyme was supplied by the Takeda Pharmaceutical Company (Osaka) and each batch was tested and used at concentrations giving comparable levels of activity. The K$_m$ of D-Serine was measured for each enzyme batch to maintain consistency; this K$_m$ was used in subsequent assays.

On the day of the assay compounds were serially diluted in DMSO before being diluted 1:20 with assay buffer (20 mM Tris ph 7.4). A 5 µl portion of assay buffer was added to the wells of a 384 clear base black-walled plate (Corning), 5 µl of diluted compound was then added via automated plate to plate transfer using the Bravo liquid handler (Agilent technologies) followed by 5 µl of human DAAO enzyme and then 5 µl D-Serine 50 mM was added to all but the negative control wells (final concentration of 10 mM). Finally 5 µl 'Amplex' red reagent (Invitrogen) was added to all wells as per manufacturer's protocol. The plate was incubated for 60 minutes in the dark at 25° C. and the fluorescence in each well was measured in the Envision plate reader.

The IC$_{50}$ values for compounds were determined from ten point half log scale dose-response studies and represent the concentration of compound required to prevent 50% inhibition of DAAO activity in the presence of 10 mM D-Serine. Concentration response curves were generated using the average of duplicate wells for each data point and analyzed using non-linear regression and four parameter curve fit.

Results

| Example No. | Mean IC$_{50}$ (nM) | Example No. | Mean IC$_{50}$ (nM) |
|---|---|---|---|
| 1 | 10 | 2 | 10 |
| 3 | 21 | 4 | 3.7 |
| 5 | 30 | 6 | 9.7 |
| 7 | 13 | 8 | 11 |
| 9 | 10 | 10 | 22 |
| 11 | 16 | 12 | 23 |
| 13 | 31 | 14 | 41 |
| 15 | 16 | 16 | 52 |
| 17 | 13 | 18 | 14 |
| 19 | 12 | 20 | 8.4 |

-continued

| Example No. | Mean IC$_{50}$ (nM) | Example No. | Mean IC$_{50}$ (nM) |
|---|---|---|---|
| 21 | 21 | 22 | 13 |
| 23 | 14 | 24 | 6 |
| 25 | 45 | 26 | 22 |
| 27 | 13 | 28 | 20 |
| 29 | 45 | 30 | 18 |
| 31 | 20 | 32 | 16 |
| 33 | 23 | 34 | 26 |
| 35 | 41 | 36 | 19 |
| 37 | 220 | 38 | 20 |
| 39 | 13 | 40 | 12 |
| 41 | 99 | 42 | 15 |
| 43 | 26 | 44 | 22 |
| 45 | 18 | 46 | 15 |
| 47 | 26 | 48 | 12 |
| 49 | 23 | 50 | 23 |
| 51 | 30 | 52 | 130 |
| 53 | 19 | 54 | 14 |
| 55 | 760 | 56 | 32 |
| 57 | 380 | 58 | 61 |
| 59 | 19 | 60 | 15 |
| 61 | 57 | 62 | 29 |
| 63 | 15 | 64 | 13 |
| 65 | 13 | 66 | 12 |
| 67 | 10 | 68 | 19 |

These results indicate that compounds of the invention have potent inhibitory activity against the DAAO enzyme. The compounds tested above exhibit IC$_{50}$ values significantly less than 5 μM, with the most potent compounds showing activity at the DAAO enzyme with IC$_{50}$ values <250 nM. Accordingly, the compounds of the invention are expected to have usefulness in the prevention or treatment of conditions, such as those discussed above, in which DAAO enzyme activity is implicated.

In addition, the compounds of the present invention possess variously advantageous pharmacological and/or toxicological profiles, when tested in a variety of standard tests for such parameters. For example, the compounds of the invention exhibit one or more potentially useful properties for in vivo use, when characterised by pharmacological and/or toxicological tests including: bERG interaction (which is an indication of potential cardiotoxicity, and measures the effects of the compounds on the human ether-a-go-go-related gene, using for example the PatchXpress 7000A platform); CypP$_{450}$ interactions (which may be measured in accordance with the FDA draft guidelines for drug interaction studies (study design, data analysis and implications for dosing and labeling) (September 2006), see www.fda.gov); phototoxicity (for example using a protocol in accordance with assay details outlined in the OECD guidelines for testing of chemicals: 432 In Vitro 3T3 Neutral Red Uptake phototoxicity test, April 2004); determination of pharmacokinetic parameters (for example following in vivo dosing via multiple routes, with plasma concentrations of compounds being determined from venous blood samples using an LC-MS/MS protocol); and in vivo receptor occupancy (determined, for example, using protocols based on Medhurst et al., *Journal of Pharmacology and Experimental Therapeutics*, 2007, 321, 1032). These standard tests for the characterisation of drug molecules are well known to the skilled person.

The invention claimed is:

1. A method of treating at least one symptom or condition associated with schizophrenia comprising administering to a patient in need thereof a therapeutically effective amount of a compound of formula (I), or a pharmaceutically acceptable salt thereof,

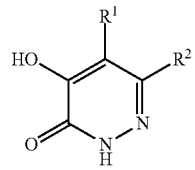

(I)

wherein
R$^1$ is chosen from a hydrogen or fluorine atom or a trifluoromethyl group;
R$^2$ represents a group —X—Y—R$^3$;
X and Y each independently are chosen from a bond, an oxygen atom, or a group —C(O), —S(O)$_n$, —C(O)NR$^4$, —S(O)$_2$NR$^4$, —NR$^4$,

or —CR$^4$R$^5$—, with the proviso that X and Y cannot both simultaneously represent a bond, and if X and Y are both not a bond, then at least one of X and Y represents —CR$^4$R$^5$—;
n is chosen from 0, 1 or 2;
each R$^4$ independently is chosen from a hydrogen atom or a C$_1$-C$_6$ alkyl or C$_1$-C$_6$ haloalkyl group;
each R$^5$ independently is chosen from a hydrogen atom, a C$_1$-C$_6$ alkyl or C$_1$-C$_6$ haloalkyl group or =CH—;
R$^3$ is chosen from a 3- to 10-membered saturated or unsaturated carbocyclic or heterocyclic ring system, wherein the ring system is unsubstituted or substituted by at least one substituent chosen from halogen, hydroxyl, cyano, oxo, C$_1$-C$_6$ alkyl, C$_2$-C$_6$ alkenyl, C$_1$-C$_6$ haloalkyl, C$_1$-C$_6$ hydroxyalkyl, C$_1$-C$_6$ alkoxy, C$_1$-C$_6$ haloalkoxy, C$_1$-C$_6$ alkylthio, C$_1$-C$_6$ alkylsulphinyl, C$_1$-C$_6$ alkylsulphonyl, C$_1$-C$_6$ alkylcarbonyl, C$_1$-C$_6$ alkylcarbonyloxy, C$_1$-C$_6$ alkoxycarbonyl, amino (—NH$_2$), —CON(R$^6$)$_2$, C$_1$-C$_6$ alkylamino, di-(C$_1$-C$_6$ alkyl)amino, C$_3$-C$_6$ cycloalkyl, C$_3$-C$_6$ cycloalkyloxy, C$_3$-C$_6$ cycloalkylmethyl, —[O]$_p$—(CH$_2$)$_q$—O—R$^7$ or a 4- to 6-membered saturated or unsaturated heterocyclic ring, which is unsubstituted or substituted with at least one substituent chosen from C$_1$-C$_4$ alkyl or C$_1$-C$_4$ alkoxy;
each R$^6$ independently is chosen from a hydrogen atom or a C$^1$-C$^6$ alkyl group;
p is chosen from 0 or 1;
q is chosen from 1, 2, 3 or 4; and
R$^7$ is chosen from a C$_1$-C$_6$ alkyl group.

2. The method according to claim 1, wherein the at least one symptom is a positive symptom of schizophrenia.

3. The method according to claim 1, wherein the at least one symptom is a negative symptom of schizophrenia.

4. The method according to claim 2, wherein the positive symptom of schizophrenia is chosen from hearing voices that others do not experience, seeing hallucinations, or cognitive impairment associated with schizophrenia.

5. The method according to claim 4, wherein the positive symptom of schizophrenia is cognitive impairment associated with schizophrenia.

6. The method according to claim 1, wherein the compound of formula (I) is chosen from:
4-Hydroxy-6-(2-phenylethyl)pyridazin-3(2H)-one,
6-[2-(4-Fluorophenyl)ethyl]-4-hydroxypyridazin-3(2H)-one, 4-Hydroxy-6-{2-[5-(trifluoromethyl)pyridin-2-yl]ethyl}pyridazin-3(2H)-one,
6-[(4-Chlorobenzyl)sulfanyl]-4-hydroxypyridazin-3(2H)-one,
4-Hydroxy-6-{2-[6-(trifluoromethyl)pyridin-3-yl]ethyl}pyridazin-3(2H)-one,
6-[2-(3-Fluorophenyl)ethyl]-4-hydroxypyridazin-3(2H)-one,
6-[2-(2-Fluorophenyl)ethyl]-4-hydroxypyridazin-3(2H)-one,
6-[2-(3, 5-Difluorophenyl)ethyl]-4-hydroxypyridazin-3(2H)-one,
6-[2-(3,4-Difluorophenyl)ethyl]-4-hydroxypyridazin-3(2H)-one,
4-Hydroxy-6-{2-[3-(trifluoromethoxy)phenyl]ethyl}pyridazin-3(2H)-one,
4-Hydroxy-6-{2-[3-(trifluoromethyl)phenyl]ethyl}pyridazin-3(2H)-one,
4-Hydroxy-6-{2-[5-(trifluoromethyl)pyridin-3-yl]ethyl}pyridazin-3(2H)-one,
6-(2-Cyclohexylethyl)-4-hydroxypyridazin-3(2H)-one,
6-(2-Cyclopropylethyl)-4-hydroxypyridazin-3(2H)-one,
6-(2-Cyclopentylethyl)-4-hydroxypyridazin-3(2H)-one,
4-Hydroxy-6-[2-(4-methoxycyclohexyl)ethyl]pyridazin-3(2H)-one,
6-[2-(2,4-Difluorophenyl)ethyl]-4-hydroxypyridazin-3(2H)-one,
6-{2-[3-(Difluoromethyl)phenyl]ethyl}-4-hydroxypyridazin-3(2H)-one,
6-Benzyl-4-hydroxypyridazin-3(2H)-one,
6-[2-(3-Chlorophenyl)ethyl]-4-hydroxypyridazin-3(2H)-one,
4-Hydroxy-6-(1-phenylcyclopropyl)pyridazin-3(2H)-one,
4-[2-(5-Hydroxy-6-oxo-1,6-dihydropyridazin-3-yl)ethyl]benzonitrile,
6-[2-(3-Fluoro-4-methylphenyl)ethyl]-4-hydroxypyridazin-3(2H)-one,
6-[2-(4-Fluoro-3-methylphenyl)ethyl]-4-hydroxypyridazin-3(2H)-one,
6-[2-(3,4-Dimethoxyphenyl)ethyl]-4-hydroxypyridazin-3(2H)-one,
4-Hydroxy-6-{2-[3-(trifluoromethoxy)phenyl]ethyl}pyridazin-3(2H)-one,
6-[2-(4-Chlorophenyl)ethyl]-4-hydroxypyridazin-3(2H)-one,
6-[2-(2-Chlorophenyl)ethyl]-4-hydroxypyridazin-3(2H)-one,
4-Hydroxy-6-{2-[2-(trifluoromethyl)phenyl]ethyl}pyridazin-3(2H)-one,
6-(4-Difluoromethoxy)phenethyl)-4-hydroxypyridazin-3(2H)-one,
6-(4-(Trifluoromethoxy)phenethyl)-4-hydroxypyridazin-3(2H)-one,
6-(3-(Difluoromethoxy)phenethyl)-4-hydroxypyridazin-3(2H)-one,
6-[1-(4-Fluorophenyl)cyclopropyl]-4-hydroxypyridazin-3(2H)-one,
6-[1-(4-Fluorophenyl)ethyl]-4-hydroxypyridazin-3(2H)-one,
4-Hydroxy-6-{1-[3-(trifluoromethyl)phenyl]ethyl}pyridazin-3(2H)-one,
4-Hydroxy-6-{2-[4-(trifluoromethyl)phenyl]ethyl}pyridazin-3(2H)-one,
6-(((Cyclopropylmethyl)(methyl)amino)-4-hydroxypyridazin-3(2H)-one,
6-(((Cyclohexylmethyl)(methyl)amino)-4-hydroxypyridazin-3(2H)-one,
6-(3-Chlorobenzyl)-4-hydroxypyridazin-3(2H)-one,
6-(4-Chlorobenzyl)-4-hydroxypyridazin-3(2H)-one,
6-(Cyclohexylmethyl)-4-hydroxypyridazin-3(2H)-one,
6-(4-Fluorobenzyl)-4-hydroxypyridazin-3(2H)-one,
6-(2-Chloro-6-fluorobenzyl)-4-hydroxypyridazin-3(2H)-one,
6-(2-Chlorobenzyl)-4-hydroxypyridazin-3(2H)-one,
6-(3-Fluorobenzyl)-4-hydroxypyridazin-3(2H)-one,
6-(2-Fluorobenzyl)-4-hydroxypyridazin-3(2H)-one,
6-(4-Methylbenzyl)-4-hydroxypyridazin-3(2H)-one,
6-(3-Methylbenzyl)-4-hydroxypyridazin-3(2H)-one,
4-Hydroxy-6-(3-(trifluoromethyl)benzyl)pyridazin-3(2H)-one,
4-Hydroxy-6-{2-[5-(trifluoromethyl)pyridin-3-yl]ethyl}pyridazin-3(2H)-one,
4-Hydroxy-6-[2-(oxan-4-yl)ethyl]pyridazin-3(2H)-one,
6-{[(4-Fluorophenyl)methyl](methyl)amino}-4-hydroxypyridazin-3(2H)-one,
6-[2-(2,6-Difluorophenyl)ethyl]-4-hydroxy-pyridazin-3(2H)-one,
6-[2-(2-Chloro-6-fluorophenyl)ethyl]-4-hydroxypyridazin-3(2H)-one,
6-{[3,5-bis(Trifluoromethyl)phenyl]methyl}-4-hydroxypyridazin-3(2H)-one,
6-(1-Phenylethyl)-4-hydroxypyridazin-3(2H)-one,
6-(Cyclopropylmethyl)-4-hydroxy-2,3-dihydropyridazin-3-one,
4-Hydroxy-6-{-[4-(trifluoromethyl)phenyl]cyclopropyl}-2,3-dihydropyridazin-3-one,
6-{2-[2-Chloro-4-(trifluoromethyl)phenyl]ethyl}-4-hydroxy-2,3-dihydropyridazin-3-one,
6-{2-[2-Fluoro-4-(trifluoromethyl)phenyl]ethyl}-4-hydroxy-2,3-dihydropyridazin-3-one,
6-{2-[3,5-bis(Trifluoromethyl)phenyl]ethyl}-4-hydroxy-2,3-dihydropyridazin-3-one,
6-{2-[2,4-bis(Trifluoromethyl)phenyl]ethyl}-4-hydroxy-2,3-dihydro-pyridazin-3-one,
6-{2-[3,4-bis(Trifluoromethyl)phenyl]ethyl}4-hydroxy-2,3-dihydropyridazin-3-one,
4-Hydroxy-6-(3-methyl-4-(trifluoromethyl)phenethyl)pyridazin-3(2H)-one,
3,4-bis(Benzyloxy)-6-((3-chloro-4-(trifluoromethyl)phenyl)ethyl)pyridazine,
4-Hydroxy-6-{2-[2-methyl-4-(trifluoromethyl)phenyl]ethyl}-2,3-dihydropyridazin-3-one,
6-{2-[3,5-Difluoro-4-(trifluoromethyl)phenyl]ethyl}-4-hydroxy-2,3-dihydropyridazin-3-one, and
6-{2-[3-Fluoro-4-(trifluoromethyl)phenyl]ethyl}-4-hydroxy-2,3-dihydropyridazin-3-one,
or a pharmaceutically acceptable salt thereof.

7. The method according to claim 6, wherein the compound of formula (I) is chosen from:
6-[2-(4-Fluorophenyl)ethyl]-4-hydroxypyridazin-3(2H)-one,
4-Hydroxy-6-{2-[4-(trifluoromethyl)phenyl]ethyl}pyridazin-3(2H)-one, and
6-(4-Chlorobenzyl)-4-hydroxypyridazin-3(2H)-one,
or a pharmaceutically acceptable salt thereof.

8. The method according to claim 1, wherein the compound of formula (I) is 6-[2-(4-Fluorophenyl)ethyl]-4-hydroxypyridazin-3(2H)-one or a pharmaceutically acceptable salt thereof.

9. The method according to claim 1, wherein the compound of formula (I) is 4-Hydroxy-6-{2-[4-(trifluoromethyl)phenyl]ethyl}pyridazin-3(2H)-one or a pharmaceutically acceptable salt thereof.

10. The method according to claim 1, wherein the compound of formula (I) is 6-(4-Chlorobenzyl)-4-hydroxypyridazin-3(2H)-one or a pharmaceutically acceptable salt thereof.

* * * * *

UNITED STATES PATENT AND TRADEMARK OFFICE
CERTIFICATE OF CORRECTION

PATENT NO. : 9,931,340 B2
APPLICATION NO. : 15/014336
DATED : April 3, 2018
INVENTOR(S) : Farnaby et al.

It is certified that error appears in the above-identified patent and that said Letters Patent is hereby corrected as shown below:

In the Claims

Claim 7, Column 97, Lines 11-12, "6-[2-(3, 5-Difluorophenyl)ethyl]-4-hydroxypyridazin-3(2H)-one" should read as --6-[2-(3,5-Difluorophenyl)ethyl]-4-hydroxypyridazin-3(2H)-one,--.

Signed and Sealed this
Tenth Day of July, 2018

Andrei Iancu
*Director of the United States Patent and Trademark Office*